(12) United States Patent
Huang et al.

(10) Patent No.: US 11,396,541 B2
(45) Date of Patent: Jul. 26, 2022

(54) ANTI-INTERLEUKIN-23 P19 ANTIBODIES AND METHODS OF USE THEREOF

(71) Applicant: NOVAROCK BIOTHERAPEUTICS, LTD., Ewing, NJ (US)

(72) Inventors: Haichun Huang, Fremont, CA (US); Ming Lei, Princeton, NJ (US); Yi Pei, Paoli, PA (US); Han Li, Newtown, PA (US)

(73) Assignee: NOVAROCK BIOTHERAPEUTICS, LTD., Ewing, NJ (US)

( * ) Notice: Subject to any disclaimer, the term of this patent is extended or adjusted under 35 U.S.C. 154(b) by 0 days.

(21) Appl. No.: 17/097,496

(22) Filed: Nov. 13, 2020

(65) Prior Publication Data
US 2021/0188961 A1   Jun. 24, 2021

Related U.S. Application Data

(60) Provisional application No. 62/951,231, filed on Dec. 20, 2019.

(51) Int. Cl.
A61K 39/395 (2006.01)
C07K 16/24 (2006.01)

(52) U.S. Cl.
CPC ........ *C07K 16/244* (2013.01); *C07K 2317/24* (2013.01); *C07K 2317/565* (2013.01)

(58) Field of Classification Search
CPC ............ C07K 16/244; C07K 2317/565; A61K 2039/505; A61K 39/3955
See application file for complete search history.

(56) References Cited

U.S. PATENT DOCUMENTS

| | | |
|---|---|---|
| 8,293,883 B2 | 10/2012 | Presta |
| 8,404,813 B2 | 3/2013 | Presta |
| 8,513,389 B2 | 8/2013 | Presta et al. |
| 8,722,033 B2 | 5/2014 | Towne et al. |
| 9,023,358 B2 | 5/2015 | Beidler et al. |
| 9,688,753 B2 | 6/2017 | Beidler et al. |
| 11,078,265 B2 | 8/2021 | Nabozny et al. |
| 2021/0070852 A1 | 3/2021 | Garidel et al. |

FOREIGN PATENT DOCUMENTS

| | | |
|---|---|---|
| WO | 2007076524 A2 | 7/2007 |
| WO | 2012061448 A1 | 5/2012 |
| WO | 2014093203 A1 | 6/2014 |
| WO | 2017049035 A1 | 3/2017 |

OTHER PUBLICATIONS

Furue, Kazuhisa et al: "Differential efficacy of biologic treatments targeting the TNF-[alpha]/IL-23/IL-17 axis in psoriasis and psoriatic arthritis", Cytokine, Academic Press Ltd, Philadelphia, PA, US, vol. 111, Aug. 29, 2018 (Aug. 29, 2018), pp. 182-188 (7 pages), XP085557967.

Sheng, Cheng et al: "Blockade of IL-23 ameliorates allergic lung inflammation via decreasing the infiltration of Tc17 cells", Archives of Medical Science, vol. 6, Jan. 1, 2016 (Jan. 1, 2016), pp. 1362-1369 (8 pages), XP055707412.

Argollo, Marjorie C. et al: "Interleukin-23 Blockers: Born to be First-line Biologic Agents in Inflammatory Bowel Disease?", Current Pharmaceutical Design, vol. 25, No. 1, May 23, 2019 (May 23, 2019), pp. 25-31 (7 pages), XP055778618.

Bachelez, Hervé: "Interleukin 23 inhibitors for psoriasis: not just another number", The Lancet, Elsevier, Amsterdam, NL, vol. 390, No. 10091, Jun. 6, 2017 (Jun. 6, 2017), pp. 208-210 (3 pages), XP085126187.

Sandborn, William J et al, "Efficacy and Safety of Mirikizumab in a Randomized Phase 2 Study of Patients With Ulcerative Colitis", Gastroenterology, Elsevier Inc, US, vol. 158, No. 3, Sep. 4, 2019 (Sep. 4, 2019), pp. 537-549 (23 pages), XP085999269.

Conrad, Curdin et al, "Psoriasis: from Pathogenesis to Targeted Therapies", Clinical Reviews in Allergy and Immunology, Humana Press Totowa, NJ, US, , vol. 54, No. 1, Jan. 18, 2018 (Jan. 18, 2018), pp. 102-113 (12 pages), XP036423716.

Reich Kristian et al: "Tildrakizumab versus placebo or etanercept for chronic plaque psoriasis (reSURFACE 1 and reSURFACE 2): results from two randomised controlled, phase 3 trials", The Lancet, Elsevier, Amsterdam, NL, vol. 390, No. 10091, Jun. 6, 2017 (Jun. 6, 2017), pp. 276-288 (13 pages), XP085126183.

International Search Report and Written Opinion dated May 4, 2021, for International application No. PCT/US2020/060539 (22 pages).

Ahmad Ismail Khaled Abdo et al., Interleukin 23 and autoimmune diseases: current and possible future therapies, Inflammation Research, Mar. 25, 2020, pp. 463-480, vol. 69, Springer Nature Switzerland AG (18 pages).

Sudeepta Aggarwal et al., Interleukin-23 Promotes a Distinct CD4 T Cell Activation State Characterized by the Production of Interleukin-17, The Journal of Biological Chemistry, Jan. 17, 2003, pp. 1910-1914, vol. 278, No. 3, The American Society for Biochemistry and Molecular Biology, Inc. USA (6 pages).

Mariangela Allocca et al., Can IL-23 be a good target for ulcerative colitis?, Elsevier Best Practice & Research Clinical Gastroenterology 32-33 (2018), pp. 95-102, Milan, Italy (8 pages).

S. Angal et al., A Single Amino Acid Substitution Abolishes the Heterogeneity of Chimeric Mouse/Human (IgG4) Antibody, Molecular Immunology, vol. 30, No. 1, pp. 105-108 (1993) London, UK (4 pages).

(Continued)

*Primary Examiner* — Dong Jiang
(74) *Attorney, Agent, or Firm* — Morgan, Lewis & Bockius LLP; Christopher J. Betti

(57) ABSTRACT

The present disclosure provides antibodies and antibody fragments thereof that bind to IL-23p19. The disclosed antibodies and antibody fragments thereof can modulate a biological activity of the IL-23 receptor signaling axis and are therefore useful for the treatment of immune-mediated inflammatory disorders.

13 Claims, 18 Drawing Sheets
Specification includes a Sequence Listing.

(56) References Cited

OTHER PUBLICATIONS

Yehudi Bloch et al., Structural activation of pro-inflammatory human cytokine IL-23 by cognate IL-23 receptor enables recruitment of the shared receptor IL-12Rβ1, Immunity Jan. 16, 2018, vol. 48(1), Germany, pp. 45-58 (34 pages).
Kübra Bunte, Th17 Cells and the IL-23/IL-17 Axis in the Pathogenesis of Periodontitis and Immune-Mediated Inflammatory Diseases, International Journal of Molecular Sciences, 2019, 20, 3394, Switzerland, pp. 1-24 (24 pages).
Arianna Calcinotto et al., IL-23 secreted by myeloid cells drives castration-resistant prostate cancer, Research Article, 2018 Macmillan Publishers Limited, part of Springer Nature, Switzerland, pp. 1-27 (27 pages).
Alberto Cauli et al., Current perspective on the role of the interleukin-23/interleukin-17 axis in inflammation and disease (chronic arthritis and psoriasis), ImmunoTargets and Therapy 2015:4, Italy, pp. 185-190 (6 pages).
Antonella Di Cesare et al., The IL-23/Th17 Axis in the Immunopathogenesis of Psoriasis, Journal of Investigative Dermatology (2009), vol. 129, pp. 1339-1350 (12 pages).
Doreen M. Floss et al., Insights into IL-23 biology: From structure to function, Cytokine & Growth Factor Reviews 26 (2015), pp. 569-578, Dusseldorf, Germany (10 pages).
Christina Fotiadou et al., Targeting IL-23 in psoriasis: current perspectives, Psoriasis: Targets and Therapy 2018:8, pp. 1-5, Greece (5 pages).
George E. Fragoulis et al., Therapeutic Targeting of IL-17 and IL-23 Cytokines in Immune-Mediated Diseases, Annu. Rev. Med. 2016, vol. 67, UK, pp. 337-353 (21 pages).
Sarah L. Gaffen et al., IL-23-IL-17 immune axis: Discovery, Mechanistic Understanding, and Clinical Testing, Nat Rev Immunol. Sep. 2014; 14(9): pp. 585-600, PA, USA (34 pages).
Kamran Ghoreschi et al., Generation of pathogenic TH17 cells in the absence of TGF-b signalling, Nature, vol. 467, Oct. 21, 2010, pp. 967-972, (6 pages).
György Haskó et al., IL-12 as a therapeutic target for pharmacological modulation in immune-mediated and inflammatory diseases: regulation of T helper 1/T helper 2 responses, British Journal of Pharmacology (1999) 127, UK, pp. 1295-1304 (10 pages).
International Search Report and Written Opinion dated May 4, 2021, for International application No. PCT/US82020/060539 (25 pages).
Laure Jason-Moller et al., Overview of Biacore Systems and Their Applications, Current Protocols in Protein Science (2006) 19.13.1-19.13.14, pp. 1-14 (14 pages).
Georgios Kokolakis et al., Delayed Diagnosis of Hidradenitis Suppurativa and Its Effect on Patients and Healthcare System, Research Article, Dermatology, Apr. 26, 2020, pp. 1-10, Germany (10 pages).
Aran F. Labrijn et al., Therapeutic IgG4 antibodies engage in Fab-arm exchange with endogenous human IgG4 in vivo, Nature Biotechnology, vol. 27, No. 8, Aug. 2009, pp. 767-773, USA (7 pages).
Monica Lee Whitmire et al., NonClinical Dose Formulation Analysis Method Validation and Sample Analysis, The AAPS Journal, vol. 12, No. 4, Dec. 2010, pp. 628-634, USA (7 pages).
Kimiko Nakajima et al., Distinct Roles of IL-23 and IL-17 in the Development of Psoriasis-Like Lesions in a Mouse Model, The Journal of Immunology, 2011; 186:4481-4489, USA (12 pages).
Markus F. Neurath et al., IL-23 in inflammatory bowel diseases and colon cancer, Cytokine and Growth Factor Reviews 45 (2019), Germany, pp. 1-8 (8 pages).
Birgit Oppmann et al., Novel p19 Protein Engages IL-12p40 to Form a Cytokine, IL-23, with Biological Activities Similar as Well as Distinct from IL-12, Immunity, vol. 13, pp. 715-725, Nov. 2000, California, USA (11 pages).
Christi Parham et al., A Receptor for the Heterodimeric Cytokine IL-23 Is Composed of IL-12Rβ1 and a Novel Cytokine Receptor Subunit, IL-23R, The Journal of Immunology, 2002, 168, pp. 5699-5708 California, USA (10 pages).
Lorena Riol-Blanco et al., IL-23 receptor regulates unconventional IL-17-producing T cells that control infection, The Journal of Immunology, Feb. 15, 2010, 184(4), USA, pp. 1710-1720 (24 pages).
Robert Sabat et al., Hidradenitis suppurativa, Nature Reviews, Disease Primers, (2020) 6:18, pp. 1-20 (20 pages).
Sanjaya Singh et al., Selective targeting of the IL23 pathway: Generation and characterization of a novel high-affinity humanized anti-IL23A antibody, mAbs 7:4, pp. 778-791, Jul./Aug. 2015, Published with license by Taylor & Francis Group, LLC, USA (14 pages).
Chunlei Tang et al., Interleukin-23: as a drug target for autoimmune inflammatory diseases, Immunology, 135, The Journal of Cells, Molecules, Systems and Technologies, 2011, pp. 112-124 (13 pages).
William Tausend et al., Systematic Review of Interleukin-12, Interleukin-17, and Interleukin-23 Pathway Inhibitors for the Treatment of Moderate-to-Severe Chronic Plaque Psoriasis: Ustekinumab, Briakinumab, Tildrakizumab, Guselkumab, Secukinumab, Ixekizumab, and Brodalumab, Canadian Dermatology Association, Journal of Cutaneous Medicine and Surgery, vol. 18, No. 3 May/Jun. 2014: pp. 156-169, Canada (14 pages).
Michele W L Teng et al., IL-12 and IL-23 cytokines: from discovery to targeted therapies for immune-mediated inflammatory diseases, Nature Medicine, vol. 21, No. 7, Jul. 2015, pp. 719-729 USA (11 pages).
Dario A.A. Vignali et al., IL-12 Family Cytokines: Immunological Playmakers, Nat Immunol, 13(8), USA pp. 722-728 (16 pages).
Juming Yan et al., Interleukin (IL)-12 and IL-23 and Their Conflicting Roles in Cancer, Cold Spring Harb Perspect Biol 2018, pp. 1-19 (19 pages).
Liang Zhou et al., Transcriptional regulatory networks in Th17 cell differentiation, Curr Opin Immunol. Apr. 2009; 21(2): pp. 146-152, USA (12 pages).

FIG. 1A

SEQ ID NO: 1  Hu-2_VH
QVQLVQSGAEVKKPGASVKVSCKAS<u>GYTFTTYG</u>ISWVRQAPGQGLEWMGW<u>ISAYNGNT</u>KYAQKLQGR
VTMTTDTSTSTAYMELRSLRSDDTAVYYC<u>AREWRAFYYYGLDV</u>WGQGTTVTVSS

| GYTFTTYG | ISAYNGNT | AREWRAFYYYGLDV |
|---|---|---|
| SEQ: 9 | SEQ: 10 | SEQ: 11 |

SEQ ID NO: 2  Hu-2_VL
DIVMTQTPLSSPVTLGQPASISCRSS<u>QSLEHSDGNTY</u>LSWLQQRPNQPPRLLIY<u>KVS</u>NRFSGVPDRFSGS
GAGTDFTLKISRVEAEDVGVYYC<u>TQATQFPLT</u>FGGGTKVEIK

| QSLEHSDGNTY | KVS | TQATQFPLT |
|---|---|---|
| SEQ: 12 | SEQ: 13 | SEQ: 14 |

FIG. 1B

SEQ ID NO: 3  Hu-4_VH
QVHLVQSGAEVKKPGASVKVSCKAS<u>GYTFSSYG</u>INWVRQAPGQGLEWMGW<u>ISAYSGNT</u>DYSQHLQGR
VTMTTDTSTNTAYMELRSLRSDDTAVYYC<u>ARASANWYDYFDP</u>WGQGTLVTVSS

| GYTFSSYG | ISAYSGNT | ARASANWYDYFDP |
|---|---|---|
| SEQ: 15 | SEQ: 16 | SEQ: 17 |

SEQ ID NO: 4  Hu-4_VL
EIVLTQSPDFQSVTPKEKVTITCRAS<u>QTIGGS</u>LHWYQQKPDQSPKLLIT<u>YAS</u>QSFSGVPSRFSGSGSGTD
FTLTIHSLEAEDAATYYC<u>HQSSILPYT</u>FGQGTKLEIK

| QTIGGS | YAS | HQSSILPYT |
|---|---|---|
| SEQ: 18 | SEQ: 19 | SEQ: 20 |

FIG. 1C

SEQ ID NO: 5  Hu-5_VH
QLQLQESGPGLVKPSETLSLTCTVSGGSISSSSFYWGWIRQPPGKGLEWIGSIYYSGSTYYNPSLKSRVTI
SVDTSKNQFSLKLSSVTAADTAVYFCARHGVRGVIPHFDYWGQGTLVTVSS

| GGSISSSSFY | IYYSGST | ARHGVRGVIPHFDY |
|---|---|---|
| SEQ: 21 | SEQ: 22 | SEQ: 23 |

SEQ ID NO: 6  Hu-5_VL
QTVLTQEPSFSVSPGGTVTLTCGLNSGSVSTIYYPSWYQQTPGQAPRALIYSTNTRSSGVPDRFSGSILG
NKAALTITGAQADDESDYYCVLFLGSGLVFGGGTKLTVL

| SGSVSTIYY | STN | VLFLGSGLV |
|---|---|---|
| SEQ: 24 | SEQ: 25 | SEQ: 26 |

FIG. 1D

SEQ ID NO: 7  Hu-6_VH
QVQLVQSGAEVKKPGASVKVSCKTSGYTFTYYGISWVRQAPGQGLEWMGLISAYNGNTNYGQKVQGR
VTMTTDTSTSTAYMELRSLRSDDTAVYYCVTENINWRDAFDIWGQGTMVTVSS

| GYTFTYYG | ISAYNGNT | VTENINWRDAFDI |
|---|---|---|
| SEQ: 27 | SEQ: 28 | SEQ: 29 |

SEQ ID NO: 8  Hu-6_VL
EIVLTQSPDFQSVTPKEKVTITCRASQTIGSSLHWYQQKPDQSPKLLIKYASQSISGVPSRFSGSGSGTDF
TLTINSLEAEDAAAYYCHQSSSLPYTFGQGTKLEIK

| QTIGSS | YAS | HQSSSLPYT |
|---|---|---|
| SEQ: 30 | SEQ: 31 | SEQ: 32 |

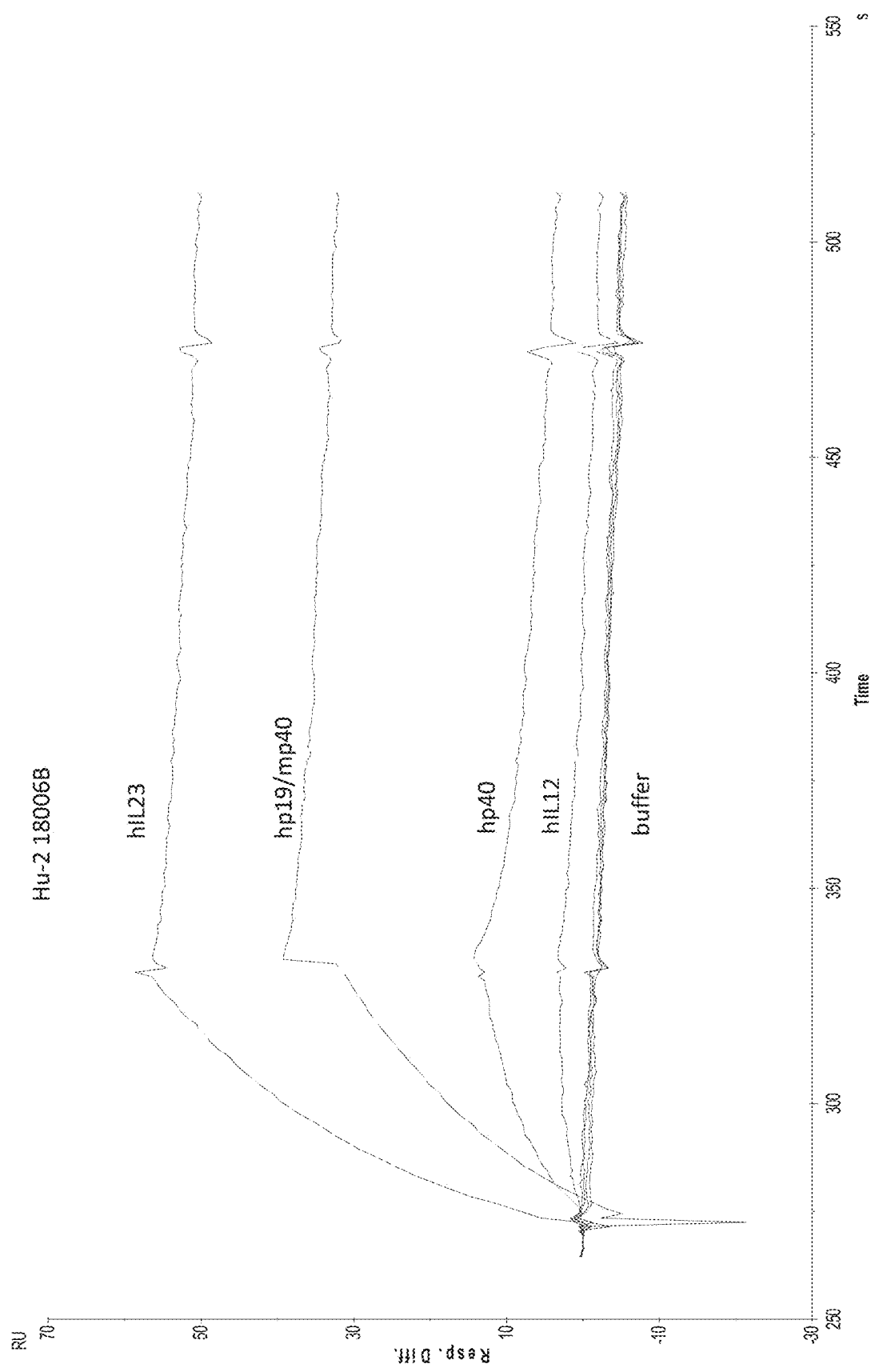

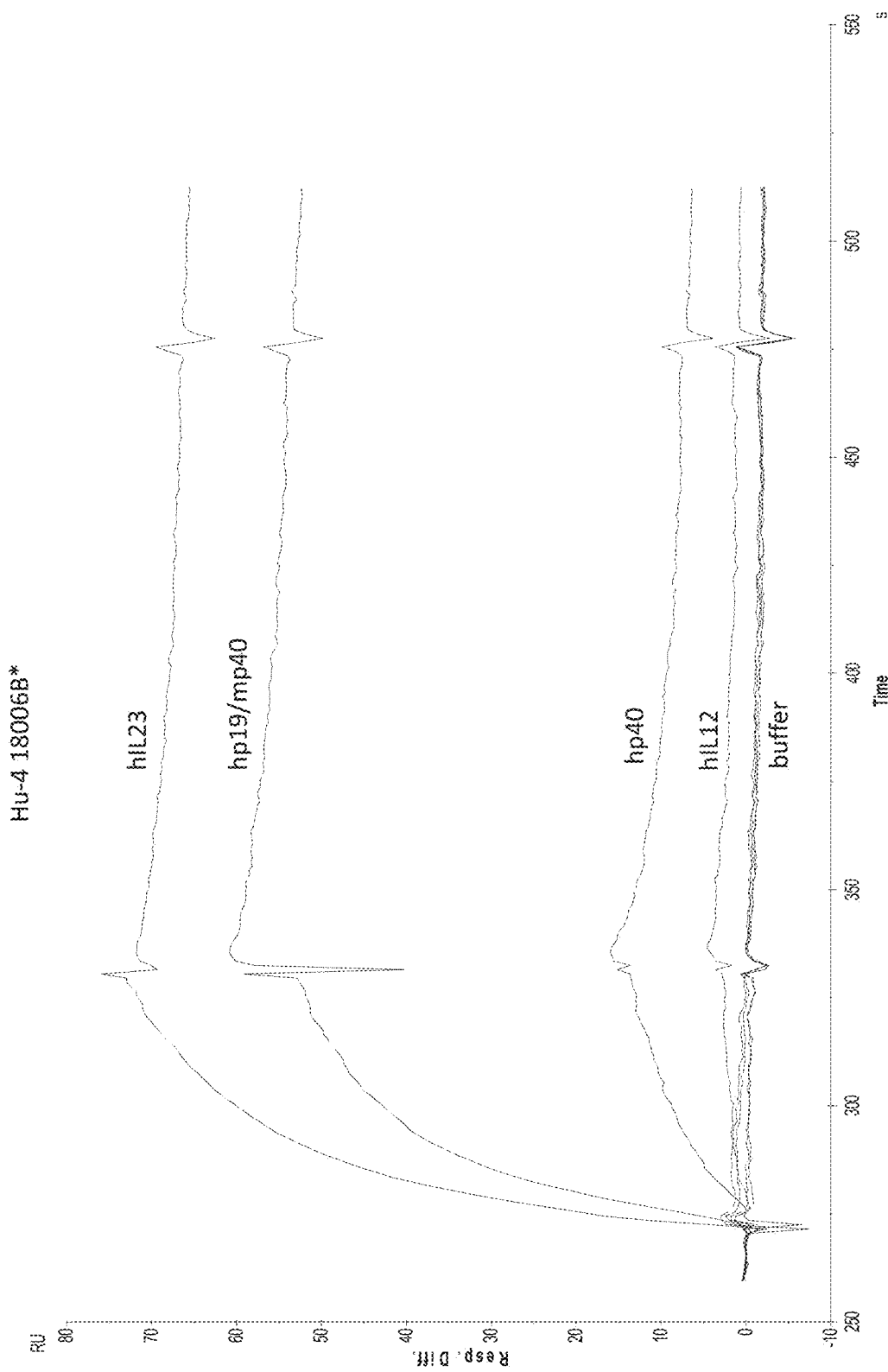

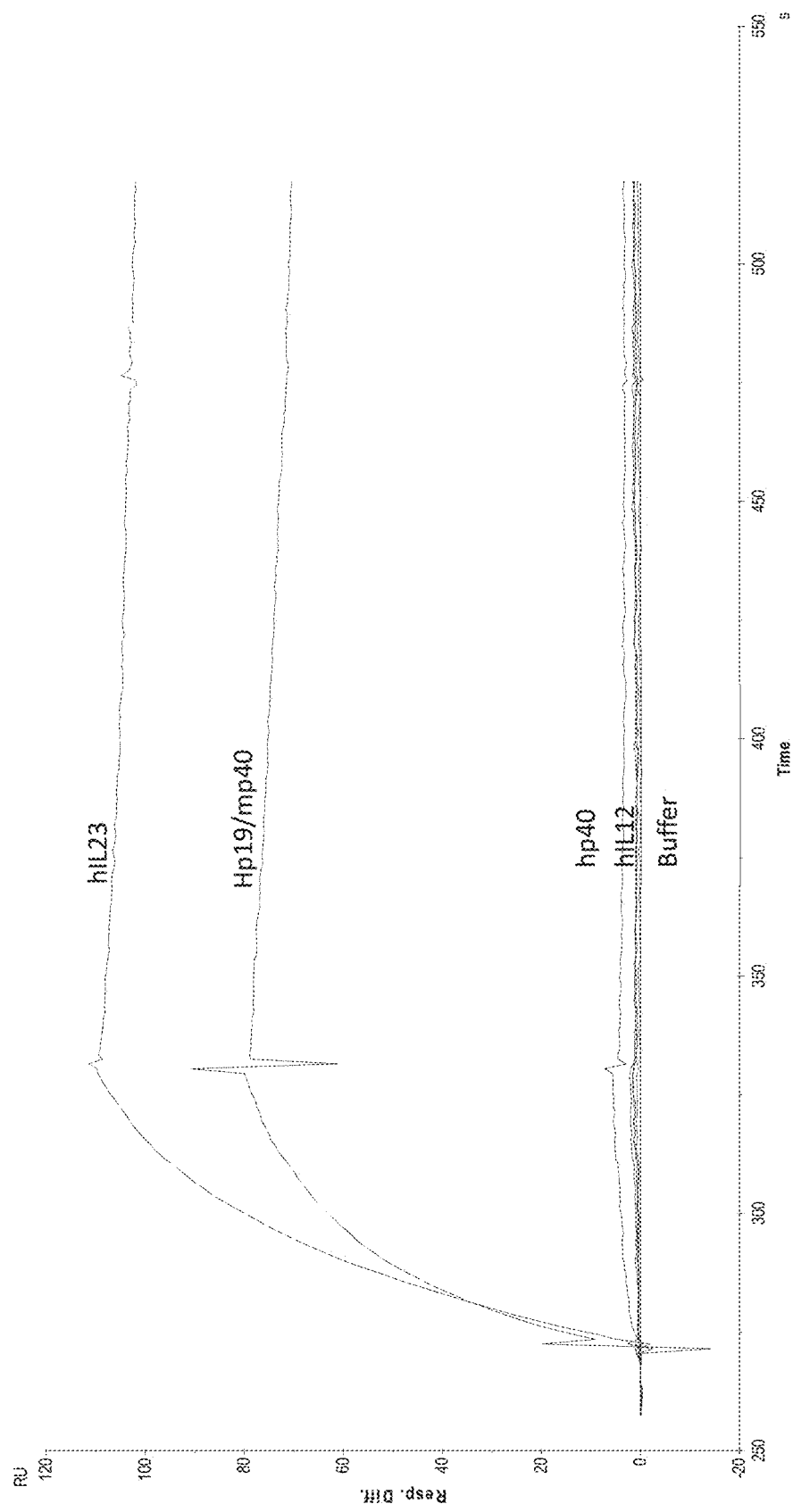

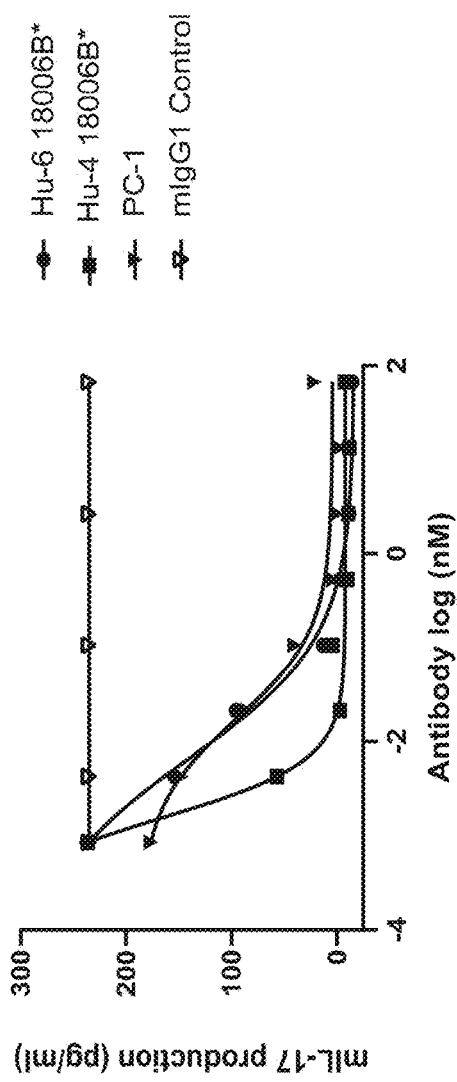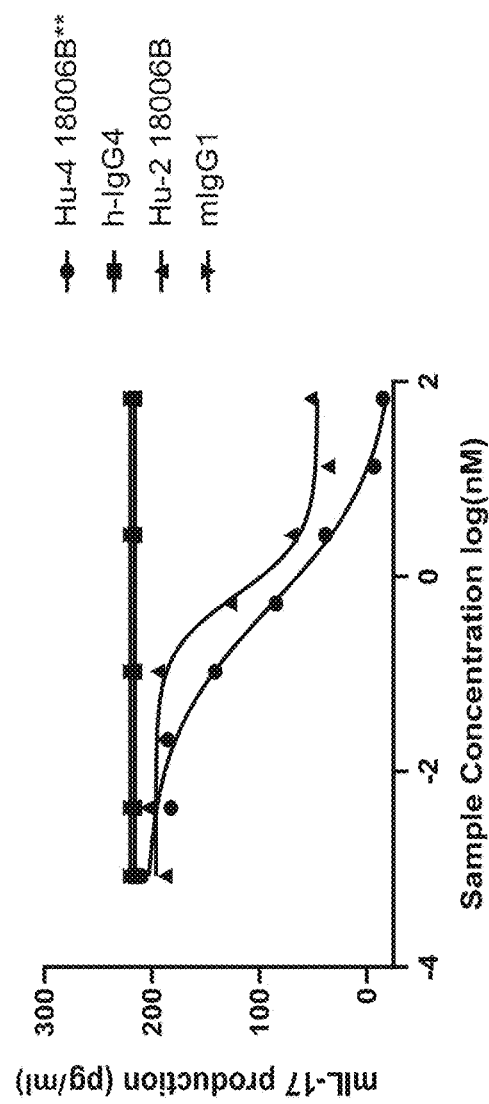
FIG. 6A
FIG. 6B

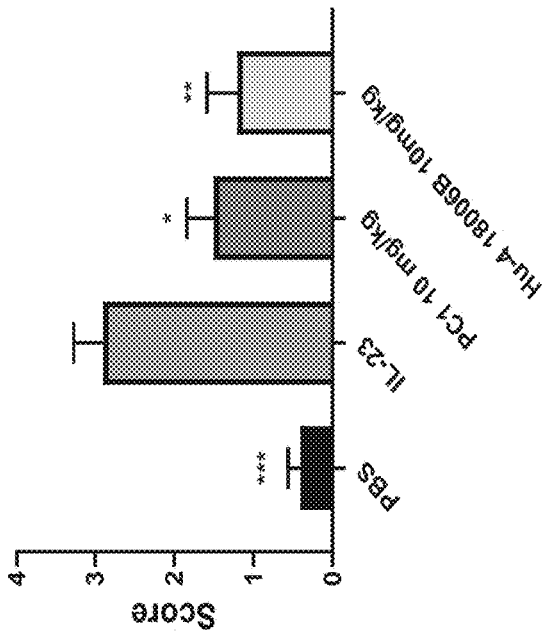
FIG. 11A
FIG. 11B
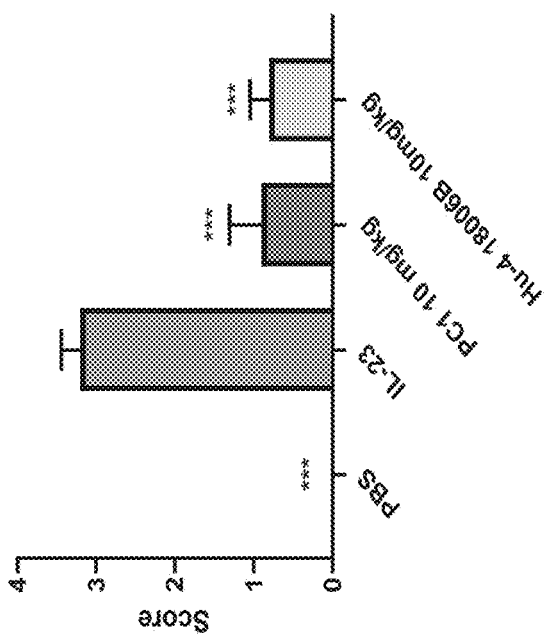
FIG. 11C
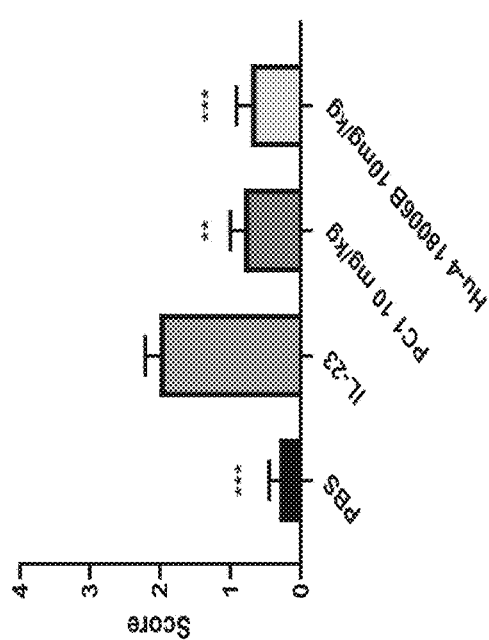
FIG. 11D

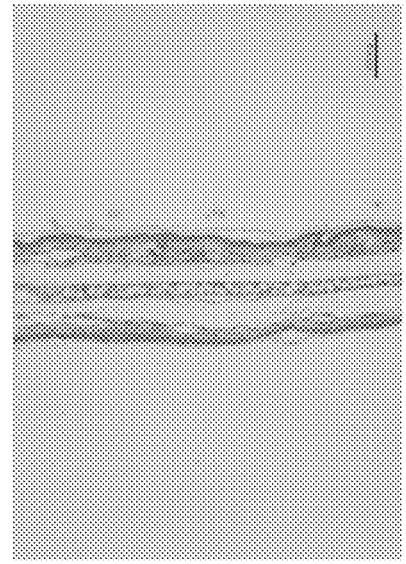
FIG. 12B
IL-23
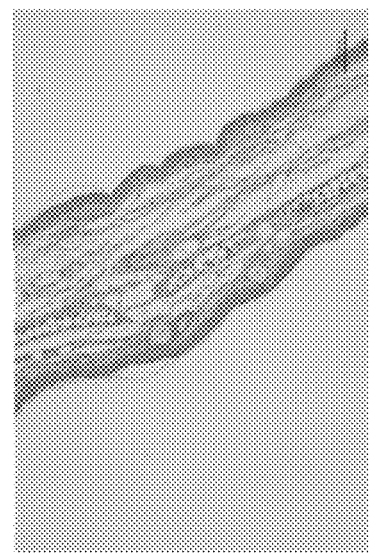
FIG. 12D
Hu-4 18006B
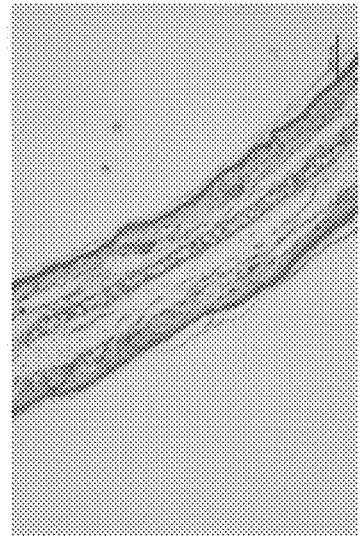
FIG. 12A
PBS
FIG. 12C
PC1

SEQUENCE LISTING

```
<160> NUMBER OF SEQ ID NOS: 32

<210> SEQ ID NO 1
<211> LENGTH: 121
<212> TYPE: PRT
<213> ORGANISM: Artificial Sequence
<220> FEATURE:
<223> OTHER INFORMATION: Hu-2_VH

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Trp Arg Ala Phe Tyr Tyr Tyr Gly Leu Asp Val Trp Gly
            100                 105                 110

Gln Gly Thr Thr Val Thr Val Ser Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Hu-2_VL

<400> SEQUENCE: 2

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Glu His Ser
            20                  25                  30

Asp Gly Asn Thr Tyr Leu Ser Trp Leu Gln Gln Arg Pro Asn Gln Pro
        35                  40                  45
```

```
Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Leu Thr Phe Gly Gly Gly Thr Lys Val Glu Ile Lys
            100                 105                 110
```

<210> SEQ ID NO 3
<211> LENGTH: 120
<212> TYPE: PRT
<213> ORGANISM: Artificial Sequence
<220> FEATURE:
<223> OTHER INFORMATION: Hu-4_VH

<400> SEQUENCE: 3

```
Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Gly Ile Asn Trp Val Arg Gln Ala Pro Gly Gln Gly Leu Glu Trp Met
        35                  40                  45

Gly Trp Ile Ser Ala Tyr Ser Gly Asn Thr Asp Tyr Ser Gln His Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Ser Ala Asn Trp Tyr Asp Tyr Phe Asp Pro Trp Gly Gln
            100                 105                 110

Gly Thr Leu Val Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: Hu--4_VL

<400> SEQUENCE: 4

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Thr Ile Gly Gly Ser
            20                  25                  30

Leu His Trp Tyr Gln Gln Lys Pro Asp Gln Ser Pro Lys Leu Leu Ile
        35                  40                  45

Thr Tyr Ala Ser Gln Ser Phe Ser Gly Val Pro Ser Arg Phe Ser Gly
    50                  55                  60

Ser Gly Ser Gly Thr Asp Phe Thr Leu Thr Ile His Ser Leu Glu Ala
65                  70                  75                  80

Glu Asp Ala Ala Thr Tyr Tyr Cys His Gln Ser Ser Ile Leu Pro Tyr
                85                  90                  95

Thr Phe Gly Gln Gly Thr Lys Leu Glu Ile Lys
            100                 105
```

<210> SEQ ID NO 5

-continued

<211> LENGTH: 122
<212> TYPE: PRT
<213> ORGANISM: Artificial Sequence
<220> FEATURE:
<223> OTHER INFORMATION: Hu-5_VH

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Phe Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg His Gly Val Arg Gly Val Ile Pro His Phe Asp Tyr Trp
            100                 105                 110

Gly Gln Gly Thr Leu Val Thr Val Ser Ser
        115                 120

<210> SEQ ID NO 6
<211> LENGTH: 109
<212> TYPE: PRT
<213> ORGANISM: Artificial Sequence
<220> FEATURE:
<223> OTHER INFORMATION: Hu-5_VL

<400> SEQUENCE: 6

Gln Thr Val Leu Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Ile
            20                  25                  30

Tyr Tyr Pro Ser Trp Tyr Gln Gln Thr Pro Gly Gln Ala Pro Arg Ala
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Phe Leu Gly Ser
                85                  90                  95

Gly Leu Val Phe Gly Gly Gly Thr Lys Leu Thr Val Leu
            100                 105

<210> SEQ ID NO 7
<211> LENGTH: 120
<212> TYPE: PRT
<213> ORGANISM: Artificial Sequence
<220> FEATURE:
<223> OTHER INFORMATION: Hu-6_VH

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Tyr Tyr
            20                  25                  30

Gly Ile Ser Trp Val Arg Gln Ala Pro Gly Gln Gly Leu Glu Trp Met
            35                  40                  45

Gly Leu Ile Ser Ala Tyr Asn Gly Asn Thr Asn Tyr Gly Gln Lys Val
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Val Thr Glu Asn Ile Asn Trp Arg Asp Ala Phe Asp Ile Trp Gly Gln
            100                 105                 110

Gly Thr Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Hu-6_VL

<400> SEQUENCE: 8

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Thr Ile Gly Ser Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys His Gln Ser Ser Ser Leu Pro Tyr
                 85                  90                  95

Thr Phe Gly Gln Gly Thr Lys Leu Glu Ile Lys
            100                 105

<210> SEQ ID NO 9
<211> LENGTH: 8
<212> TYPE: PRT
<213> ORGANISM: Artificial Sequence
<220> FEATURE:
<223> OTHER INFORMATION: Hu-2_VH-CDR1

<400> SEQUENCE: 9

Gly Tyr Thr Phe Thr Thr Tyr Gly
 1               5

<210> SEQ ID NO 10
<211> LENGTH: 8
<212> TYPE: PRT
<213> ORGANISM: Artificial Sequence
<220> FEATURE:
<223> OTHER INFORMATION: Hu-2_VH-CDR2

<400> SEQUENCE: 10

Ile Ser Ala Tyr Asn Gly Asn Thr
 1               5

<210> SEQ ID NO 11
<211> LENGTH: 14
<212> TYPE: PRT

```
<213> ORGANISM: Artificial Sequence
<220> FEATURE:
<223> OTHER INFORMATION: Hu-2_VH-CDR3

<400> SEQUENCE: 11

Ala Arg Glu Trp Arg Ala Phe Tyr Tyr Tyr Gly Leu Asp Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Hu-2_VL-CDR1

<400> SEQUENCE: 12

Gln Ser Leu Glu His Ser Asp Gly Asn Thr Tyr
1               5                   10

<210> SEQ ID NO 13
<211> LENGTH: 3
<212> TYPE: PRT
<213> ORGANISM: Artificial Sequence
<220> FEATURE:
<223> OTHER INFORMATION: Hu-2_VL-CDR2

<400> SEQUENCE: 13

Lys Val Ser
1

<210> SEQ ID NO 14
<211> LENGTH: 9
<212> TYPE: PRT
<213> ORGANISM: Artificial Sequence
<220> FEATURE:
<223> OTHER INFORMATION: Hu-2_VL-CDR3

<400> SEQUENCE: 14

Thr Gln Ala Thr Gln Phe Pro Leu Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Hu-4_VH-CDR1

<400> SEQUENCE: 15

Gly Tyr Thr Phe Ser Ser Tyr Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Hu-4_VH-CDR2

<400> SEQUENCE: 16

Ile Ser Ala Tyr Ser Gly Asn Thr
1               5

<210> SEQ ID NO 17
<211> LENGTH: 13
<212> TYPE: PRT
<213> ORGANISM: Artificial Sequence
```

```
<220> FEATURE:
<223> OTHER INFORMATION: Hu-4_VH-CDR3

<400> SEQUENCE: 17

Ala Arg Ala Ser Ala Asn Trp Tyr Asp Tyr Phe Asp Pro
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Hu--4_VL-CDR1

<400> SEQUENCE: 18

Gln Thr Ile Gly Gly Ser
1               5

<210> SEQ ID NO 19
<211> LENGTH: 3
<212> TYPE: PRT
<213> ORGANISM: Artificial Sequence
<220> FEATURE:
<223> OTHER INFORMATION: Hu--4_VL-CDR2

<400> SEQUENCE: 19

Tyr Ala Ser
1

<210> SEQ ID NO 20
<211> LENGTH: 9
<212> TYPE: PRT
<213> ORGANISM: Artificial Sequence
<220> FEATURE:
<223> OTHER INFORMATION: Hu--4_VL-CDR3

<400> SEQUENCE: 20

His Gln Ser Ser Ile Leu Pro Tyr Thr
1               5

<210> SEQ ID NO 21
<211> LENGTH: 10
<212> TYPE: PRT
<213> ORGANISM: Artificial Sequence
<220> FEATURE:
<223> OTHER INFORMATION: Hu-5_VH-CDR1

<400> SEQUENCE: 21

Gly Gly Ser Ile Ser Ser Ser Ser Phe Tyr
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Hu-5_VH-CDR2

<400> SEQUENCE: 22

Ile Tyr Tyr Ser Gly Ser Thr
1               5

<210> SEQ ID NO 23
<211> LENGTH: 14
<212> TYPE: PRT
<213> ORGANISM: Artificial Sequence
<220> FEATURE:
```

<223> OTHER INFORMATION: Hu-5_VH-CDR3

<400> SEQUENCE: 23

Ala Arg His Gly Val Arg Gly Val Ile Pro His Phe Asp Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Hu-5_VL-CDR1

<400> SEQUENCE: 24

Ser Gly Ser Val Ser Thr Ile Tyr Tyr
1               5

<210> SEQ ID NO 25
<211> LENGTH: 3
<212> TYPE: PRT
<213> ORGANISM: Artificial Sequence
<220> FEATURE:
<223> OTHER INFORMATION: Hu-5_VL-CDR2

<400> SEQUENCE: 25

Ser Thr Asn
1

<210> SEQ ID NO 26
<211> LENGTH: 9
<212> TYPE: PRT
<213> ORGANISM: Artificial Sequence
<220> FEATURE:
<223> OTHER INFORMATION: Hu-5_VL-CDR3

<400> SEQUENCE: 26

Val Leu Phe Leu Gly Ser Gly Leu Val
1               5

<210> SEQ ID NO 27
<211> LENGTH: 8
<212> TYPE: PRT
<213> ORGANISM: Artificial Sequence
<220> FEATURE:
<223> OTHER INFORMATION: Hu-6_VH-CDR1

<400> SEQUENCE: 27

Gly Tyr Thr Phe Thr Tyr Tyr Gly
1               5

<210> SEQ ID NO 28
<211> LENGTH: 8
<212> TYPE: PRT
<213> ORGANISM: Artificial Sequence
<220> FEATURE:
<223> OTHER INFORMATION: Hu-6_VH-CDR2

<400> SEQUENCE: 28

Ile Ser Ala Tyr Asn Gly Asn Thr
1               5

<210> SEQ ID NO 29
<211> LENGTH: 13
<212> TYPE: PRT
<213> ORGANISM: Artificial Sequence
<220> FEATURE:
<223> OTHER INFORMATION: Hu-6_VH-CDR3

```
<400> SEQUENCE: 29

Val Thr Glu Asn Ile Asn Trp Arg Asp Ala Phe Asp Ile
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Hu-6_VL-CDR1

<400> SEQUENCE: 30

Gln Thr Ile Gly Ser Ser
1               5

<210> SEQ ID NO 31
<211> LENGTH: 3
<212> TYPE: PRT
<213> ORGANISM: Artificial Sequence
<220> FEATURE:
<223> OTHER INFORMATION: Hu-6_VL-CDR2

<400> SEQUENCE: 31

Tyr Ala Ser
1

<210> SEQ ID NO 32
<211> LENGTH: 9
<212> TYPE: PRT
<213> ORGANISM: Artificial Sequence
<220> FEATURE:
<223> OTHER INFORMATION: Hu-6_VL-CDR3

<400> SEQUENCE: 32

His Gln Ser Ser Ser Leu Pro Tyr Thr
1               5
```

ANTI-INTERLEUKIN-23 P19 ANTIBODIES AND METHODS OF USE THEREOF

CROSS-REFERENCE TO RELATED APPLICATIONS

This application claims priority under 35 U.S.C. § 119(e) from U.S. Provisional Application Ser. No. 62/951,231, filed Dec. 20, 2019, all of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 16, 2019, is named "122863-5002-US_NVRB-004-001_ST25.TXT" and is 13 kilobytes in size.

FIELD

The present disclosure generally relates to antibodies and antibody fragments thereof that bind the p19 subunit of interleukin-23. The antibodies are useful for the treatment of immune-mediated inflammatory disorders, autoimmune diseases, or cancer.

BACKGROUND

The interleukin-12 (IL-12) family of regulatory cytokines includes a unique group of cytokines (IL-12, IL-23, IL-27, IL-35, and IL-39) comprising covalently bonded heterodimeric subunits. The heterodimeric IL-12 family cytokine members consist of an α-chain (p19, p28 or p35) and a β-chain (p40 or Ebi3).

IL-23 is a heterodimeric cytokine comprising a unique p19 subunit linked with a p40 subunit which is shared with IL-12. The main sources of IL-23 are tissue-resident or recruited dendritic cells and macrophages. The biologic action of IL-23 is hypothesized to occur through a receptor complex which is composed of the following two parts: i.) IL-12Rβ1, a part in common with IL-12, and ii.) IL-23R, a part specific for IL-23.

Members of the IL-12 family of cytokines act as immunological playmakers by directing innate and adaptive immune responses. These regulatory cytokines act by inducing the development of T-cell subpopulations and altering the function and fate of many immune cell populations that direct adaptive immune responses to infection, inflammation and autoimmune disease outcomes. IL-12 and IL-23 are predominantly proinflammatory/prostimulatory cytokines that play roles in the development of Th1 and Th17 cells, respectively.

The functional IL-23 receptor is a heterodimer of the IL-12Rβ1 subunit, which is shared with the IL-12 receptor and partnered with the signaling chain IL-23R (p19 subunit binding). The receptor for IL-23 is constitutively associated with Janus kinase 2 (Jak2) and predominantly activates STAT3. Expression of the IL-23 receptor is detected primarily on memory T-cells and NK cells. Monocytes, macrophages and dendritic cells also express IL-23 receptor at low levels.

There is substantial evidence that IL-23 responsive cells are associated with autoimmune inflammatory diseases and cancer and that the modulation of IL-23 activity can provide promising therapies. In particular, abnormal regulation of IL-23 is associated with immune-mediated inflammatory diseases (IMIDs), such as psoriasis, psoriatic arthritis, Crohn's disease and ulcerative colitis. In addition, the balance of proinflammatory cytokines, including IL-23 and IL-12 plays a key role in shaping the development of antitumor or protumor immunity.

The IL-23/IL-12 pathways are implicated in the cellular mechanisms involved in the pathophysiology of multiple inflammatory diseases. Several therapeutic strategies have been designed to inhibit IL-23 activity and there is a continuing need for therapeutic agents that target the proinflammatory IL-23/IL-23 receptor signaling axis for treatment of immune-mediated inflammatory disorders. More specifically, there remains a need for selective IL-23p19 antagonist antibodies that bind with high affinity to the p19 subunit of IL-23, in particular, human IL-23, and do not bind to the p40 subunit of the related cytokine family member, IL-12.

SUMMARY

The present disclosure addresses the above need by providing antibodies and antibody fragments that bind to the cytokine p19 subunit of IL-23. The antibodies and antibody fragments are useful for the treatment of immune-mediated inflammatory diseases (IMIDs) (e.g., autoimmune diseases and inflammatory disorders), either alone (e.g., as a monotherapy) or in combination with other immunotherapeutic agents.

In some embodiments, the anti-IL-23p19 antibodies or antibody fragments thereof bind to the cytokine p19 subunit of human IL-23. In a further embodiment, the antibodies are fully human.

In some embodiments, the anti-IL-23p19 antibodies or antibody fragments thereof comprise a heavy chain variable region comprising CDR1: SEQ ID NO: 9, CDR2: SEQ ID NO: 10, and CDR3: SEQ ID NO: 11; and/or a light chain variable region comprising CDR1: SEQ ID NO: 12, CDR2: SEQ ID NO: 13, and CDR3: SEQ ID NO: 14.

In some embodiments, the anti-IL-23p19 antibodies or antibody fragments thereof comprise a heavy chain variable region comprising CDR1: SEQ ID NO: 15, CDR2: SEQ ID NO: 16, and CDR3: SEQ ID NO: 17; and/or a light chain variable region comprising CDR1: SEQ ID NO: 18, CDR2: SEQ ID NO: 19, and CDR3: SEQ ID NO: 20.

In some embodiments, the anti-IL-23p19 antibodies or antibody fragments thereof comprise a heavy chain variable region comprising CDR1: SEQ ID NO: 21, CDR2: SEQ ID NO: 22, and CDR3: SEQ ID NO: 23; and/or a light chain variable region comprising CDR1: SEQ ID NO: 24, CDR2: SEQ ID NO: 25, and CDR3: SEQ ID NO: 26.

In some embodiments, the anti-IL-23p19 antibodies or antibody fragments thereof comprise a heavy chain variable region comprising CDR1: SEQ ID NO: 27, CDR2: SEQ ID NO: 28, and CDR3: SEQ ID NO: 29; and/or a light chain variable region comprising CDR1: SEQ ID NO: 30, CDR2: SEQ ID NO: 31, and CDR3: SEQ ID NO: 32.

In some embodiments, the anti-IL-23p19 antibodies or antibody fragments thereof comprise a variable heavy chain sequence selected from the group consisting of SEQ ID NOs: 1, 3, 5, and 7.

In other embodiments, the anti-IL-23p19 antibodies or antibody fragments thereof comprise a variable light chain sequence selected from the group consisting of SEQ ID NOs: 2, 4, 6, and 8.

In other embodiments, the anti-IL-23p19 antibodies or antibody fragments thereof comprise a variable heavy chain sequence selected from the group consisting of SEQ ID NOs: 1, 3, 5, and 7, and a variable light chain sequence selected from the group consisting of SEQ ID NOs: 2, 4, 6, and 8.

In some embodiments, the anti-IL-23p19 antibody or antibody fragment comprises variable heavy chain and variable light chain sequences, selected from the following combinations:
- (a) a variable heavy chain sequence comprising SEQ ID NO: 1 and a variable light chain sequence comprising SEQ ID NO: 2;
- (b) a variable heavy chain sequence comprising SEQ ID NO: 3 and a variable light chain sequence comprising SEQ ID NO: 4;
- (c) a variable heavy chain sequence comprising SEQ ID NO: 5 and a variable light chain sequence comprising SEQ ID NO: 6; and
- (d) a variable heavy chain sequence comprising SEQ ID NO: 7 and a variable light chain sequence comprising SEQ ID NO: 8.

In some embodiments, the anti-IL-23p19 antibodies (e.g., antagonist antibodies) bind with high affinity to the p19 subunit of IL-23 and do not bind to the p40 subunit of the related cytokine family member, IL-12.

In some embodiments, the anti-IL-23p19 antibodies or antibody fragments thereof exhibit one or more of the following characteristics: (a) is specific for human IL-23p19 and has the ability to block IL-23 binding to its receptor (IL-23R); (b) inhibits, interferes with, or modulates IL-23p19 interaction with IL-23 receptor signal transduction; (c) inhibits STAT3 activation induced by IL-23 in DB cells; (d) inhibits IL-17 production induced by human IL-23 in mouse splenocytes; (e) inhibits IL-17 production induced by human IL-23 in activated human PBMC; (f) does not inhibit IL-23 interaction with IL-12Rβ1 signal transduction: (g) does not inhibit human IL-12 induced interferon gamma production in human activated T-cells (PBMC) (h) does not inhibit cynomolgus monkey IL-12 induced interferon gamma production in human activated T-cells (PBMC); and (i) inhibits skin inflammation induced by human IL-23 in a murine psoriasis-like model.

In one aspect, the disclosed antibodies and isolated antigen binding agents can be used to inhibit IL-23p19 induced IL-23 receptor signaling networks (e.g., of the inflammatory microenvironment that promote autoimmune diseases).

The anti-IL-23p19 antibodies or antibody fragments thereof may exhibit one or more of the following properties:
- (a) is specific for human IL-23p19 and has the ability to block IL-23 binding to its receptor IL-23 receptor (e.g., blocker);
- (b) inhibits, interferes with, or modulates IL-23/IL-23 receptor-mediated signal transduction;
- (c) blocks IL-23-induced STAT3 activation induced by IL-23 in DB cells;
- (d) inhibits IL-23-induced IL-17 production in mouse splenocytes;
- (e) inhibits IL-23-induced IL-17 production in human PBMC;
- (f) does not inhibit IL-23 interaction with IL-12Rβ1 signal transduction;
- (g) does not block human IL-12-induced interferon-7 production in human PBMC;
- (h) does not inhibit cynomolgus monkey IL-12-induced interferon gamma productions in human PBMC; and
- (i) inhibits IL-23-induced skin-inflammation in a murine psoriasis-like model.

In some embodiments, the anti-IL-23p19 antibodies or antibody fragments thereof comprise a combination of CDR sequences derived from a variable heavy chain sequence selected from the group consisting of SEQ ID NOs: 1, 3, 5, and 7, and a variable light chain sequence selected from the group consisting of SEQ ID NOs: 2, 4, 6, and 8.

In some embodiments, the anti-IL-23p19 antibodies and antibody fragments thereof comprise one or more heavy chain variable region CDRs disclosed in Table 1 and/or one or more light chain variable region CDRs disclosed in Table 2.

In some embodiments, the anti-IL-23p19 antibody or antibody fragment is a recombinant antibody (e.g., a chimeric antibody or a humanized antibody) and comprises six (6) CDRs, all derived from the VH or VL domain of a single anti-IL-23p19 antibody disclosed herein. For example, a binding agent may comprise all six of the CDR regions of the anti-IL-23p19 antibody designated Hu-2.18006B (for a human antibody). In a representative example an antibody or antibody fragment thereof may comprise the amino acid sequences of SEQ ID NOs: 9-11 and SEQ ID NOs: 12-14, representing the CDR1, CDR2 and CDR3 of the variable heavy chain region and the CDR1, CDR2 and CDR3 of the variable light chain region of the Hu-2.18006B antibody.

In some embodiments, the anti-IL-23p19 antibody is a full-length antibody.

In some embodiments, the anti-IL-23p19 antibody is an antibody fragment. In further embodiments, the antibody fragment is selected from the group consisting of: Fab, Fab', F(ab')2, Fd, Fv, scFv and scFv-Fc fragment, a single-chain antibody, a minibody, and a diabody.

In some embodiments, the anti-IL-23p19 antibody is a monoclonal antibody.

In some embodiments, the anti-IL-23p19 antibody is a human antibody. In some embodiments, the anti-IL-23p19 antibody is a murine antibody.

In some embodiments, the anti-IL-23p19 antibody is a chimeric antibody. In some embodiments, the anti-IL-23p19 antibody is a bispecific antibody. In some embodiments, the anti-IL-23p19 antibody is a humanized antibody.

The anti-IL-23p19 antibodies and antibody fragments thereof may be used for the treatment or prevention of an immune-mediated inflammatory disease (IMID), such as an autoimmune diseases or inflammatory disorders, or cancer. Such methods for the treatment or prevention of an IMID or cancer comprise administering a composition or formulation that comprises an anti-IL-23p19 antibody or antibody fragment thereof to a subject in need thereof. In a further embodiment, the anti-IL-23p19 antibody or antibody fragment thereof may be administered either alone (e.g., as a monotherapy) or in combination with other immunotherapeutic agent and/or a chemotherapy. The IMID may be selected from the group consisting of, psoriasis, psoriatic arthritis, inflammatory bowel diseases (e.g., ulcerative colitis or Crohn's disease) ankylosing spondylitis, systemic lupus erythematosus, hidradenitis suppurativa, atopic dermatitis, asthma and familial adenomatous polyposis (FAP).

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be FIGS. 1A-1D provide the amino acid sequences of the VH and VL domains of the anti-IL-23p19 antibodies and their respective CDR sequences. Sequence identifiers are provided and the CDRs are underlined in the context of the variable domain sequence.

FIGS. 2A, 2B, 2C, 2D and 2E show the binding profiles of the anti-IL-23p19 antibodies to human IL-23, a recombinant cytokine comprising human p19 and murine p40 subunits, human IL-12 and human p40 subunit, determined by BIAcore.

FIGS. 6A and 6B show inhibition of IL-23-induced IL-17 production by three representative anti-IL-23p19 antibodies in a mouse splenocyte assay (MSA).

FIGS. 11A, 11B, 11C and 11D provide graphics of the representation of the pathology scores (H&E staining of the frozen ear tissues) effects from two anti-IL-23p19 antibodies on day 8 after the treatment from the mice treated in the murine skin inflammation model presented in Example 7.

FIGS. 12A, 12B, 12C and 12D shows representative photos of hematoxylin and eosin (H&E) staining of frozen ear tissues collected on the last day of the in vivo study (day 8) from the mice treated in the murine skin inflammation model presented in Example 7.

DETAILED DESCRIPTION

Figure 2B:
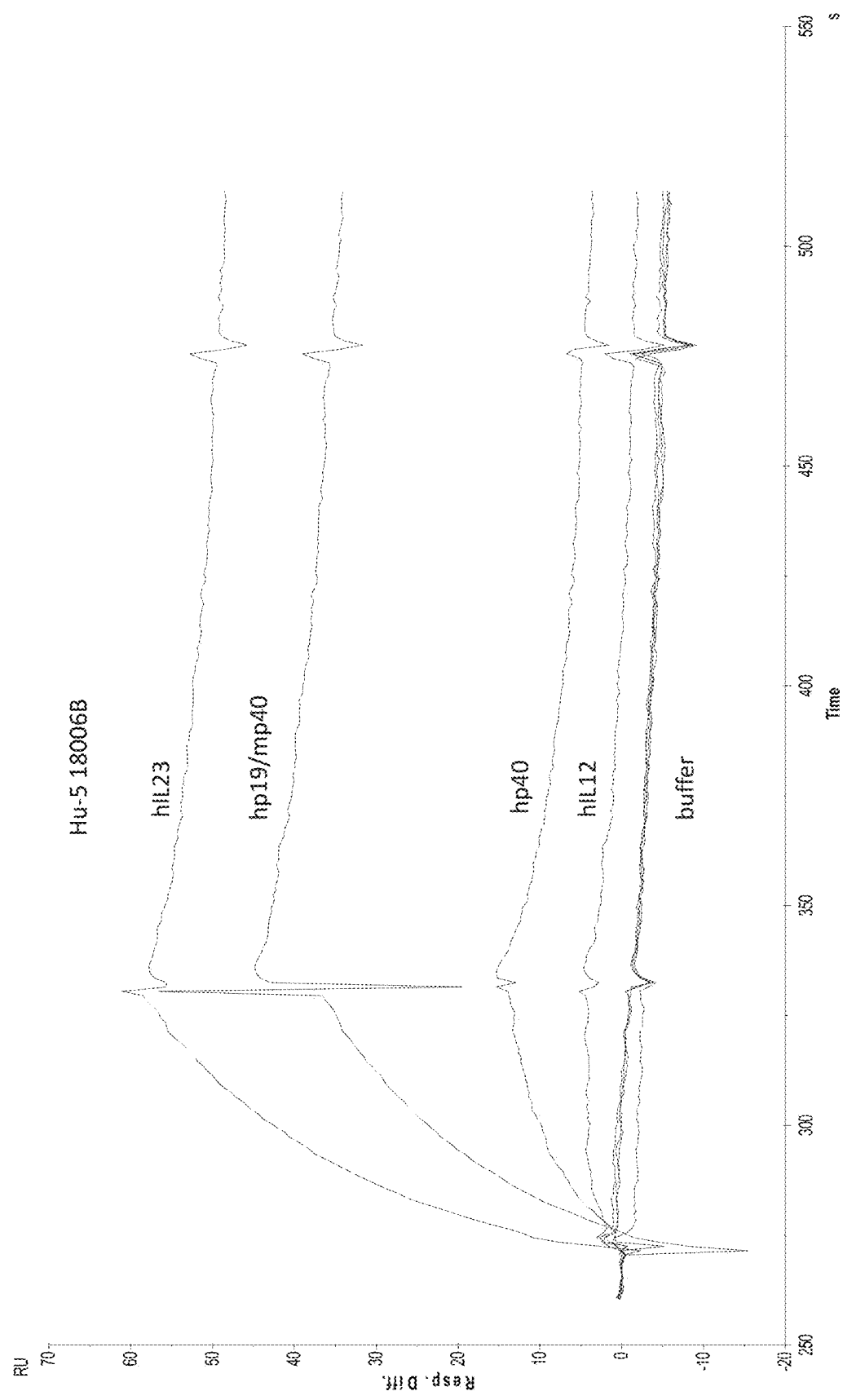

IL-23 is a pro-inflammatory heterodimeric cytokine that comprises a p19 submit and binds to an IL-23 receptor. Targeting the pro-inflammatory IL-23/IL-23 receptor signaling axis is an area of intense therapeutic exploration. The present disclosure provides antibodies and antibody fragments thereof that inhibit human IL-23/IL-23 receptor signaling axis and can be used for the treatment or prevention of IMIDs. Advantageously, the anti-IL-23p19 antibodies disclosed herein allow for complete inhibition of IL-23p19, result in lower dose formulations, result in less frequent and/or more effective dosing, and lead to reduced cost and increased efficiency.

The anti-IL-23p19 antibodies and antibody fragments thereof disclosed herein specifically bind to human IL-23p19 and antagonize the IL-23/IL-23 receptor signaling axis. In one aspect, the disclosed antibodies and antibody fragments thereof bind to human IL-23 with high affinity and prevent its interaction with the IL-23R, thereby blocking the downstream signaling cascade. In a particular aspect, the antibodies or antibody fragments thereof inhibit the IL-23 stimulated production of IL-17 from mouse splenocytes and from human PBMC. In another aspect, the antibodies or antibody fragments thereof do not bind to nor antagonize IL-12.

So that the disclosure may be more readily understood, certain technical and scientific terms are specifically defined below. Unless specifically defined elsewhere in this document, all other technical and scientific terms used herein have the meaning commonly understood by one of ordinary skill in the art to which this disclosure belongs.

Throughout this disclosure the following abbreviations will be used:

mAb or Mab or MAb—Monoclonal antibody.

CDR—Complementarity determining region in the immunoglobulin variable regions.

VH or VH—Immunoglobulin heavy chain variable region.

VL or VL—Immunoglobulin light chain variable region.

FR—Antibody framework region, the immunoglobulin variable regions excluding the CDR regions As used herein the term "interleukin-23" (used interchangeably with IL-23) refers to the human IL-23 heterodimer including, for example, a human IL-23 heterodimer comprising or consisting of a protein subunit having the amino acid sequence provided in UniProt entry UniProtKB-P29460 identified as IL-23 subunit (p40) disulfide-linked to a protein subunit having the amino acid sequence provided in UniProt entry UniProtKB-Q9NPF7 identified as Interleukin-23 subunit alpha (p19).

As used herein the term "IL-12R complex" and "IL-12R" refers to the high-affinity IL-12 cytokine receptor complex comprising the IL-12Rβ1 and IL-12Rβ2 subunits.

As used herein the term "IL-23R complex" and "IL-23R" refers to the high-affinity IL-23 cytokine receptor comprising the IL-12Rβ1 (in common with the IL-12R complex) and IL-23R subunits.

As used herein the term "interleukin-12" (used interchangeably throughout this disclosure with IL-12) refers to the human IL-12 heterodimer including, for example, a human IL-12 heterodimer comprising or consisting of a protein subunit having the amino acid sequence provided in UniProt entry UniProtKB-P29459 (identified as interleukin-12 subunit alpha disulfide-linked to a protein subunit comprising the amino acid sequence provided in UniProt entry UniProtKB-P29460 (identified as interleukin-12 subunit beta) (p40)). The term includes a heterodimeric protein comprising a 35 kD subunit (p35) and a 40 kD subunit (p40) which are both linked together with a disulfide bridge. The heterodimeric protein is referred to as a "p70 subunit". The structure of human IL-12 is described further in, for example, Kobayashi, et al. (1989) *J. Exp Med.* 170:827-845 and Ling, et al. (1995) *J. Exp Med.* 154:116-127). The term human IL-12 is intended to include recombinant human IL-12 (rh IL-12), which can be prepared by standard recombinant expression methods.

As used herein the term "interleukin 17" also referred to as "IL-17" or "IL-17A" is a 20-30 kD glycosylated homodimeric protein including, for example, a homodimeric protein comprising or consisting of a protein subunit having the amino acid sequence provided in UniProt entry UniProtKB-Q16552. The human IL-17 gene codes for a 155 amino acid protein that has a 19 amino acid signal sequence and a 136 amino acid mature segment. IL-17 is secreted by activated T-cells at sites of inflammation but is typically not present in the systemic circulation. IL-17 binds to a type I transmembrane receptor termed IL-17R which is a large ubiquitously expressed protein that demonstrates no significant sequence similarity to other known cytokine receptors. Human IL-17 shows amino acid sequence identity of 62.5% and 58% to the mouse and rat amino acid IL-17 sequences, respectively. Human IL-17 shows amino acid sequence identity of 97.4% to the cynomolgus monkey IL-17.

The term "antibody" herein is used in the broadest sense and encompasses various antibody structures, including but not limited to monoclonal antibodies, polyclonal antibodies, and multispecific antibodies (e.g., bispecific antibodies).

An exemplary antibody such as an IgG comprises two heavy chains and two light chains. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order: FR1, CDR1, FR2, CDR2, FR3, CDR3, FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) *J. Mol. Biol.* 196:901-917.

The term "monoclonal antibody" as used herein refers to an antibody obtained from a population of substantially homogeneous antibodies, e.g., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to a recombinant antibody in which a portion of the heavy and/or light chain is derived from a particular source or species, while the remainder of the heavy and/or light chain is derived from a different source or species.

A "human antibody" is an antibody that possesses an amino-acid sequence corresponding to that of an antibody produced by a human and/or has been made using any of the techniques for making human antibodies known to one of skill in the art. This definition of a human antibody specifically excludes a humanized antibody comprising non-human antigen-binding residues. Human antibodies can be produced using various techniques known in the art, including methods described in Cole et al, *Monoclonal Antibodies and Cancer Therapy*, Alan R. Liss, p. 77 (1985); Boerner et al, *J. Immunol*, 147(I):86-95 (1991). See also van Dijk and van de Winkel, *Curr. Opin. Pharmacol*, 5: 368-74 (2001). Human antibodies can be prepared by administering the antigen to a transgenic animal that has been modified to produce such antibodies in response to antigenic challenge, but whose endogenous loci have been disabled, e.g., immunized HuMab mice (see, e.g., Nils Lonberg et al., 1994, *Nature* 368:856-859, WO 98/24884, WO 94/25585, WO 93/1227, WO 92/22645, WO 92/03918 and WO 01/09187 regarding HuMab mice), xenomice (see, e.g., U.S. Pat. Nos. 6,075,181 and 6,150,584 regarding XENOMOUSE™ technology) or Trianni mice (see, e.g., WO 2013/063391, WO 2017/035252 and WO 2017/136734).

The term "humanized antibody" refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. Humanized antibodies are typically less immunogenic to humans, relative to non-humanized antibodies, and thus offer therapeutic benefits in certain situations. Those skilled in the art will be aware of humanized antibodies and will also be aware of suitable techniques for their generation. See for example, Hwang, W. Y. K., et al., *Methods* 36:35, 2005; Queen et al., *Proc. Natl. Acad. Sci. USA*, 86:10029-10033, 1989; Jones et al., *Nature*, 321:522-25, 1986; Riechmann et al., *Nature*, 332:323-27, 1988; Verhoeyen et al., *Science*, 239:1534-36, 1988; Orlandi et al., *Proc. Natl. Acad. Sci. USA*, 86:3833-37, 1989; U.S. Pat. Nos. 5,225,539; 5,530,101; 5,585,089; 5,693,761; 5,693,762; 6,180,370; and Selick et al., WO 90/07861, each of which is incorporated herein by reference in its entirety.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The terms "antigen-binding domain" of an antibody (or simply "binding domain") of an antibody or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) F(ab')2 fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) *Nature* 341: 544-546), which consist of a VH domain; (vi) isolated complementarity determining regions (CDR), and (vii) combinations of two or more isolated CDRs which may optionally be joined by a synthetic linker.

"Complementarity determining region" or "CDR" as the terms are used herein refer to short polypeptide sequences within the variable region of both heavy and light chain polypeptides that are primarily responsible for mediating specific antigen recognition. There are three CDRs (termed CDR1, CDR2, and CDR3) within each VL and each VH.

As will be appreciated by those in the art, the exact numbering and placement of the CDRs can be different among different numbering systems. However, it should be understood that the disclosure of a variable heavy and/or variable light sequence includes the disclosure of the associated CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

In certain embodiments, the CDRs of an antibody can be determined according to the IMGT numbering system as described in Lefranc M-P, (1999) *The Immunologist* 7: 132-136 and Lefranc M-P et al, (1999)*Nucleic Acids Res* 27: 209-212, each of which is herein incorporated by reference in its entirety. Unless stated otherwise herein, references to residue numbers in the variable domain of antibodies means residue numbering by the IMGT numbering system.

In other embodiments, the CDRs of an antibody can be determined according to MacCallum R M et al, (1996) *J Mol Biol* 262: 732-745, herein incorporated by reference in its entirety. See also, e.g. Martin A. "Protein Sequence and Structure Analysis of Antibody Variable Domains," in Antibody Engineering, Kontermann and Dübel, eds., Chapter 31, pp. 422-439, Springer-Verlag, Berlin (2001), herein incorporated by reference in its entirety. In other embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

"Framework" or "framework region" or "FR" refers to variable domain residues other than hypervariable region (HVR) residues. The FR of a variable domain generally consists of four FR domains: FR1, FR2, FR3, and FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), Vols. 1-3. In one embodiment, for the VL, the subgroup is subgroup kappa I as in Kabat et al., supra. In one embodiment, for the VH, the subgroup is subgroup Ill as in Kabat et al., supra.

The "hinge region" is generally defined as stretching from 216-238 (EU numbering) or 226-251 (Kabat numbering) of human IgG1. The hinge can be further divided into three distinct regions, the upper, middle (e.g., core), and lower hinge.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md. (1991).

A "blocking" antibody or an "antagonist" antibody is one which inhibits or reduces biological activity of the antigen it binds. Certain blocking antibodies or antagonist antibodies substantially or completely inhibit the biological activity of the antigen.

The term "Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent T-cell-mediated cytotoxicity (ADCC); phagocytosis; down-regulation of cell surface receptors (e.g., B-cell receptor); and B-cell activation.

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more. The amino acid residues of an antibody that contact an antigen can be determined, for example, by determining the crystal structure of the antibody in complex with the antigen or by performing hydrogen/deuterium exchange. In some embodiments, residues of an antibody that are within 5 Å the antigen are considered to contact the antigen. In some embodiments, an antibody that binds to the same epitope as a reference antibody blocks binding of the reference antibody to its antigen in a competition assay by 50% or more, and conversely, the reference antibody blocks binding of the antibody to its antigen in a competition assay by 50% or more.

The term "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab)$_2$; diabodies; linear antibodies; single-chain antibody molecules (e.g., scFv). Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large F(ab)$_2$ fragment which roughly corresponds to two disulfide linked Fab fragments having divalent antigen-binding activity and is still capable of cross-linking antigen. Fab fragments differ from Fab' fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The terms "antigen-binding domain" of an antibody (or simply "binding domain") of an antibody or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) *Nature* 341: 544-546), which consist of a VH domain; (vi) isolated complementarity determining regions (CDR), and (vii) combinations of two or more isolated CDRs which may optionally be joined by a synthetic linker.

The term "multispecific antibody" is used in the broadest sense and specifically covers an antibody comprising a heavy chain variable domain (VH) and a light chain variable domain (VL), where the VH-VL unit has polyepitopic specificity (e.g., is capable of binding to two different epitopes on one biological molecule or each epitope on a different biological molecule). Such multispecific antibodies include, but are not limited to, full-length antibodies, antibodies having two or more VL and VH domains, bispecific diabodies and triabodies. "Polyepitopic specificity" refers to the ability to specifically bind to two or more different epitopes on the same or different target(s).

"Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 µM, 3 µM to 0.001 µM, 1 µM to 0.001 µM, 0.5 µM to 0.001 µM or 0.1 µM to 0.001 µM. "Monospecific" refers to the ability to bind only one epitope. Multi-specific antibodies can have structures similar to full immunoglobulin molecules and include Fc regions, for example IgG Fc regions. Such structures can include, but are not limited to, IgG-Fv, IgG-(scFv)$_2$, DVD-Ig, (scFv)$_2$-(scFv)$_2$-Fc and (scFv)$_2$-Fc-(scFv)$_2$. In case of IgG-(scFv)$_2$, the scFv can be attached to either the N-terminal or the C-terminal end of either the heavy chain or the light chain.

As used herein, the term "bispecific antibodies" refers to monoclonal, often human or humanized, antibodies that have binding specificities for at least two different antigens. In the invention, one of the binding specificities can be directed towards IL-12 or IL-23, the other can be for any other antigen, e.g., for a cell-surface protein, receptor, receptor subunit, tissue-specific antigen, virally derived protein, virally encoded envelope protein, bacterially derived protein, or bacterial surface protein, etc.

As used herein, the term "diabodies" refers to bivalent antibodies comprising two polypeptide chains, in which each polypeptide chain includes VH and VL domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For a review of methods for assessment of antibody purity, see, for example, Flatman et al., *J. Chromatogr.* B 848:79-87 (2007). In a preferred embodiment, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively 10-10 M or lower, alternatively 10-11 M or lower, alternatively 10-12 M or lower or a Kd in the range of 10-4 M to 10-6 M or 10-6 M to 10-10 M or 10-7 M to 10-9 M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope. As used herein the terms "specific binding," "specifically binds," and "selectively binds," refer to antibody binding to an epitope of a human interleukin-23 p19.

The term "affinity," as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Methods for determining the affinity of mAbs can be found in Harlow, et al., *Antibodies: A Laboratory Manual*, Cold Spring Harbor Laboratory Press, Cold Spring Harbor, N.Y., 1988), Coligan et al., eds., *Current Protocols in Immunology*, Greene Publishing Assoc. and Wiley Interscience, N.Y., (1992, 1993), and Muller, *Meth. Enzymol.* 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

An "epitope" is a term of art that indicates the site or sites of interaction between an antibody and its antigen(s). As described by (Janeway, C, Jr., P. Travers, et al. (2001). Immunobiology: the immune system in health and disease. Part II, Section 3-8. New York, Garland Publishing, Inc.): "An antibody generally recognizes only a small region on the surface of a large molecule such as a protein . . . [Certain epitopes] are likely to be composed of amino acids from different parts of the [antigen] polypeptide chain that have been brought together by protein folding. Antigenic determinants of this kind are known as conformational or discontinuous epitopes because the structure recognized is composed of segments of the protein that are discontinuous in the amino acid sequence of the antigen but are brought together in the three-dimensional structure. In contrast, an epitope composed of a single segment of polypeptide chain is termed a continuous or linear epitope" (Janeway, C. Jr., P. Travers, et al. (2001). Immunobiology: the immune system in health and disease. Part II, Section 3-8. New York, Garland Publishing, Inc.).

The term "KD", as used herein, is intended to refer to the dissociation constant of a particular antibody-antigen interaction. It is calculated by the formula: Koff/Kon=KD The term "IC50", as used herein, is intended to refer to the effective concentration of antibody of the present invention needed to neutralize 50% of the bioactivity of IL-23 on human lymphoma DB cells in the bioassay described in Example 5: Inhibition of STAT3 activation in human DB cell Assay.

"EC50" with respect to an agent and a particular activity (e.g. binding to a cell, inhibition of enzymatic activity, activation or inhibition of an immune cell), refers to the efficient concentration of the agent which produces 50% of its maximum response or effect with respect to such activity. "EC100" with respect to an agent and a particular activity refers to the efficient concentration of the agent which produces its substantially maximum response with respect to such activity.

As used herein the term "antibody-based immunotherapy" and "immunotherapy" are used to broadly refer to any form of therapy that relies on the targeting specificity of an anti-IL-23p19 antibody, bispecific molecule, multi-specific molecule, binding agent, or fusion protein comprising an IL-23p19 specific binding agent, to mediate a direct or indirect effect on a cell characterized by aberrant expression of IL-23p19. The terms are meant to encompass methods of treatment using naked antibodies, bispecific antibodies (including T-cell engaging, NK cell engaging and other immune cell/effector cell engaging formats), antibody drug conjugates, cellular therapies using T-cells (CAR-T) or NK cells (CAR-NK) engineered to comprise an IL-23p19-specific chimeric antigen receptor, and oncolytic viruses comprising an IL-23p19 specific binding agent, and gene therapies by delivering the antigen binding sequences of the anti-IL-23p19 antibodies and express the corresponding antibody fragments in vivo.

As used herein, the term "immune-mediated inflammatory diseases" or "IMIDs" includes a group of seemingly unrelated diseases that share common inflammatory pathways and are triggered by or result in the dysregulation of innate and adaptive immune system functions. These conditions include, but are not limited to, psoriasis, rheumatoid arthritis, inflammatory bowel diseases, systemic lupus erythematosus, ankylosing spondylitis, hidradenitis suppurativa, atopic dermatitis and asthma. Any organ system may be inflicted by an IMID, and individuals may encounter a considerable reduction in quality of life, significant morbidity, and reduced lifespan (Bunte, K and Beikler, T, *Int. J. Mol. Sci.*, 20: 3394 (2019)). It is noted here that, as used in this specification and the appended claims, the singular forms "a," "an," and "the" include plural reference unless the context clearly dictates otherwise.

IL-12/IL-23 Receptor Signaling Axis

The p19 subunit of IL-23 (also referred to herein as "IL-23p19" and "p19 subunit") is a 189 amino acid polypeptide containing a 21 amino acid leader sequence (Oppmann et al. *Immunity* 13:715 (2000)). The biological activity of the p19 subunit is only detected when it is partnered with the IL-12 p40 subunit to form IL-23. Both IL-12 and IL-23 exist only as secreted heterodimeric cytokines and neither the IL-12 p35 nor the IL-23p19 subunit are secreted without intracellular covalent association with p40. The p40 subunit shared by the IL-12 and IL-23 cytokines bind the common IL-12Rβ1 component of their receptors, with signaling specificity being determined by the unique p35 (Il-12) and p19 (IL-23) subunits that bind the IL-12Rβ2 and IL-23R components of their respective high-affinity receptors. The interactions of IL-12 and IL-23 with their cognate receptors form part of a complicated regulatory network that coordinates innate and adaptive immune responses.

It is hypothesized that IL-12 plays a critical role in the development of protective immune responses to many intracellular pathogens and viruses and in tumor immune surveillance. See Kastelein, et al., *Annual Review of Immunology*, 2007, 25: 221-42; Liu, et al., Rheumatology, 2007, 46(8): 1266-73; Bowman et al., *Current Opinion in Infectious Diseases*, 2006 19:245-52; Fieschi and Casanova, *Eur. J. Immunol.* 2003 33:1461-4; Meeran et al., *Mol. Cancer. Ther.* 2006 5: 825-32; Langowski et al., *Nature* 2006 442: 461-5. As such, IL-23 specific inhibition (sparing IL-12 or the shared p40 subunit) may have a potentially superior safety profile compared to dual inhibition of IL-12 and IL-23.

The receptor for IL-23 comprises the IL-12Rβ1 subunit, shared in common with the IL-12 receptor, partnered with a unique subunit called IL-23R (Parham et al. *J. Immunol.* 168:5699 (2002)). It has been reported that IL-23R binds to IL-23 with a high affinity (KD=44±3 nM). In contrast, IL-23 binds to IL-12Rβ1 subunit with a lower affinity (KD=2±1 uM). Binding of IL-23R to IL-23 facilitates IL-12Rβ1 binding to IL-23 with a very high affinity (KD=25±5 nM) (Bloch et al, *Immunity,* 48, 45-58 (2018). The IL-23R is expressed by a great range of cells (natural killer cells, macrophages, dendritic cells, memory T-cells, keratinocytes). IL-23 production induces expression of IL-23R creating a positive feedback loop that enhances IL-23 expression.

IL-23 is produced by activated antigen presenting cells and binds to IL-23 receptor complexes expressed on NK cells and T-cells. IL-23, alone or in combination with other cytokines (e.g., IL-1β), has been shown to promote the production of IL-17A, IL-17F, IL-6 and tumor necrosis factor α (TNFα), which are proinflammatory cytokines known to contribute to inflammatory responses in IMID disorders.

Binding of IL-23p19 to IL-23R results in a restructuring process of the IL-23p19 helical domain, which enables binding of IL-12 p40 to IL-12Rβ1 (Bloch, Y et al. *Immunity.* 2018; 48(1):45-58). This process activates JAK2 and TYK2, leading to STAT3 and STAT4 formation, which ultimately function as transcription factors (Parham, C. et al., *Immunol.* 168(11):5699-5708 (2002). IL-23 is a key player in the late stage of differentiation of naive CD4+ T-cells into Th17 cells (Gaffen, S L et al., *Nat Rev Immunol.* 14(9):585-600 (2014). Being devoid of IL-23R, naive T-cells require other cytokines, such as transforming growth factor (TGF)-β and IL-6, to modulate the early stage of differentiation. These cytokines induce expression of retinoic acid receptor-related orphan receptor-γt as the transcription factor, which promotes expression of IL-23R. Immature Th17 cells induced by TGF-β and IL-6 require exposure to IL-23 to attain pathogenicity. Once matured, Th17 cells are capable of producing IL-17 and TNF-α (Kashani, A et al., *Gastroenterology & Hepatology* 15(5):255-265 (2019).

Despite the structural similarity between the two cytokines, the biological activities/functions of IL-23 are distinct from those of IL-12. IL-23 supports the differentiation and maintenance of naive CD4+ T-cells into a novel subset of cells called Th17 cells, which are distinct from the classical Th1 and Th2 cells. Th17 cells produce interleukin-17A (IL-17A) and interleukin-17F (IL-17F). Th17 cells produce a range of other factors known to drive inflammatory responses, including tumor necrosis factors known to drive inflammatory responses, including tumor necrosis factor alpha (TNF-α), interleukin-6 (IL-6), granulocyte-macrophage colony-stimulating factor (GM-CSF), CXCL1 and CCL20. NK cells and innate lymphoid cells such as lymphoid tissue induce (LTi)-like cells express IL-23 receptor and retinoic-acid-related orphan receptor (ROR) gamma and produce IL-17 in response to IL-23. IL-1β and IL-23 also co-stimulate gamma-delta T-cells to induce IL-17 production without T-cell receptor engagement.

Significantly, IL-23 maintains the differentiation and expansion of naïve T-cells into the distinct Th17 cell lineage. In the absence of IL-23, the Th17 phenotype is lost. IL-23 has been described as the "master regulator" of the immune-inflammatory response in IMIDs due to its critical role in maintaining the cytotoxic Th17 cells that produce pro-inflammatory cytokine profile. The pathogenicity of IL-23 depends in part on the dysregulated production of IL-17A, IL-17F and IL-22, providing a rationale for targeting the IL-23/IL-23R axis for immunotherapy.

Targeting the Pro-Inflammatory IL-23/IL-23 Receptor Signaling Axis

Anti-IL-12/IL-23 antibodies that have been reported to confer a therapeutic benefit in vivo include antibodies ustekinumab (CNTO1275) and briakinumab (ABT-874). Both antibodies target the common IL-12 p40 subunit in a region of the p40 subunit that is crucial for IL-12Rβ1 binding (Clarke, A. et al. mAbs 2(5):539-549 (2010).

Anti-IL-23 selective antibodies that have reported to confer a therapeutic benefit in vivo include guselkumab (TREMFYA®), tildrakizumab (ILUMYA®), risankizumab (SKYRIZI®), brazikumab (MEDI2070) and mirakizumab (Ly3074828); all of which are specific for the p19 subunit of IL-23. Data from randomized, placebo- and active-controlled phase 3 clinical trials show tildrakizumab, guselkumab and risankizumab to have a favorable risk-benefit profile in patients with moderate to severe psoriasis. No significant safety concerns have been observed for any of these IL-23p19 inhibitors.

Th1 cells driven by IL-12 were previously thought to be the pathogenic T-cell subset in many autoimmune diseases, however, more recent animal studies in models of inflammatory bowel disease, psoriasis, inflammatory arthritis and multiple sclerosis, in which the individual contributions of IL-12 versus IL-23 were evaluated have established that IL-23, not IL-12, is the key driver in autoimmune/inflammatory disease (Ahern et al., *Immun. Rev.* 226:147-159 (2008); Cua et al., *Nature* 421:744-748 (2003); Yago et al., *Arthritis Res and Ther.* 9(5): R96 (2007).

The role of IL-23 in immune-mediated inflammatory responses is also supported by genetic studies. Genome-wide association study (GWAS) linked IL-23R polymorphisms with predisposition to autoimmune conditions such as psoriasis and psoriatic arthritis (Liu et al., *PLoS Genet.* 4(3)e1000041 (2008), Reveille, et al., *Nat. Genet.* 42(2): 123-127 (2010), and Duerr et al., *Science* 314(5804):1461-1463 (2006). An association between rs11209026, a single-nucleotide polymorphism (SNP) in the IL-23R gene, and CD has been established (Reveille, J D et al.). This variant is shown to be protective against CD and UC. The protective characteristic of rs11209026 was confirmed in a meta-analysis that showed that carriage of this SNP variant reduced disease risk in a cohort of more than 75,000 cases and controls (Jostins, L. *Nature* 491(7422):119-124 (2012). This SNP variant, along with a few other coding variants of IL-23R, leads to a decrease in the expression of IL-23R, thus reducing the immune responses mediated through the IL-23 axis (*J Biol Chem.* 291(16):8673-8685 (2016).

While cytokines such as IL-6 and TGF-β1 can promote the differentiation of RORγt+Th17 cells from naïve CD4+ T-cells, IL-23 is required for the full inflammatory function of these cells. In addition, the binding of IL-23 to its receptor on activated RORγt+Th17 cells induces further expression of the IL-23 receptor (IL-23R), thus providing a feed-forward loop for the maintenance and propagation of these cells (Singh, S, et al., *MAbs* 7(4):1493-1503 (2015).

There is strong evidence that the IL-23/IL-17 axis plays an important role in the development of chronic inflammation, and genetic studies have revealed a potential link between the IL-23 receptor (IL-23R) or its ligand and several inflammatory diseases, including psoriasis, inflammatory bowel disease, and graft-versus-host disease. Targeting the IL-23/IL-17 axis is an area of intense therapeutic exploration in IMIDs, including psoriasis, psoriatic arthritis, inflammatory bowel diseases (ulcerative colitis and Crohns' disease), ankylosing spondylitis, and systemic lupus erythematosus (SLE).

Generally speaking, IL-23 specific antibodies, such as guselkumab, tildrakizumab, risankizumab, brazikumab or mirakizumab, selectively binds to IL-23p19 and inhibit binding of IL-23 to its receptor; thereby antagonizing the action of IL-23 to induce and sustain T helper (Th) 17 cells, innate lymphoid cells, γδT-cells, and natural killer (NK) cells responsible for tissue inflammation, destruction and/or aberrant tissue repair associated with an IMID.

Plaque psoriasis or psoriasis (PsO) is a chronic inflammatory, T-cell-mediated skin disorder that is characterized by a complex pathophysiology. The incidence of its occurrence in developed countries is 1-4%. Psoriasis is the most prevalent autoimmune disease in the United States where it affects approximately 7.5 million people. Plaque psoriasis is the most common form of psoriasis, affecting 80% to 90% of patients. Although the pathogenesis of psoriasis is not completely understood, multiple environmental factors, T-cells, dendritic cells, numerous cytokines, and 45 identified gene loci all interact to create the systemic psoriatic disease state and ultimately psoriatic plaques (Nestle F O, et al., *N Engl J Med.* 361(5):496-509 (2009), Mahil S K, et al *Dermatol Clin.* 33(1):1-11 (2015). A synergistic influence of genetic and environmental factors along with the interplay of innate and adaptive immunity eventually leads to the abnormal keratinocyte proliferation and formation of the psoriatic lesions (Chan, J. R, et al., *J. Exp. Med,* 203(12) 2577-2587 (2006).

PsO plaques are typically well-demarcated erythematous, scaly skin lesions characterized by epidermal thickening. Affected keratinocytes activate dendritic cells, travel to local lymph nodes and release several cytokines including interleukin IL-12 and IL-23, which activate type 1 T helper (Th1) and type 17 T helper (Th17) cells, respectively. T lymphocytes and other cell types release additional cytokines, including tumor necrosis factor (TNF)-α, IL-22, and IL-17, leading to increased keratinocyte activation and the initiation of a self-propelled cycle of inflammation (Lowes M A et al., *Trends Immunol.* 34(4):174-81 (2013)). Histologically, there is a marked epidermal hyperplasia accompanied by parakeratosis and a mixed dermal infiltrate, including CD4+ T-cells, dendritic cells, macrophages and mast cells.

Early publications reported the presence of elevated levels of tumor necrosis factor-α α and the p40 subunit of IL-12, accompanied by the overexpression of IL-12 p40 and IL-23 p40 messenger RNA in psoriatic skin lesions. These findings suggested that the inhibition of IL-12 and IL-23 with a neutralizing antibody to the IL-12/23 p40 subunit protein may offer an effective therapeutic approach for the treatment of psoriasis (Piskin G, et al., *J Immunol* 2006, 176: 1908-15). Psoriasis was initially deemed to be a Th-1 mediated disease (based on the cytokine secretory profile characteristic of T helper 1-type cells: interleukin-2, tumor necrosis factor (TNF)-α, and interferon (IFN)-γ).

The basic role of IL-23 in the pathogenesis of psoriasis has been clarified, and it is associated with the biology of the Th17 lineage. The initial differentiation of naïve T lymphocytes to Th17 requires the presence of TGF-β1, IL-6, and IL-1, while IL-23 is necessary for the activation and maintenance of Th17 in order to secrete the pro-inflammatory cytokines IL-17, IL-22, IL-21, and tumor necrosis factor-α, which eventually contributes to the formation of the psoriatic skin lesions (Fotaidou, C. et al., *Psoriasis: Targets and Therapy* 8: 1-5 (2018)).

Therefore, although IL-12 and IL-23 are both known to contribute to the development of Th1 immune responses in psoriasis, IL-23 is now recognized as the key driver of Th17 cell differentiation and survival. The primary cytokines produced by Th17 cells are those of the pro-inflammatory IL-17 family, including IL-17A, IL-17B, IL-17C, IL-17D, IL-17E, and IL-17F. IL-17A and IL-17F are similar and bind to the same IL-17 receptor, a heterodimer comprised of an IL-17RA and an IL-17RC subunits.

Although early therapeutic strategies targeted Th1 cells as the central cell type for psoriasis pathogenesis, newer models focus on the IL-23/Th17 axis (Lowes M A, et al. *Trends Immunol.* 34(4):174-81(2013). The rationale for the new focus is premised on the belief that IL-17 is a key player in the pathogenesis of is psoriasis and the knowledge that IL-23 drives Th17 cell activation. Moreover, IL-23 stimulates production of other Th17 cytokines (e.g., IL-22) by other cell types, including innate lymphoid type 3 cells and γδ T-cells (Ward, N. L., *J Investig Dermatol.* 134: 2305-2307 (2014). It has been suggested that inhibition of IL-23 will block downstream production of IL-17A and IL-22 by Th17 cells and that the effect will translate into antagonism of psoriasis immunopathogenesis.

The IL-23/IL-17 axis is currently considered to be crucial in the pathogenesis of psoriasis and selective IL-23p19 inhibition may bring several advantages with respect to IL-12/23 p40 inhibition, or distal blockade of IL-17A or its receptor (Torres, T *Drugs* 77:1493-1503 (2017). To date, three IL-23p19-subunit specific monoclonal antibodies (i.e., guselkumab, tildrakizumab and risankizumab) have received approval from the United States Food and Drug Administration (FDA) and the European Medicines Agency (EMA) for the treatment of moderate-to-severe plaque psoriasis in adults who are candidates for systemic therapy or phototherapy. In July 2020 guselkumab was also approved for the treatment of adults with active psoriatic arthritis by the FDA.

The high efficacy of IL-23 blockade in psoriasis was demonstrated in early proof-of-concept testing and phase I clinical trials. A phase 1 study showed that a single dose of guselkumab resulted in significant clinical responses in patients with moderate-to-severe plaque psoriasis (Sofen H, et al., *J Allergy Clin Immunol;* 133:1032-1040 (2014). The Phase I study also reported that selective antagonism of interleukin-23 with guselkumab resulted in clinical improvement of psoriasis, characterized by reductions in epidermal thickness, T-cell and dendritic-cell infiltration, expression of genes associated with psoriasis, and serum IL-17A levels. The reported finding of a measurable clinical responses in patients with moderate-to-severe psoriasis, after a single dose of guselkumab supported the emerging theory that selective neutralization of IL-23 was a promising therapeutic option.

A rapid onset of guselkumab activity was also observed in a Phase II dosing study (NCT01483599) evaluating the use of guselkumab at a broad range of doses and two different dosing intervals for up to 40 weeks of continuous treatment. Efficacy was evident at the earliest assessment (week 4). Several of the guselkumab regimens were associated with considerably better response rates than those associated with adalimumab, a biologic agent that is commonly used to treat psoriasis (Gordon, K B et al., *N Engl J Med* 373:136-144 (2015). The efficacy of guselkumab continued to increase beyond week 16 (primary end-point assessment) and was maintained through week 40. Moreover, the majority of patients in the 100-mg guselkumab group had completely cleared psoriasis, as indicated by a PGA score of 0 (in 62% of patients) and a 100% improvement from baseline in PASI score (in 54% of patients) after 40 weeks of continuous treatment. Regulatory approval by the FDA and EMA relied in part on the findings of three pivotal phase III clinical trials VOYAGE 1, (Blauvelt, A et al. *J. Am. Acad. Dermatol.* 76: 405-417 (2017) VOYAGE (Reich, K et al. *J Am. Acad. Dermatol.*, 76: 418-431 (2017) and NAVIGATE (Langley, R G et al., *Brit. J. Dermatol.* 178:114-123 (2017).

VOYAGE 1 (NCT02207231) was a phase III, randomized, double-blind, placebo- and active comparator-controlled trial conducted at 101 global sites (December 2014-April 2016). The study comprised an active-comparator period when guselkumab was compared with adalimumab (week 0-48) and a placebo-controlled period (weeks 0-16), after which patients taking placebo crossed over to receive guselkumab through week 48. Guselkumab was superior to placebo and/or adalimumab for the coprimary end points and all major secondary end points (all P<0.001). Compared with placebo, significantly higher proportions of patients taking guselkumab achieved IGA 0/1 (6.9% vs 85.1%) and PASI 90 (2.9% vs 73.3%) at week 16. Likewise, PASI 100 responses in the guselkumab group were significantly better than those in the adalimumab group at weeks 24 and 48 (P<0.001). After initiating guselkumab at week 16, patients in the placebo cross-over group achieved responses similar to those observed in the guselkumab group. VOYAGE 1 confirms the role of IL-23 in the pathogenesis of psoriasis. When compared with TNF-α blockade, selective targeting of the IL-23 pathway provides more psoriasis-specific cytokine inhibition with a higher degree of efficacy while maintaining a favorable safety profile (Blauvelt, A, et al., *J Investig Dermatol.*, 135: 1946-1953 (2015).

VOYAGE 1 was an extended-label trial that followed patients for four years after the initial trial. The patients were initially randomized to receive either Tremfya or placebo, but at 16 weeks everyone received Tremfya. The VOYAGE 1 study found that 82% of patients receiving Tremfya in a combined group of individuals that initially received Tremfya or placebo then crossed over to Tremfya at week 16 showed at least a 90% improvement in the Psoriasis Area Severity Index (PASI 90) and an Investigator's Global Assessment (IGA) score of cleared (0) or minimal disease (1) at week 204, which is four years.

Psoriatic arthritis (PsA) is a chronic inflammatory musculoskeletal disease that occurs in up to 40% of patients with psoriasis. Consequently, PsA can be considered as a disease within a disease, sharing many common pathogenic pathways with psoriasis. Psoriasis usually precedes PsA in 70% of patients, with inflammatory skin and joint disease occurring simultaneously in 15% of patients and the inflammatory arthritis occurring before the dermatosis in the remaining patients Eventually, almost all patients with PsA will develop psoriasis, however the clinical presentation and course of PsA is quite heterogeneous and five distinct patterns of PsA based on the distribution of afflicted joints have been described (Dobbin-Sears, I et al. *Ther Adv Chronic Dis*, 9(10) 191-198 (2018)).

PsA is a heterogeneous condition with articular and extra-articular manifestations, including a combination of peripheral arthritis, axial disease, enthesitis, dactylitis and skin and nail disease (Quireo, R and Coto-Sequra, P, *Expert Opinion On Biological Therapy*, 18:9, 931-935 (2018)). Genetic, immunologic and environmental factors activating both the innate and acquired immune response appear to have an important role in the pathogenesis of PsA. With disease evolution, patients may exhibit multiple patterns and are not limited to one subset of arthritis. Approximately two-thirds of PsA patients will experience progressive joint damage that is often associated with functional loss and disability.

The pro-inflammatory IL-23/IL-23 receptor signaling axis is implicated in both PsO and PsA. In particular, the Th-17 axis (inhibited by IL-23) is considered to play an important role in the immunopathogenesis of both psoriasis and PsA. The IL-23/IL-23-R interaction induces IL-23-dependent differentiation and activation of Th-17 cells, and the production and secretion of IL-17 and IL-22 culminating in synovium and skin inflammation as well as bone remodeling. Of particular relevance to PsA pathology, IL-17 promotes bone erosion through the upregulation of RANKL. Integrated data analysis results indicated that ustekinumab-treated patients (regardless of dose) significantly inhibited radiographic progression of joint damage in patients with active PsA (Kavanaugh, A et al. *Ann. Rheum. Dis.* 73(6):1000-1006 (2014). This supports the roles of IL-23 and the downstream Th17 pathway in the radiographic damage that occurs in most PsA patients.

Crohn's disease (CD) and ulcerative colitis (UC), the major inflammatory bowel diseases (IBD) in humans, are both chronically relapsing diseases characterized by a chronic tissue inflammation that alters the integrity and function of the gut. Increased levels of interleukin (IL)-23 and T helper (Th) 17 cell cytokines have been found in intestinal mucosa, plasma, and serum of patients with inflammatory bowel disease (IBD) (e.g., Crohn's disease (CD) and ulcerative colitis (UC)).

Variants in several genes encoding for elements of the IL-23 and IL-17 cellular pathways are associated with IBD risk. In particular, a loss-of-function variant of the IL-23 receptor gene that encodes an amino acid change from arginine to glutamine at position 381, has been observed to reduce the risk for IBD, attributed to decreased STAT3 signaling and diminished Th17 cell responses upon exposure to IL-23 (Barrett, J C et al. *Nat. Genet.* 40:955-962 (2008), Duerr, R H et al. *Science* 314:1461-1463 (2006), Allocca, M et al. *Best Practice & Res. Clin.* Gastro. 32-33:95-102 (2018).

Crohn's disease (CD) is a chronic immune-mediated condition that is characterized by a relapsing nature and involvement of the gastrointestinal system. CD is characterized by a dysregulation of both innate and adaptive immune responses. Although the pathophysiologic mechanisms have not been completely understood, the disease is likely a result of the interaction between commensal flora in the gut and host microbial defenses in a genetically predisposed individual, resulting in a transmural inflammatory response in Crohn's disease (Deepak, P and Loftus, E, Drug Design, *Development and Therapy* (10) 3685-3698) (2016). Over the long term, the persistent transmural inflammatory response often leads to the development of strictures and/or fistulas that require hospitalization and/or surgery. After the discovery of the IL-23/IL-17 pathways the treatment paradigm for CD shifted away from nonspecific immunosuppressive therapies (i.e., methotrexate) toward immunotherapy targeting the IL-2 and/or/IL-17 pathways.

UC is a chronic, relapsing-remitting, inflammatory bowel disease, that causes continuous mucosal inflammation of the large intestine which develops tiny open sores or ulcers that produce pus and mucous. It is estimated that close to 1 million patients with ulcerative colitis live in the United States and that UC affects 2.6 million people in Europe. The disease is more common among Caucasian people, although it can affect people of any racial or ethnic group and men are more likely than women to be diagnosed. The etiology of UC is poorly understood, but is believed to be partially attributed to an aberrant immune response to microbiota (microbial flora and pathogens) in subjects with a genetic predisposition leading to chronic inflammation in the colon. Ulcerative colitis is known to exhibit a Th2-type cytokine profile.

IL-23-specific p19 antagonists under clinical investigation for IBD include brazikumab (MEDI2070), risankizumab (BI 655066), mirikizumab (LY3074828), and guselkumab (Tremfya, Janssen). To date the anti-p19 (anti-IL-23) antibodies, brazikumab and risankizumab have been reported to be effective in moderate to severe CD in phase II trials.

In a phase II trial, mirikizumab, was recently shown be effective for moderate to severe UC. Across all doses studied, between 11.5 percent to 22.6 percent of patients treated with mirikizumab achieved clinical remission, compared to 4.8 percent of those treated with placebo. Additionally, greater proportions of patients treated with mirikizumab achieved endoscopic remission and symptomatic remission compared to placebo at 12 weeks. Currently there are no p-19 selective antibodies approved for the treatment of IBDs. Phase 2 and 3 clinical trials of anti-p19 agents (risankizumab, brazikumab, guselkumab) are ongoing and will provide further information not only on their efficacy and safety per se, but also on head-to-head efficacy compared to existing biologics and on the evolving therapeutic concept of combination treatment with multiple biologics.

Ankylosing spondylitis (AS), like psoriatic arthritis, is another spondyloarthropathy genetically associated with the IL-23 pathway; it is a painful condition involving spinal inflammation that can lead to irreversible spinal fusion. AS is generally unresponsive to conventional disease-modifying antirheumatic drugs (DMARDs), and systemic therapy for AS consists of non-steroidal anti-inflammatory drugs (NSAIDs) and tumor necrosis factor inhibitors.

Several lines of evidence have identified IL-23 as a promising therapeutic target in AS (Paine A, et al. *Curr. Opin. Rheumatol.* 28:359-67 (2016). At the genetic level, case-control genome-wide association studies have demonstrated that IL-23 receptor (IL-23R) polymorphisms are associated with an increased risk of developing AS (Reveille J D, et al *Genet* 42:123-7 (2010). In addition, a protective effect of the IL-23R R381Q polymorphism is observed in AS (Sarin R, et al. *Proc Natl Acad Sci USA;* 108:9560-58 (2011). Increased numbers of IL-23-producing cells have been found in facet joints of patients with AS (Appel H, et al. *Arthritis Rheum;* 65:1522-9 (2013), while the number of IL-23-responsive T helper (Th) 22 (Th22), Th17 and gamma/delta T-cells are elevated in blood from patients with AS (Zhang L, et al. *PLoS One* (7):e31000 (2012).

The recent approval of the IL-17A inhibitor, secukinumab, for the treatment of AS (Baeten D. et al., *N Engl. J. Med.* 373:2534-48 (2015), supported the clinical hypothesis that direct and specific inhibition of IL-23 would be of therapeutic benefit to patients with AS. However, a recent publication reporting the results of randomized, double-blind, placebo-controlled, proof-of-concept, dose-finding phase 2 study evaluating the efficacy of risankizumab in patients with active AS (NCT02047110), concluded that treatment with risankizumab did not meet the study primary endpoint and showed no evidence of clinically meaningful improvements compared with placebo in patients with active AS (Baeten D, et al., *Annals of the Rheumatic Diseases* 77: 1295-1302 (2018).

IL-23p19 Antagonists

The IL-23 receptor complex is comprised of IL-12Rβ1 partnered with the signaling chain IL-23R (p19 subunit binding). IL-23 mediates cellular activity through sequential binding to 2 receptor chains expressed as the IL-12Rβ1/IL-23R receptor complex on the surface of T-cells and natural killer (NK) cells.

Murine, humanized and phage display antibodies selected for inhibition of recombinant IL-23 have been described; see for example U.S. Pat. No. 7,491,391, WIPO Publications WO 1999/05280, WO 2007/0244846, WO 2007/027714, WO 2007/076524, WO 2007/147019, WO 2008/103473, WO 2008/103432, WO 2009/043933 and WO 2009/082624.

Monoclonal antibodies, or antigen binding domains thereof, that bind with high affinity to the p19 subunit of the IL-23 cytokine, can neutralize its activity and consequently block its downstream effects. To date, three (3) anti-p19 antibodies, guselkumab (TREMFYA®), tildrakizumab, (ILUMYA®), and risankizumab (SKYRIZI®) have been approved by the FDA for the treatment of IMIDs. Two other IL-23p19 subunit specific antibodies are currently in late-stage clinical development MEDI2070 (brazikumab, Astrazeneca/Medimmue) and Ly3074828 (mirikizumab, Eli Lilly). Mirikizumab is a humanized IgG4 monoclonal antibody. By blocking IL-23, anti-p19-specific antibodies inhibit the release of pro-inflammatory cytokines and chemokines thereby dampening the inflammatory response.

Since this group of IL-23 antagonists target the p19 subunit of IL-23 and not the p40 subunit, they do not affect IL-12 activity. This feature distinguishes the IL-23 receptor antagonists from ustekinumab (STELARA) which targets the common p40 subunit shared by IL-12 and IL-23. Despite the efficacy and favorable safety profile of ustekinumab, drug development for IMIDs has shifted its focus towards the development of agents that selectively antagonize the IL-23/IL-17 pathways.

Guselkumab (CNTO1959) is a fully human monoclonal IgG1, λ antibody that binds with high affinity to the p19 subunit of human IL-23. Guselkumab is the first FDA-approved anti-p19-specific antibody/IL-23 antagonist. It was approved on Jul. 13, 2017, for the treatment of adults with moderate-to-severe plaque psoriasis, after an expedited regulatory review. It has also been approved in Canada, the European Union, Japan and several other countries worldwide. Guselkumab is marketed by Janssen as TREMFYA (U.S. Pat. Nos. 7,935,344 and 7,993,645).

Guselkumab inhibits the bioactivity of human IL-23 by preventing IL-23 from binding to the IL-23 receptor protein expressed on the surface of immune cells. More specifically, guselkumab binds to the human IL-23 cytokine via the p19 subunit and prevents an IL-23-IL-23R complex formation and subsequent intracellular signaling of the partner receptor chains.

The TREMFYA® development program currently includes Phase III trials evaluating the efficacy of TREMFYA® for treating active psoriatic arthritis, a Phase IIb/III study in Crohn's disease, a Phase IIb/III trial in ulcerative colitis, and another clinical study evaluating guselkumab for Hidradenitis suppurativa.

Janssen recently announced plans to further expanded the clinical development of guselkumab into familial adenomatous polyposis (FAP), a disease of the gastrointestinal tract. Janssen has initiated a phase Ib proof-of-concept clinical trial (NCT03649971) that will evaluate the efficacy and safety of guselkumab vs. placebo in approximately 72 patients. FAP Syndrome is the most common adenomatous polyposis syndrome. It is an autosomal dominantly inherited disorder characterized by the early onset of hundreds to thousands of adenomatous polyps throughout the colon. FAP has a birth incidence of about 1 out of 8,300 worldwide, manifests equally in both sexes, and, if left untreated, patients with this syndrome will most likely develop colorectal cancer. In addition, an increased risk exists for the development of other malignancies. Removing the colon is currently the only way to prevent colorectal cancer from developing in these patients.

Tildrakizumab (MK322) is a is a humanized monoclonal IgG1, κ antibody marketed by Merck & Co./Sun Pharmaceutical as ILUMYA (U.S. Pat. No. 8,404,813). Tildrakizuab selectively binds to the p19 subunit, thereby inhibiting the interaction of IL-23 with its receptor, and thus inhibits the release of IL-23 mediated proinflammatory cytokines. It received its first global approval in March 2018 from the FDA for use in adult patients with moderate to severe plaque psoriasis.

Risankizumab (BI 655066) is a humanized monoclonal IgG1, κ marketed by AbbVie/Boehringer Ingelheim as SKYRIZI (U.S. Pat. No. 8,778,346). Risankizumab was developed as a high-affinity antibody antagonist of IL-23.

Risankizumab selectively binds, with high affinity (dissociation constant <10 pmol/L), to the p19 subunit of interleukin-23 (IL-23p19)(Singh, S, et al., *MAbs* 7(4)77-791 (2015). It selectively targets the p19 subunit of IL-23 and potently inhibits IL-23-induced (human IL-23 produced by THP-1 cells) IL-17 production in a mouse splenocyte assay with IC50 value of approximately 2 pM ((Singh, S, et al., *MAbs* 7(4)77-791 (2015). The framework region of risankizumab has been engineered with two mutations in the Fc region to reduce FcγR receptor and complement binding. More specifically, the Fc portion of risankizumab has two replacement mutations (Leu234Ala and Leu235Ala) to reduce Fcγ receptor and complement binding. Risankizumab was approved by the FDA for the treatment of moderate to severe plaque psoriasis in adults in April 2019.

Anti-IL-23p19 Antibodies

The anti-IL-23p19 antibodies of the disclosure bind to the p19 subunit of IL-23. Preferably, such antibodies are fully human and do not bind the p40 subunit of IL-12.

In an embodiment, the anti-IL-23p19 antibodies or antibody fragments thereof comprise a VH having a set of CDRs (HCDR1, HCDR2, and HCDR3) disclosed in Table 1. For example, the anti-IL-23p19 antibodies or antibody fragments thereof may comprise a set of CDRs corresponding to those CDRs in one or more of the anti-IL-23p19 antibodies disclosed in Table 1 (e.g., the CDRs of the Hu-2. 18006B antibody).

In another embodiment, the anti-IL-23p19 antibodies comprise a VL having a set of CDRs (LCDR1, LCDR2, and LCDR3) as disclosed in Table 2. For example, the anti-IL-23p19 antibodies or antibody fragments thereof may comprise a set of CDRs corresponding to those CDRs in one or more of the anti-IL-23p19 antibodies disclosed in Table 2 (e.g., the CDRs of the Hu-2. 18006B antibody).

In an alternative embodiment, the anti-IL-23p19 antibodies or antibody fragments thereof comprise a VH having a set of CDRs (HCDR1, HCDR2, and HCDR3) as disclosed in Table 1, and a VL having a set of CDRs (LCDR1, LCDR2, and LCDR3) as disclosed in Table 2.

TABLE 1

CDR Sequences of Human Variable Heavy Chain Domains

| Anti-IL-23p19 Ab | CDR1 | CDR2 | CDR3 |
|---|---|---|---|
| Hu-2. 18006B | SEQ ID NO: 9 | SEQ ID NO: 10 | SEQ ID NO: 11 |
| Hu-4. 18006B | SEQ ID NO: 15 | SEQ ID NO: 16 | SEQ ID NO: 17 |
| Hu-5. 18006B | SEQ ID NO: 21 | SEQ ID NO: 22 | SEQ ID NO: 23 |
| Hu-6. 18006B | SEQ ID NO: 27 | SEQ ID NO: 28 | SEQ ID NO: 29 |

TABLE 2

CDR Sequences of Human Variable Light Chain Domains

| Anti-IL-23p19 Ab | CDR1 | CDR2 | CDR3 |
|---|---|---|---|
| Hu-2. 18006B | SEQ ID NO: 12 | SEQ ID NO: 13 | SEQ ID NO: 14 |
| Hu-4. 18006B | SEQ ID NO: 18 | SEQ ID NO: 19 | SEQ ID NO: 20 |
| Hu-5. 18006B | SEQ ID NO: 24 | SEQ ID NO: 25 | SEQ ID NO: 26 |
| Hu-6. 18006B | SEQ ID NO: 30 | SEQ ID NO: 31 | SEQ ID NO: 32 |

In an embodiment, the antibody may be a monoclonal, chimeric, humanized or human antibody (or antigen-binding portions thereof) that specifically bind to human IL-23p19.

In an embodiment, the anti-IL-23p19 antibodies or antibody fragments thereof comprise a VH having a set of complementarity-determining regions (CDR1, CDR2, and CDR3) selected from the group consisting of:
  (i) CDR1: SEQ ID NO: 9, CDR2: SEQ ID NO: 10, CDR3: SEQ ID NO: 11;
  (ii) CDR1: SEQ ID NO: 15, CDR2: SEQ ID NO: 16, CDR3: SEQ ID NO: 17;
  (iii) CDR1: SEQ ID NO: 21, CDR2: SEQ ID NO: 22, CDR3: SEQ ID NO: 23; and
  (iv) CDR1: SEQ ID NO: 27, CDR2: SEQ ID NO: 28, CDR3: SEQ ID NO: 29.

In another embodiment, the anti-IL-23p19 antibodies or antibody fragments thereof comprise a VL having a set of complementarity-determining regions (CDR1, CDR2, and CDR3) selected from the group consisting of:
  (i) CDR1: SEQ ID NO: 12, CDR2: SEQ ID NO: 13, CDR3: SEQ ID NO: 14;
  (ii) CDR1: SEQ ID NO: 18, CDR2: SEQ ID NO: 19, CDR3: SEQ ID NO: 20;
  (iii) CDR1: SEQ ID NO: 24, CDR2: SEQ ID NO: 25, CDR3: SEQ ID NO: 26; and
  (iv) CDR1: SEQ ID NO: 30, CDR2: SEQ ID NO: 31, CDR3: SEQ ID NO: 32.

In another embodiment, the anti-IL-23p19 antibodies or antibody fragments thereof comprise:
  (a) a VH having a set of complementarity-determining regions (CDR1, CDR2, and CDR3) selected from the group consisting of:
    (i) CDR1: SEQ ID NO: 9, CDR2: SEQ ID NO: 10, CDR3: SEQ ID NO: 11;
    (ii) CDR1: SEQ ID NO: 15, CDR2: SEQ ID NO: 16, CDR3: SEQ ID NO: 17;
    (iii) CDR1: SEQ ID NO: 21, CDR2: SEQ ID NO: 22, CDR3: SEQ ID NO: 23; and
    (iv) CDR1: SEQ ID NO: 27, CDR2: SEQ ID NO: 28, CDR3: SEQ ID NO: 29; and
  (b) a VL having a set of complementarity-determining regions (CDR1, CDR2, and CDR3) selected from the group consisting of:
    (i) CDR1: SEQ ID NO: 12, CDR2: SEQ ID NO: 13, CDR3: SEQ ID NO: 14;

(ii) CDR1: SEQ ID NO: 18, CDR2: SEQ ID NO: 19, CDR3: SEQ ID NO: 20;
(iii) CDR1: SEQ ID NO: 24, CDR2: SEQ ID NO: 25, CDR3: SEQ ID NO: 26; and
(iv) CDR1: SEQ ID NO: 30, CDR2: SEQ ID NO: 31, CDR3: SEQ ID NO: 32.

In an embodiment, the antibodies comprise a combination of a VH and a VL having a set of complementarity-determining regions (CDR1, CDR2 and CDR3) selected from the group consisting of:
(i) VH: CDR1: SEQ ID NO: 9, CDR2: SEQ ID NO: 10, CDR3: SEQ ID NO: 11, VL: CDR1: SEQ ID NO: 12, CDR2: SEQ ID NO: 13, CDR3: SEQ ID NO: 14;
(ii) VH: CDR1: SEQ ID NO: 15, CDR2: SEQ ID NO: 16, CDR3: SEQ ID NO: 17, VL: CDR1: SEQ ID NO: 18, CDR2: SEQ ID NO: 19, CDR3: SEQ ID NO: 20;
(iii) VH: CDR1: SEQ ID NO: 21, CDR2: SEQ ID NO: 22, CDR3: SEQ ID NO: 23, VL: CDR1: SEQ ID NO: 24, CDR2: SEQ ID NO: 25, CDR3: SEQ ID NO: 26; and
(iv) VH: CDR1: SEQ ID NO: 27, CDR2: SEQ ID NO: 28, CDR3: SEQ ID NO: 29, VL: CDR1: SEQ ID NO: 30, CDR2: SEQ ID NO: 31, CDR3: SEQ ID NO: 32.

In an embodiment, the anti-IL-23p19 antibodies or antibody fragments thereof comprise a variable heavy chain sequence selected from the group consisting of: SEQ ID NOs: 1, 3, 5, and 7; and/or a variable light chain sequence selected from the group consisting of: SEQ ID NOs: 2, 4, 6, and 8.

In an embodiment, the anti-IL-23p19 antibodies or antibody fragments thereof comprise a pair of variable heavy chain and variable light chain sequences, selected from the following combinations: a variable heavy chain sequence comprising SEQ ID NO: 1 and a variable light chain sequence comprising SEQ ID NO: 2; a variable heavy chain sequence comprising SEQ ID NO: 3 and a variable light chain sequence comprising SEQ ID NO: 4; a variable heavy chain sequence comprising SEQ ID NO: 5 and a variable light chain sequence comprising SEQ ID NO: 6; and a variable heavy chain sequence comprising SEQ ID NO: 7 and a variable light chain sequence comprising SEQ ID NO: 8. The skilled person will further understand that the variable light and variable heavy chains may be independently selected, or mixed and matched, to prepare an anti-IL-23p19 antibody comprising a combination of variable heavy and variable light chain that is distinct from the pairings identified above.

In an embodiment, the anti-IL-23p19 antibodies or antibody fragments thereof comprise a pair of variable heavy chain and variable light chain sequences, selected from the following combinations: a variable heavy chain sequence that is 90%, 95%, or 99% identical to SEQ ID NO: 1 and a variable light chain sequence that is 90%, 95%, or 99% identical to SEQ ID NO: 2; a variable heavy chain sequence that is 90%, 95%, or 99% identical to SEQ ID NO: 3 and a variable light chain sequence that is 90%, 95%, or 99% identical to SEQ ID NO: 4; a variable heavy chain sequence that is 90%, 95%, or 99% identical to SEQ ID NO: 5 and a variable light chain sequence that is 90%, 95%, or 99% identical to SEQ ID NO: 6; and a variable heavy chain sequence that is 90%, 95%, or 99% identical to SEQ ID NO: 7 and a variable light chain sequence that is 90%, 95%, or 99% identical to SEQ ID NO: 8. The skilled person will further understand that the variable light and variable heavy chains may be independently selected, or mixed and matched, to prepare an anti-IL-23p19 antibody comprising a combination of variable heavy and variable light chain that is distinct from the pairings identified above.

In some embodiments, the anti-IL-23p19 antibodies (e.g., antagonist antibodies) bind with high affinity to the p19 subunit of IL-23 and do not bind to the p40 subunit of the related cytokine family member, IL-12.

In some embodiments, the antibody is a full-length antibody. In other embodiments, the antibody is an antibody fragment including, for example, an antibody fragment selected from the group consisting of: Fab, Fab', F(ab)$_2$, Fv, domain antibodies (dAbs), and complementarity determining region (CDR) fragments, single-chain antibodies (scFv), chimeric antibodies, diabodies, triabodies, tetrabodies, miniantibodies, and polypeptides that contain at least a portion of an immunoglobulin that is sufficient to confer IL-23 specific binding to the polypeptide.

In some embodiments, a variable region domain of an anti-IL-23p19 antibody disclosed herein may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly, a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example to provide a hinge region or a portion of a hinge region domain as found in a Fab fragment, or to provide further domains, such as antibody CH2 and CH3 domains.

In some embodiments, a variable region domain of an anti-IL-23p19 antibody may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly, a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example to provide a hinge region or a portion of a hinge region domain as found in a Fab' fragment, or to provide further domains, such as antibody CH2 and CH3 domains.

Thus, in one embodiment, the antibody fragment comprises at least one CDR as described herein. The antibody fragment may comprise at least two, three, four, five, or six CDRs as described herein. The antibody fragment further may comprise at least one variable region domain of an antibody described herein. The variable region domain may be of any size or amino acid composition and will generally comprise at least one CDR sequence responsible for binding to human IL-23p19, for example, CDR-H1, CDR-H2, CDR-H3, CDR-L1, CDR-L2, and/or CDR-L3 as described herein, and which is adjacent to or in frame with one or more framework sequences.

In some embodiments, the anti-IL-23p19 antibody is a monoclonal antibody. In some embodiments, the anti-IL-23p19 antibody is a human antibody. In alternative embodiments, the anti-IL-23p19 antibody is a murine antibody. In some embodiments, the anti-IL-23p19 antibody is a chimeric antibody, a bispecific antibody, or a humanized antibody.

In a further aspect, the anti-IL-23p19 antibody or antibody fragment thereof exhibits one or more of the following properties:
(a) is specific for human IL-23p19 and has the ability to block IL-23 binding to its receptor (IL-23R);
(b) inhibits, interferes with, or modulates IL-23p19 interaction with IL-23 receptor signal transduction;
(c) inhibits STAT3 activation induced by IL-23;
(d) inhibits IL-17 production induced by human IL-23 in mouse splenocytes;
(e) inhibits IL-17 production induced by human IL-23 in activated human T cells in PBMC;
(f) does not inhibit IL-23 interaction with IL-12Rβ1 signal transduction;
(g) does not inhibit human IL-12 induced interferon gamma production in human activated T-cells (PBMC);
(h) does not inhibit cynomolgus monkey IL-12 induced interferon gamma production in human activated T-cells (PBMC); and
(i) inhibits skin inflammation induced by human IL-23 in a murine psoriasis-like model.

In an embodiment, the anti-IL-23p19 antibodies or antibody fragments thereof can reduce, inhibit, interfere with, and/or modulate at least one of the biological responses related to IL-23, and as such, are useful for ameliorating the effects of IL-23 related diseases or disorders. Such antibodies and antibody fragments thereof can be used, for example, to reduce, inhibit, interfere with and/or modulate IL-23 signaling, IL-23 activation of Th17 cells, IL-23 activation of NK cells, or inducing production of proinflammatory cytokines.

In some embodiments, the anti-IL-23p19 antibodies or antibody fragments thereof comprise one or more conservative amino acid substitutions. A person of skill in the art will recognize that a conservative amino acid substitution is a substitution of one amino acid with another amino acid that has similar structural or chemical properties, such as, for example, a similar side chain. Exemplary conservative substitutions are described in the art, for example, in Watson et al., Molecular Biology of the Gene, The Benjamin/Cummings Publication Company, 4th Ed. (1987).

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al. (1998) *Acta Physiol Scand Suppl* 643: 55-67; Sasaki et al. (1998) *Adv Biophys* 35: 1-24). Amino acid substitutions to the antibodies of the invention may be made by known methods for example by PCR mutagenesis (U.S. Pat. No. 4,683,195).

In one embodiment, the anti-IL-23p19 antibody or antibody fragment thereof comprises all six of the CDR regions of the Hu-2. 18006B, Hu-4. 18006B, Hu-5. 18006B, or Hu-6. 18006B antibodies formatted as a chimeric or a humanized antibody. In other embodiments, the anti-IL-23p19 antibody or antibody fragment thereof comprises all six of the CDR regions of one of the disclosed fully human antibodies.

Methods of Producing Antibodies

Anti-IL-23p19 antibodies or antibody fragments thereof may be made by any method known in the art. For example, a recipient may be immunized with soluble recombinant human IL-23 protein, or a fragment or a peptide conjugated with a carrier protein thereof. Any suitable method of immunization can be used. Such methods can include adjuvants, other immune stimulants, repeat booster immunizations, and the use of one or more immunization routes.

Any suitable source of human IL-23 can be used as the immunogen for the generation of the non-human or human anti-IL-23p19 antibodies of the compositions and methods disclosed herein.

Different forms of the IL-23 antigen may be used to generate the antibody that is sufficient to generate a biological activity. Thus, the eliciting IL-23 antigen may be a single epitope, multiple epitopes, or the entire protein alone or in combination with one or more immunogenicity enhancing agents. In some aspects, the eliciting antigen is an isolated soluble full-length protein, or a soluble protein comprising less than the full-length sequence (e.g., immunizing with a peptide comprising particular portion or epitopes of IL-23). As used herein, the term "portion" refers to the minimal number of amino acids or nucleic acids, as appropriate, to constitute an immunogenic epitope of the antigen of interest. Any genetic vectors suitable for transformation of the cells of interest may be employed, including, but not limited to adenoviral vectors, plasmids, and non-viral vectors, such as cationic lipids.

It is desirable to prepare monoclonal antibodies (mAbs) from various mammalian hosts, such as mice, rodents, primates, humans, etc. Description of techniques for preparing such monoclonal antibodies may be found in, e.g., Sties et al. (eds.) BASIC AND CLINICAL IMMUNOLOGY ($4^{th}$ ed.) Lance Medical Publication, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE ($2^{nd}$ ed.) Academic Press, New York, N.Y. Typically, spleen cells from an animal immunized with a desired antigen are immortalized, commonly by fusion with a myeloma cell. See Kohler and Milstein (196) *Eur. J. Immunol.* 6:511-519. Alternative methods of immortalization include transformation with Epstein Barr Virus, oncogene, or retroviruses, or other methods known in the art. See. e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or an antigen binding fragment thereof by screening a DNA library from human B cells according, e.g., to the general protocol outlined by Huse et al., (1989) *Science* 246: 1275-1281. Thus, antibodies may be obtained by a variety of techniques familiar to researchers skilled in the art.

Other suitable techniques involve selection of libraries of antibodies in phage, yeast, virus or similar vector. See e.g., Huse et al., supra; and Ward et al., (1989) *Nature* 341:544-546. The polypeptides and antibodies disclosed herein may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literatures. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,996,345; 4,277,437; 4,275,149; and 4,366,241. Also, recombinant immunoglobulins may be produced, see Cabilly U.S. Pat. No. 4,816,567; and Queen et al. (1989)*Proc. Nat'l Acad. Sci. USA* 86: 10029-10023; or made in transgenic mice, see Nils Lonberg et al., (1994), *Nature* 368:856-859; and Mendez et al. (1997) *Nature Genetics* 15: 146-156; TRANSGENIC ANIMALS AND METHODS OF USE (WO 2012/62118), Medarex, Trianni, Abgenix, Ablexis, OminiAb, Harbour and other technologies.

In some embodiments, the ability of the produced antibody to bind to IL-23p19 can be assessed using standard binding assays, such as surface plasmon resonance (SPR), Octet (BLI), ELISA, Western Blot, immunofluorescence, flow cytometric analysis, chemotaxis assays, and cell migration assays. In some aspects, the produced antibody may also be assessed for its ability to inhibit IL-23 from blocking IL-23 receptor β1 signal transduction, and inhibit IL-23p19 and/or IL-23p19-mediated inflammatory microenvironment successive effects including inhibiting IL-23 induced Stat3 phosphorylation, IL-17 production and/or IFN-7 production.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., 1983 *J. Immunol. Meth.* 62:1-13). Protein G is recommended for all mouse isotypes and for human γ3 (see, e.g., Guss et al., 1986 *EMBO J.* 5:1567-1575). A matrix to which an affinity ligand is attached is most often agarose, but other matrices are available. Mechanically stable matrices such as controlled pore glass or poly (styrenedivinyl) benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25 M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present disclosure. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-IL-23p19 polypeptide (e.g., a heavy chain or light chain variable region), or its complement. Hybridizing nucleic acids of the type described herein can be used, for example, as a cloning probe, a primer, e.g., a PCR primer, or a diagnostic probe.

Polynucleotides, Vectors, and Cells

Other embodiments encompass isolated polynucleotides that comprise a sequence encoding an anti-IL-23p19 antibody or antibody fragment thereof, vectors, and cells comprising the polynucleotides, and recombinant techniques for production of the antibody. The isolated polynucleotides can encode any desired form of the anti-IL-23p19 antibody including, for example, full length monoclonal antibodies, Fab, Fab', F(ab')2, and Fv fragments, diabodies, linear antibodies, single-chain antibody molecules, miniantibodies, and multispecific antibodies formed from antibody fragments.

Some embodiments include isolated polynucleotides comprising sequences that encode the light chain variable region of an antibody or antibody fragment having the amino acid sequence of any of SEQ ID NOs: 2, 4, 6, and 8. Some embodiments include isolated polynucleotides comprising sequences that encode the heavy chain variable region of an antibody or antibody fragment having the amino acid sequence of SEQ ID NOs: 1, 3, 5, and 7.

In an embodiment, the isolated polynucleotide sequence (s) encodes an antibody or antibody fragment having a light chain and a heavy chain variable region comprising the amino acid sequences of:
  (a) a variable heavy chain sequence comprising SEQ ID NO: 1 and a variable light chain sequence comprising SEQ ID NO: 2;
  (b) a variable heavy chain sequence comprising SEQ ID NO: 3 and a variable light chain sequence comprising SEQ ID NO: 4;
  (c) a variable heavy chain sequence comprising SEQ ID NO: 5 and a variable light chain sequence comprising SEQ ID NO: 6; or
  (d) a variable heavy chain sequence comprising SEQ ID NO: 7 and a variable light chain sequence comprising SEQ ID NO: 8.

In another embodiment, the isolated polynucleotide sequence(s) encodes an antibody or antibody fragment having a light chain and a heavy chain variable region comprising the amino acid sequences of:
  (a) a variable heavy chain sequence that is 90%, 95%, or 99% identical to SEQ ID NO: 1 and a variable light chain sequence that is 90%, 95%, or 99% identical to SEQ ID NO: 2;
  (b) a variable heavy chain sequence that is 90%, 95%, or 99% identical to SEQ ID NO: 3 and a variable light chain sequence that is 90%, 95%, or 99% identical to SEQ ID NO: 4;

(c) a variable heavy chain sequence that is 90%, 95%, or 99% identical to SEQ ID NO: 5 and a variable light chain sequence that is 90%, 95%, or 99% identical to SEQ ID NO: 6; or (d) a variable heavy chain sequence that is 90%, 95%, or 99% identical to SEQ ID NO: 7 and a variable light chain sequence that is 90%, 95%, or 99% identical to SEQ ID NO: 8.

The polynucleotide(s) that comprise a sequence encoding an anti-IL-23p19 antibody or antibody fragment thereof can be fused to one or more regulatory or control sequence, as known in the art, and can be contained in suitable expression vectors or cells as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-IL-23p19 antibodies or antibody fragments thereof can also be produced as fusion polypeptides, in which the antibody or fragment is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the cell. For prokaryotic cells that do not recognize and process the anti-IL-23p19 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO 90/13646. In mammalian cells, mammalian signal sequences as well as viral secretory leaders, for example, the herpes simplex gD signal, can be used. The DNA for such precursor region is ligated in reading frame to DNA encoding the anti-IL-23p19 antibody.

Expression and cloning vectors contain a nucleic acid sequence that enables the vector to replicate in one or more selected cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

Non-Therapeutic Uses

The anti-IL-23p19 antibodies or antibody fragments described herein are useful as affinity purification agents. In this process, the antibodies are immobilized on a solid phase such a Protein A resin, using methods well known in the art. The immobilized antibody is contacted with a sample containing the IL-23p19 protein (or fragment thereof) to be purified, and thereafter the support is washed with a suitable solvent that will remove substantially all the material in the sample except the IL-23p19 protein, which is bound to the immobilized antibody. Finally, the support is washed with another suitable solvent that will release the IL-23p19 protein from the antibody.

Anti-IL-23p19 antibodies or antibody fragments are also useful in diagnostic assays to detect and/or quantify IL-23p19 protein, for example, detecting IL-23p19 expression in specific cells, tissues, or serum. The anti-IL-23p19 antibodies can be used diagnostically to, for example, monitor the development or progression of a disease as part of a clinical testing procedure to, e.g., determine the efficacy of a given treatment and/or prevention regimen. Detection can be facilitated by coupling the anti-IL-23p19 antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present disclosure.

The anti-IL-23p19 antibodies or antibody fragments can be used in methods for diagnosing an IL-23p19-associated disorder (e.g., a disorder characterized by abnormal expression of IL-23p19) or to determine if a subject has an increased risk of developing an IL-23p19-associated disorder. Such methods include contacting a biological sample from a subject with an anti-IL-23p19 antibody or antibody fragment thereof and detecting binding of the antibody to IL-23p19. By "biological sample" is intended any biological sample obtained from an individual, cell line, tissue culture, or other source of cells potentially expressing IL-23p19. Methods for obtaining tissue biopsies and body fluids from mammals are well known in the art.

In some embodiments, the method can further comprise comparing the level of IL-23p19 in a patient sample to a control sample (e.g., a subject that does not have an IL-23p19-associated disorder) to determine if the patient has an IL-23p19-associated disorder or is at risk of developing an IL-23p19-associated disorder.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, for example. Fluorescence can be quantified using a fluorimeter.

There are various well-characterized enzyme-substrate labels known in the art (see, e.g., U.S. Pat. No. 4,275,149). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in *Methods in Enzym*. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3,5,5-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methyl-umbelliferyl-β-D-galactosidase.

In another embodiment, the anti-IL-23p19 antibody or antibody fragment thereof is used unlabeled and detected with a labeled antibody that binds the anti-IL-23p19 antibody or antibody fragment thereof.

The antibodies and antibody fragments thereof described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

The anti-IL-23p19 antibody or antibody fragment thereof can be used to inhibit the binding of ligand to the IL-23 receptor. Such methods comprise administering an anti-IL-23p19 antibody to a cell (e.g., a mammalian cell) or cellular environment, whereby signaling mediated by the IL-23 receptor is inhibited. These methods can be performed in vitro or in vivo. By "cellular environment" is intended the tissue, medium, or extracellular matrix surrounding a cell.

Compositions and Methods of Treatment

The disclosure also provides compositions including, for example, pharmaceutical compositions that comprise an anti-IL-23p19 antibody or antibody fragment thereof. Such compositions have numerous therapeutic uses for the treatment, prevention, or amelioration of diseases or disorders (e.g., diseases or disorders involving a biological activity mediated by the IL-23/IL-23 receptor signaling axis) such as an immune-mediated inflammatory disorder or an autoimmune disease.

An anti-IL-23p19 antibody or antibody fragment thereof disclosed herein is useful in the treatment of various diseases or disorders such as an immune-mediated inflammatory disorder (IMID) or an autoimmune disease. Methods for treating an IL-23 associated disorder comprise administering a therapeutically effective amount of an anti-IL-23p19 antibody or antibody fragment thereof to a subject in need thereof. The IMID may be selected from the group consisting of, psoriasis, psoriatic arthritis, inflammatory bowel diseases (i.e., ulcerative colitis or Crohn's disease) ankylosing spondylitis, systemic lupus erythematosus, hidradenitis suppurativa, atopic dermatitis, and asthma.

The present disclosure also provides methods for the treatment or prevention of an IMID comprising administering a composition or formulation that comprises an anti-IL-23p19 antibody or antibody fragment thereof, and optionally another immune-based therapy, to a subject in need thereof.

The disclosed antibodies are also useful in methods of treatment of cancer, either alone (e.g., as monotherapies) or in combination with other immunotherapeutic agents and/or a chemotherapy.

The antibodies can be administered either alone or in combination with other compositions that are useful for treating an immune-mediated inflammatory disorder or an autoimmune disease. In some embodiments, compositions including, for example, pharmaceutical compositions, comprising the anti-IL-23p19 antibody can further comprise a therapeutic agent, either conjugated or unconjugated to the binding agent.

In some aspects, a composition, e.g., a pharmaceutical composition is provided that comprises one or more antibodies disclosed herein. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A composition can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

Dosage levels of the active ingredients in the pharmaceutical compositions may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions described herein may be administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease.

In some aspects, the compositions described herein are administered to patients, e.g., in vivo, to treat or prevent a variety of disorders such as those described herein. Preferred patients include human patients having disorders that can be corrected or ameliorated by administering the agents modulate a biological activity of the IL-23/IL-23 receptor signaling axis.

In some aspects, conventional viral and non-viral based gene transfer methods can be used to introduce nucleic acids encoding the antibodies or derivatives thereof, as described herein, in mammalian cells or target tissues. Such methods can be used to administer nucleic acids encoding the antibodies to cells in vitro. In some embodiments, the nucleic acids encoding the antibodies or derivatives thereof are administered for in vivo or ex vivo gene therapy uses. In other embodiments, gene delivery techniques are used to study the activity of the antibodies in cell based or animal models. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the disclosure include lipofection, microinjection, biolistics, virosomes, liposomes, immunoliposomes, polycation or lipid:nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of nucleic acids encoding the antibodies described herein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the disclosure could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. All patents and publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The broad scope of this disclosure is best understood with reference to the following examples, which are not intended to limit the disclosures to the specific embodiments. The specific embodiments described herein are offered by way of example only, and the disclosure is to be limited by the terms of the appended claims, along with the full scope of the equivalents to which such claims are entitled.

EXAMPLES

General Methods

Methods for protein purification including immunoprecipitation, chromatography, and electrophoresis, are described. Coligan et al. (2000) *Current Protocols in Protein Science*, Vol. 1, John Wiley and Sons, Inc., New York. Chemical analysis, chemical modification, post-translational modification, production of fusion proteins, and glycosylation of proteins are described. See, e.g., Coligan et al. (2000) *Current Protocols in Protein Science*, Vol. 2, John Wiley and Sons, Inc., New York; Ausubel et al. (2001) *Current Protocols in Molecular Biology*, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391. Production, purification, and fragmentation of polyclonal and monoclonal antibodies are described. Coligan et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra.

Hybridoma supernatant was purified via HiTrap protein G column (GE, cat. No. 17040401) according to the manufacturer's procedures. Briefly, protein G column was equilibrated with DPBS (Gibco, cat. No. 14190-136) for 5 CV and hybridoma supernatant was loaded via syringe/infusion pump (Legato 200, KDS) at ambient temperature and 3 minutes residence time. The column was washed with 5 CV of DPBS and elution was performed with 4 CV of pH 2.8 elution buffer (Fisher Scientific, cat. No. PI21004). Elution was fractionated, and fractions were neutralized with 1M Tris-HCL, pH 8.5 (Fisher Scientific, cat No. 50-843-270) and assayed by A280 (DropSense96, Trinean). Peak fractions were pooled, and buffer exchanged into DPBS. Centrifugal filters (EMD Millipore, cat. No. UFC803024) were equilibrated in DPBS at 4,000×g for 2 minutes. Purified sample was loaded, DPBS was added and the sample was spun at 4,000×g for 5-10 minutes spins until total DPBS volume reached ≥6 DV. The final pool was analyzed by A280.

Standard methods in molecular biology are described. Maniatis et al., (1982) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif. Standard methods also appear in Ausbel et al., (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

The sequences for the heavy and light chain variable regions for hybridoma clones were determined as described below. Total RNA was extracted from 1-2×10⁶ hybridoma cells using the RNeasy Plus Mini Kit from Qiagen (Germantown, Md., USA). cDNA was generated by performing 5' RACE reactions using the SMARTer RACE 5'/3' Kit from Takara (Mountain View, Calif., USA). PCR was performed using the Q5 High-Fidelity DNA Polymerase from NEB (Ipswich, Mass., USA) to amplify the variable regions from the heavy and light chains using the Takara Universal Primer Mix in combination with gene specific primers for the 3' mouse constant region of the appropriate immunoglobulin. The amplified variable regions for the heavy and light chains were run on 2% agarose gels, the appropriate bands excised and then gel purified using the Mini Elute Gel Extraction Kit from Qiagen. The purified PCR products were cloned using the Zero Blunt PCR Cloning Kit from Invitrogen (Carlsbad, Calif., USA), transformed into Stellar Competent *E. Coli* cells from Takara and plated onto LB Agar+50 µg/ml kanamycin plates. Direct colony Sanger sequencing was performed by GeneWiz (South Plainfield, N.J., USA). The resulting nucleotide sequences were analyzed using IMGT V-QUEST to identify productive rearrangements and analyze translated protein sequences. CDR determination was based on IMGT numbering.

Methods for flow cytometry, including fluorescence activated cell sorting detection systems (FACS®), are available. See, e.g., Owens et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) Catalogue, Molecular Probes, Inc., Eugene, Oreg.; Sigma-Aldrich (2003) Catalogue, St. Louis, Mo.

The positive controls (PC1 and PC2), IL-23p19 and IL-12/IL-23 p40 specific antibodies, were made by a CRO (Biointron). Control antibodies can be prepared by any suitable expression methods. For example, by cloning the antibody heavy and light chain variable regions into the 293F or ExpiCHO™ expression system (ThermoFisher Scientific, Waltham, Mass.). These antibodies were used as controls to establish the binding and functional assays described in the examples and tested alongside the disclosed newly generated anti-IL-23p19-specific antibodies. "PC1" refers to a reference antibody, synthesized based on the VH and VL sequences reported in U.S. Pat. No. 7,935,344 (VH SEQ ID NO: 106 and VL SEQ ID NO: 116 in the '344 patent) and known to be specific for human IL-23p19 subunit (Biointron, LOT NO: 20180926A04). The term "PC2" refers to a reference, synthesized based on the VH and VL sequences reported in U.S. Pat. No. 6,902,734 (VH SEQ ID NO: 7 and VL SEQ ID NO: 8 in the '734 patent) and known to be specific for human IL-12/IL-23 p40 subunit (BIOINTRON LOT NO: 20180925A07).

Control antibodies can be made by standard methods. For example, plasmids containing the control antibodies' sequences can be transfected using a mammalian system (293F or ExpiCHO™) (Catalog Number: A29133, ThermoFisher Scientific, USA) according to the manufacturer's protocol. The cells are cultured at 37° C. and 8% $CO_2$ at day 1 and then at 32° C. and 5% $CO_2$ post-transfection in media provided in the kit. Antibodies are purified by clarifying the ExpiCHO™ culture medium by centrifugation at 1,000 g for 10 minutes followed by 5,000 g for 30 minutes. The supernatant is then filtered using a 0.45 µm filter followed by a 0.22 µm filter. Subsequently, the supernatant is subjected to affinity purification using protein A/G resins (Life Technologies, Carlsbad, Calif.; Catalog #20424) according to the manufacturer's protocol. Prior to ELISA purification, antibody titer in the culture medium is roughly determined to ensure the amount of medium loaded occupied less than 80% of the resin binding capacity. After incubation, the resins are washed with PBS and eluted with Elution Buffer (Life Technologies, Catalog #21004). The elution fractions are immediately adjusted to physiologic pH by adding Tris Buffer, pH 8.0. The purified antibodies are subsequently subjected to buffer exchange and protein concentration using Amicon Ultra-15 Centrifugal Filter Unit (Life Technologies, Catalog #UFC900324) in PBS buffer. Antibody concentration is determined by BCA Protein Assay. SDS-PAGE and Coomassie-staining is carried out to test the antibody purity. The purified protein is aliquoted and stored at −80° C. for long time storage or kept at 4° C. for immediate use.

The integrity of the antibody can be validated by SDS-PAGE followed by Coomassie staining under non-reducing vs reducing conditions; under non-reducing condition, one dominating band around 150 kDa, whereas under reducing conditions, two bands are observed, 50 kDa and 25 kDa. Standard techniques for characterizing ligand/receptor interactions are available. See, e.g., Coligan et al. (2001) Current Protocols in Immunology, Vol. 4, John Wiley, Inc., New York. Standard methods of antibody functional characterization appropriate for the characterization of antibodies with particular mechanisms of action are also well known to those of skill in the art.

Software packages and databases for determining, e.g., antigenic fragments, leader sequences, protein folding, functional domains, CDR annotation, glycosylation sites, and sequence alignments, are available.

Example 1: Generation of Anti-IL-23p19 Antibodies

Human anti-IL-23p19 specific antibodies were generated by immunizing human Ig transgenic mice (see, e.g., WO 2013/063391, TRIANNI® mice).

Immunization: TRIANNI® mice were immunized by injection with human IL-23 recombinant protein or combination of human IL-23 protein and heterodimer of human p19 and mouse p40 protein intraperitoneally (IP), subcutaneously (SC), or via footpad or base of the tail. The immune response was monitored by retroorbital bleeds. The plasma was screened by ELISA (as described below) for activity of binding to human IL-23 heterodimer. Mice with sufficient titers were used for fusions. Mice were boosted with the immunogen before sacrifice and removal of the spleen and draining lymph nodes.

Selection of mice producing anti-IL-23p19 antibodies: To select Trianni mice producing p19-specific antibodies, sera from immunized mice was screened by ELISA for binding to recombinant human IL-23. Briefly, an ELISA plate coated with recombinant human IL-23 was incubated with dilutions of serum from immunized mice for one hour at room temperature, the assay plate was washed, and specific antibody binding was detected with HRP-labeled anti-mouse IgG antibody. Plates was read using an ELISA reader (Biotek).

Generation of Hybridomas: To generate hybridomas producing human antibodies of the disclosure, splenocytes and draining lymph node cells harvested from immunized mice were fused to an appropriate immortalized cell line, such as a mouse myeloma cell line. The resulting hybridomas were screened for the production of p19-specific antibodies. For example, single cell suspensions of splenocytes and lymph node cells from immunized mice were fused to equal number of Sp2/0 non-mouse IgG secreting myeloma cells (ATCC, CRL 1581) by electrofusion. Cells were plated in flat bottom 96-well tissue culture plates, followed by about 2 weeks of incubation in selection medium (HAT medium), then switched to hybridoma culture medium. Approximately 10-14 days after cell plating, supernatants from individual wells were screened by ELISA as described above. The antibody-secreting hybridomas were transferred to 24-well plates, screened again, and if still positive for anti-p19 activity, the hybridomas were subcloned by limiting dilution or sorting using a single cell sorter. The stable subclones were then cultured in vitro to generate small amounts of antibodies to be used for purification and characterization.

Hybridoma Screening: Hybridoma supernatants were tested for IL-23 specific binding using human IL-23, human IL-12, and human p19/mouse p40 by ELISA using the same assay used to monitor the immune response of the immunized mice as described above.

Example 2: Binding of Anti-IL-23p19 Specific Antibodies

Binding of anti-IL-23p19-specific antibodies to IL-23 proteins was analyzed by Surface plasmon resonance (SPR) determined by BIAcore. Briefly, serial dilutions of the anti-IL-23p19 antibodies or the control antibodies were captured on an anti-mouse or human Fc chip (s) that were immobilized on the CM5 chip using amine coupling kit (GE Healthcare, Catalog NO: BR-1000-50, LOT NO: 2087295).

The control antibodies used in the BIAcore binding assay included: PC1 (known to be a p19 specific antibody, Biointron, LOT NO: 20180926A04); PC2 (a reference antibody with known specificity for the p40 subunit of human IL-12 and IL-23, Biointron, LOT NO: 20180925A07); a human IgG isotype control (Invitrogen, Catalog NO: 02-7102, LOT NO: TJ276309); a mouse IgG2a isotype control (made by Novarock Biotherapeutics) and a human IgG4 isotype control (Dendritics, Catalog No: DDXCH04P-100; Batch: DDXCH04-028) as negative controls.

Next, serial dilutions of IL-23 recombinant protein, human p19/mouse p40 heterodimer protein, human IL-12 protein and human p40 subunit protein in the running buffer containing 10 mM HEPES, 150 mM NaCl, 3 mM EDTA, 0.005% Tween 20, pH 7.4, were injected at 50 µl/minute over immobilized antibody for 1 minute followed by 2 minutes dissociation. Each injection was followed by a regeneration step with a 60-second pulse of 10 mM Glycine-HCl, pH 1.7 buffer. Fitting of experimental data was done with BIAevaluation software (GE Healthcare), fit with a Langmuir 1:1 model to determine apparent binding.

Figure 2C:
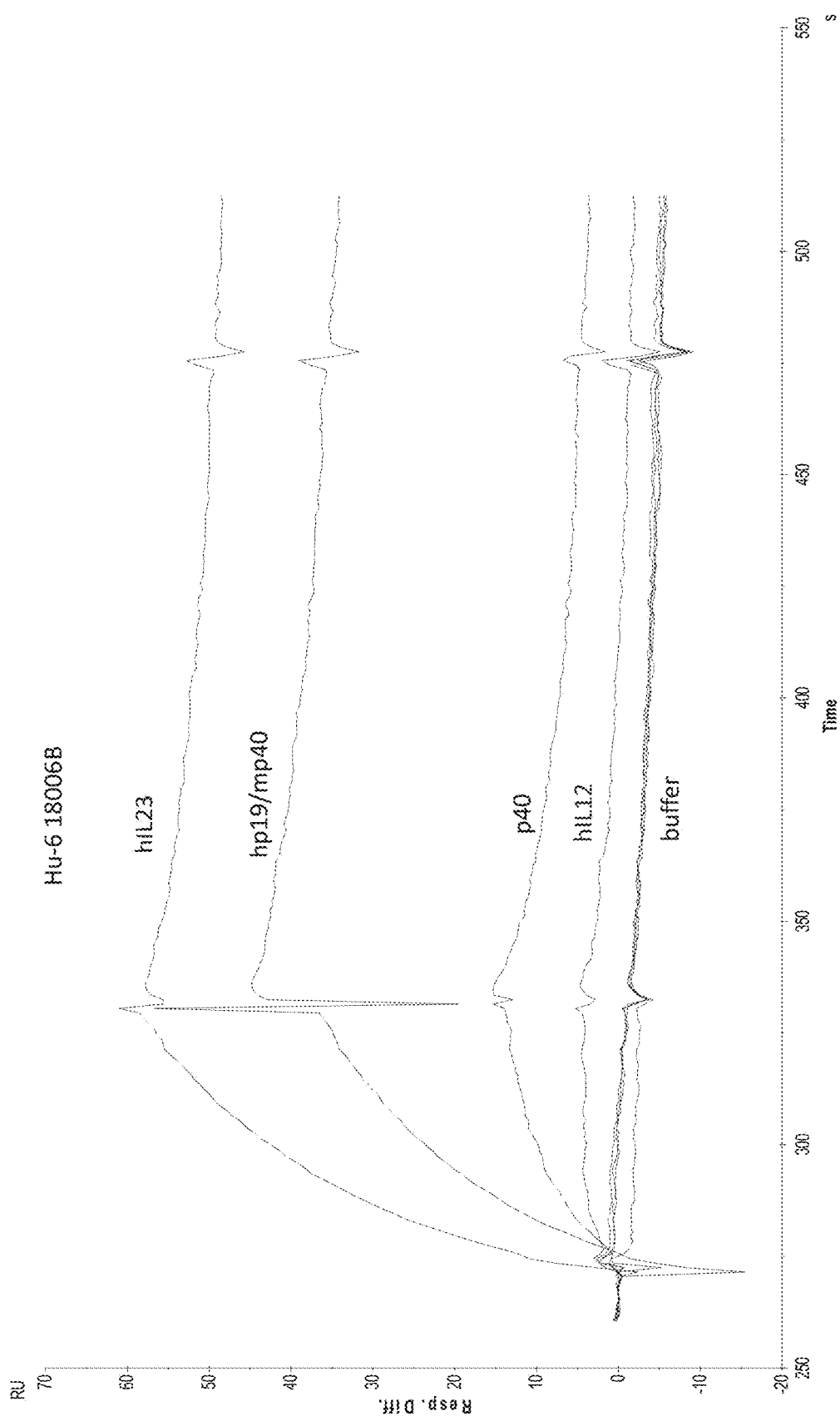
Figure 3A:
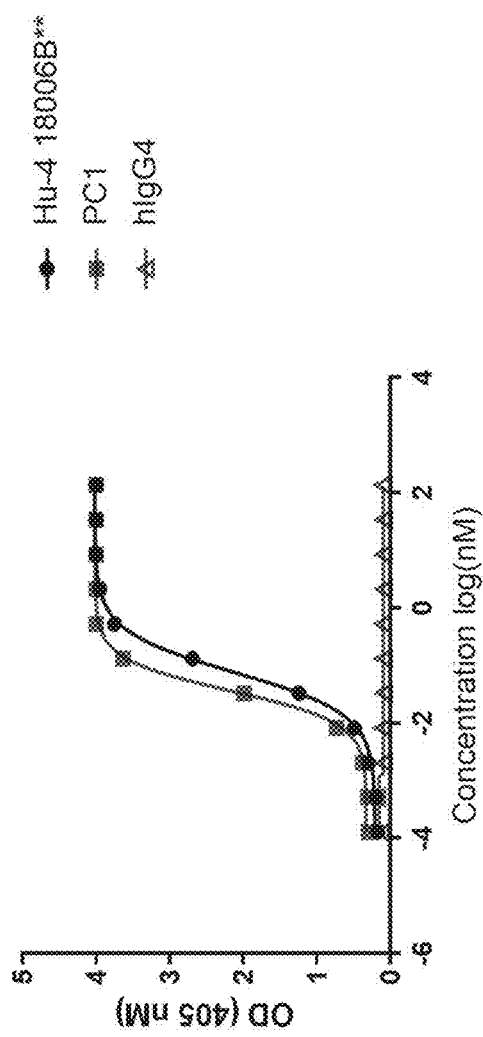
FIGS. 3A, 3B and 3C show dose-dependent binding of the selected representative IL-23p19 antibodies to human IL-23 and a recombinant cytokine comprising human p19 and murine p40 subunits determined by ELISA.
Figure 3B:
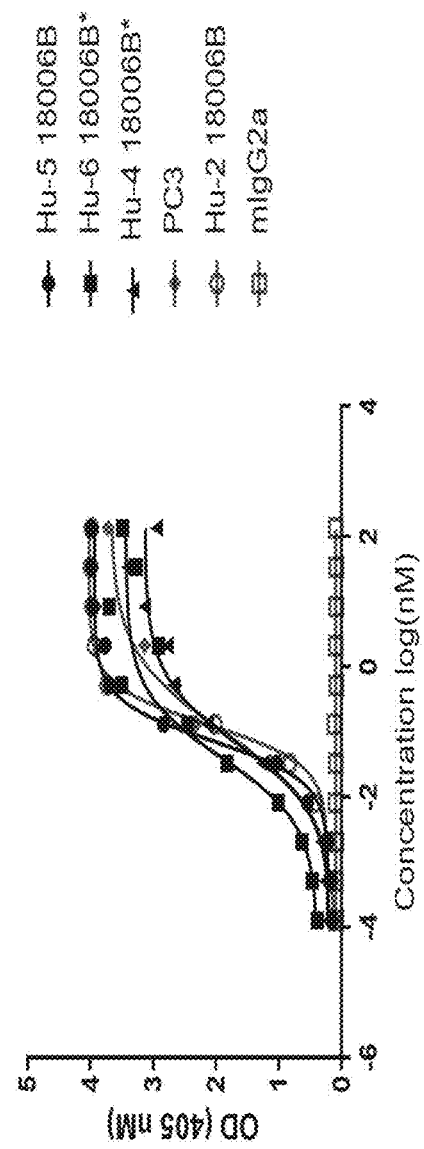
Figure 3C:
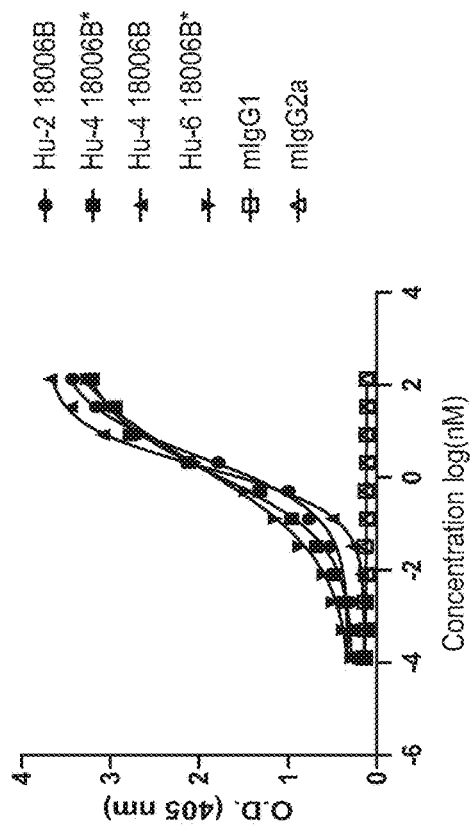
Figure 3E:
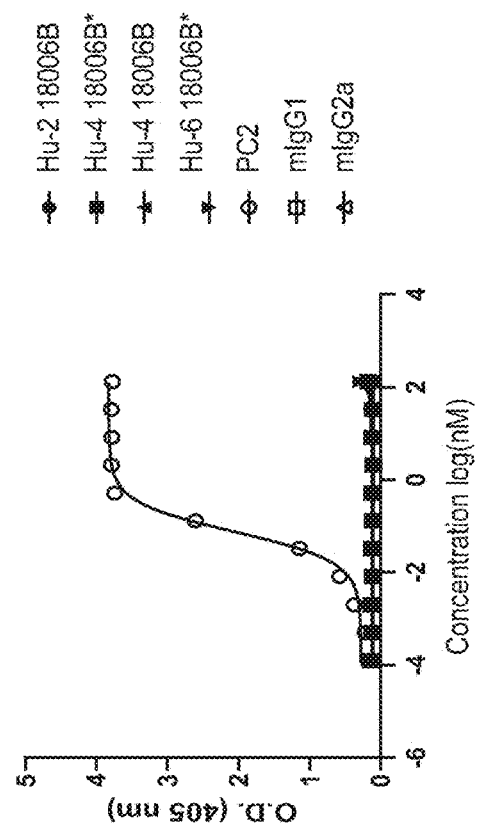
FIGS. 3D and 3E show no binding of the selected representative anti-IL-23p19 antibodies to human IL-12 and human p40 subunit determined by ELISA.
Figure 3D:
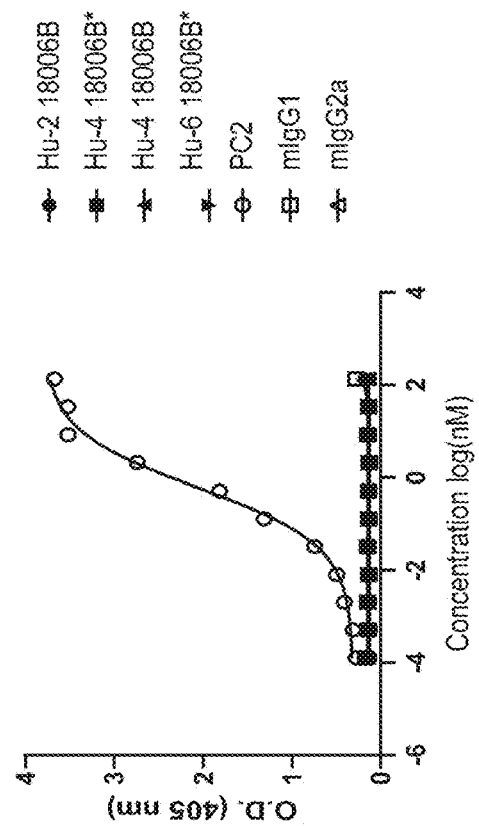

The binding profiles of the purified antibodies are depicted in FIG. 2. FIG. 2A shows the binding profile of Hu-2 18006B (purified from hybridoma). FIG. 2B shows the binding profile of Hu-5 18006B (purified from hybridoma). FIG. 2C shows the binding profile of Hu-6 18006B* (recombinant mIgG2a). FIG. 2D shows the binding profile of Hu-4 18006B* (*recombinant, mIgG2a). FIG. 2E shows the binding profile of Hu-4 18006B (recombinant, hIgG4). Table 3 summarizes the anti-IL-23p19 antibodies and their binding specificity to human IL-23 and the human p19/mouse p40 heterodimer protein by BIAcore. Recombinant antibodies are designated with astericks in the table.

TABLE 3

Binding of IL-23p19 specific antibodies by BIAcore

| Antibody | Isotype | hIL23 | hp19/mp40 | hIL12 | hp40 |
|---|---|---|---|---|---|
| Hu-2 18006B | mIgG1, kappa | + | + | − | − |
| Hu-5 18006B | mIgG2b, lambda | + | + | − | − |
| Hu-6 18006B* | mIgG2a, kappa | + | + | − | − |
| Hu-4 18006B* | mIgG2a, kappa | + | + | − | − |
| Hu-4 18006B** | hIgG4, kappa | + | + | − | − |
| PC1 (p19 specific) | hIgG1, lambda | + | + | − | − |
| PC2 (p40 specific) | hIgG1, kappa | + | − | + | + |
| hIgG | hIgG | − | − | − | − |
| mIgG2a | mIgG2a | − | − | − | − |

*IL-23p19 recombinant antibodies; PC1 and PC2 are recombinant antibodies; the rest of IL-23p19 Abs are purified from hybridomas The results show that the anti-IL-23p19 antibodies bind to human IL-23 and the human p19/mouse p40 heterodimer but not human IL-12 or human p40 subunit (FIG. 2 and Table 3).

PC1 was positive on human IL-23, human p19/mouse p40 and negative on human IL-12 and human p40 subunit (data not showed). PC2 was positive on human IL-23, human IL-12, human p40 subunit and negative on human p19/mouse p40 heterodimer. The isotype controls mIgG2a and hIgG did not bind hIL-23, hp19/mp40, hIL-12 and hp40 subunit.

Results: Anti-IL-23p19-specific antibodies were characterized by their binding to human IL-23 and a recombinant protein comprising a heterodimer consisting of a human p19 and a mouse p40 subunit. These antibodies did not bind to human IL-12 and human p40 subunit by BIAcore.

The binding specificity of the disclosed anti-IL-23p19 antibodies were also assessed by ELISA. Briefly, biotinylated IL-23 were captured via streptavidin coated ELISA plates. Human p19/mouse p40, human IL-12 and human p40 subunit were directly coated to ELISA plates. Purified antibodies were then added to the plates followed by detection by goat-anti-mouse IgG-HRP (Jackson ImmunoResearch, catalog no: 115-036-071, LOT NO: 147271). After addition of ABTS substrate (Moss Inc., catalog no: ABTS-1000, LOT NO: 03086202), ELISA plates were read using an ELISA plate reader (Biotek). The controls depicted in FIG. 3: PC1 refers to a reference antibody (known to be a p19 specific antibody, Biointron, LOT NO:20180926A04); PC2 refers to a reference antibody (known to be a p40 specific antibody, Biointron, LOT NO: 20180925A07); PC3 refers to a reference antibody (MT155, known as a p19 specific antibody from Mabtech, catalog no: 3457-6-100, code: 3457-6-1000), the negative controls are human IgG4 (Dendritics, catalog no: DDXCHO4P-100, LOT NO: DDXCH04-028) and the mouse IgG2a (generated by Novarock Biotherapeutics).

FIG. 3 shows the binding activities of the disclosed p19-specific antibodies. FIGS. 3A and 3B show that Hu-4 18006B** (hIgG4) and Hu-5 18006B (mIgG2b), Hu-6 18006B* (mIgG2a), Hu-4 18006B* (mIgG2a) and Hu-2 18006B (mIgG1) bind to human IL-23 in a dose-dependent manner; the positive control PC1 binds to IL-23 in a dose dependent manner (FIG. 3A). FIG. 3C shows that the these selected representative anti-IL-23p19 antibodies, H-2 1800B (mIgG1), Hu-4 18006B (mIgG2c), Hu-4 18006B* (mIgG2a) and H-6 18006B* (mIgG2a) bind to human p19/mouse p40 heterodimer in a dose dependent manner. FIG. 3D shows that these anti-IL-23p19 antibodies do not bind to hL-12 while the positive control antibody PC2 binds to hIL-12 in a dose dependent manner. FIG. 3E shows that these anti-IL-23p19 antibodies do not bind to the human p40 subunit while the positive control PC2 binds to the human p40 subunit in a dose responding manner.

Results from FIG. 3A to 3E indicated that the anti-IL-23p19-specific antibodies are characterized by binding to human IL-23 and a recombinant protein comprising a heterodimer consisting of the human p19 combined with the mouse p40 subunit by ELISA. These antibodies do not bind human IL-12 and human p40 subunit.

To ensure accurate measurements of the KD and IC50 endpoints in binding and functional assays, the antibodies were purified from the hybridoma culture supernatants prior to testing. The binding kinetics of the disclosed anti-IL-23p9-specific antibodies to recombinant human IL-23 was determined by Surface plasmon resonance (SPR) using BIAcore 3000 system docked with a CM5 chip previously immobilized via amine coupling chemistry with anti-mouse IgG antibody (GE Cat No. BR-1008-38). Flow cell 1 remained unmodified to serve as a reference cell for substraction of systematic instrument noise and drift. Fc2-1 detection was run with double blanking (Fc1 and blank analyte buffer). Antibody samples were diluted to 50 µg/mL in HBS-EP (GE, catalog no: BR1001-88) and injected at a flow rate of 10 uL/minute for 1 minute. Next, hIL-23 (R&D systems, catalog no: 1290-IL/CF) diluted to 0.156-40 nM was injected at 50 µL/minute for 2 minutes, followed by 10 minutes dissociation. Data were analyzed in BIAEvalution software (GE Healthcare) by 1:1 binding model with global fit to determine apparent binding kinetics.

The binding kinetic data for the disclosed anti-IL-23p19 antibodies is provided in Table 4. The results indicate that the anti-IL-23p19-specific antibodies bind to human recombinant IL-23 with a KD ranging from 3.84E-11 to 6.62E-11 M. PC1 (known to be a p19 specific antibody, Biointron, LOT NO: 20180926A04) had KD values ranging from 3.77E-10 to 1.10E-11 over multiple runs.

TABLE 4

SPR Binding Kinetics

| Anti-IL-23p19 mAb | ka (1/Ms) | kd (1/s) | KD (M) |
|---|---|---|---|
| Hu-2 18006B | 1.57E+06 | 6.54E−05 | 4.16E−11 |
| Hu-5 18006B | 1.49E+06 | 9.89E−05 | 6.62E−11 |
| Hu-6 18006B* | 4.44E+06 | 1.71E−04 | 3.84E−11 |
| Hu-4 18006B** | 2.50E+06 | 1.43E−04 | 5.72E−11 |

Example 3: Blocking IL-23 Interaction with IL-23 Receptor

The ability of disclosed p19-specific antibodies to block IL-23 binding with its cognate high affinity IL-23 receptor was determined by ELISA. Briefly, human IL-23 receptor was coated on a 96-well plate (2 µg/ml), then serial dilutions of the purified anti-IL-23p19 antibodies premixed with recombinant human IL-23 (50 ng/mL) were added to the plate. After a 30 minute incubation, the plate was washed. Then, biotinylated anti-p40 antibody (Invitrogen ref: 13-7129-85, lot: 2028761, 1/3000 dilution) was added to the plate. After 30 minute incubation, the plate was washed followed by detection by streptavidin HRP. The plate was read using a plate reader (OD 405 nM) after addition of the ABTS substrate. The positive control antibody PC1 used in this blocking assay is a reference antibody (known to be a p19 specific antibody, Biointron, LOT NO: 20180926A04).

The negative controls were mouse IgG1 (Novus, catalog no: NBP1-97005, LOT NO: 35613), mIgG2a (made by Nova-Rock Biotherapeutics), and hIgG4 (Dendritics, catalog no: DDXCHO4P-100, LOT NO: DDXCH04-028).

Figure 4:
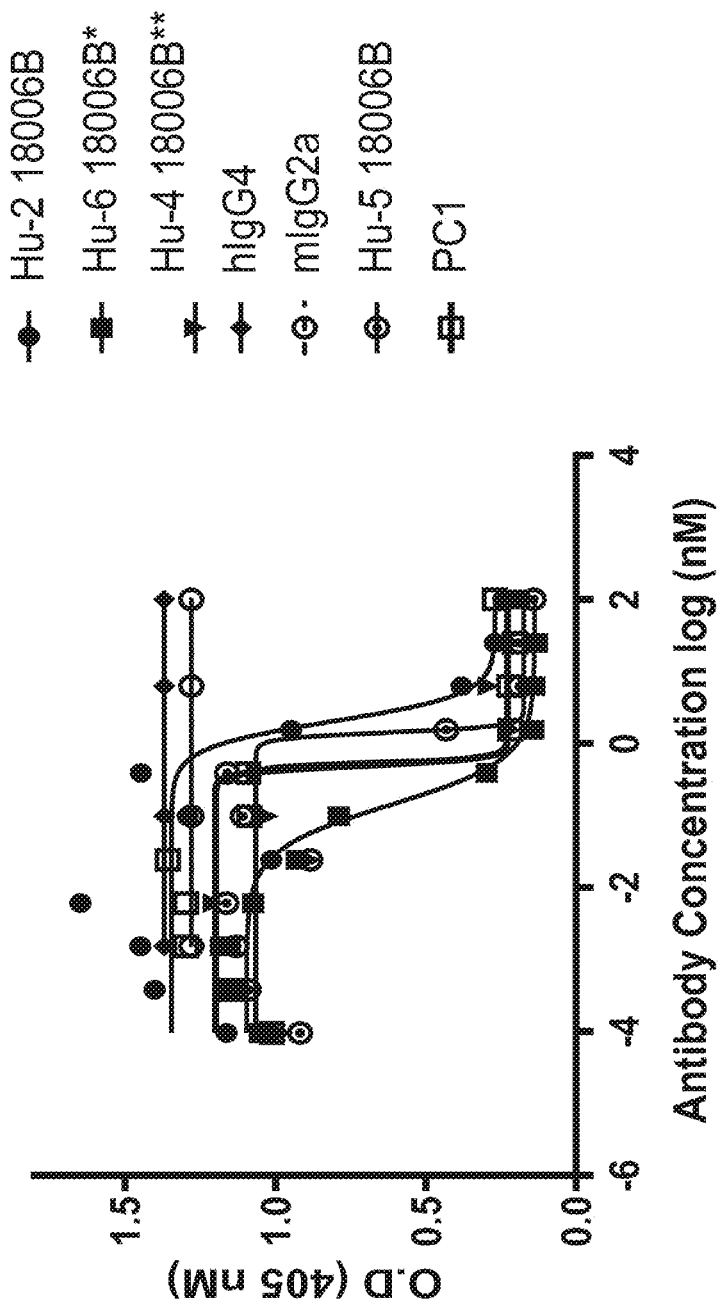
FIG. 4 shows blocking of the IL-23/IL-23 receptor interaction by the four IL-23p19 antibodies as determined by ELISA.

Results: The data in FIG. 4 showed that the disclosed anti-p19 antibodies (Hu-2 18006B, Hu-6 18006B*, Hu-5 18006B and Hu-4 18006B**) blocked the interaction of human IL-23 with the human IL-23 receptor in a dose-dependent manner. The positive control PC1 also blocked IL-23/IL-23 receptor interaction in a dose responding manner. The negative controls hIgG4 and mIgG2a were negative in the assay.

To demonstrate the specificity of the disclosed p19-specific antibodies, a blocking assay was designed to evaluate the ability of the antibodies to block IL-23 binding with IL-12 receptor β1.

Briefly, human IL-12 receptor β1 was coated on a 96-well plate (2 µg/ml), then serial dilutions of the purified anti-IL-23p19 antibodies premixed with recombinant human IL-23 (50 ng/ml) were added to the plate. The positive control antibody used in the blocking assay was PC2 (a reference antibody with known specificity for the p40 subunit of the IL-12/IL-23 p40, Biointron Lot NO: 20180925A07) The negative control was a mouse IgG1 (Novus, catalog no: NBP1-97005, lot 35613).

After a 30 minute incubation, the plate was washed. Then, biotinylated anti-p40 antibody (Invitrogen ref: 13-7129-85, lot: 2028761, 1/3000 dilution) was added to the wells that contained the anti-IL-23p19 antibodies; the biotinylated anti-p19 antibody (Mabtech, cat no: MT155, code: 3457-6-1000) was add to the wells that contained PC2 antibody. After 30 minute incubation, the plate was washed followed by detection by streptavidin HRP. The plate was read using a plate reader (OD 405 nM) after addition of the ABTS substrate.

Figure 5:
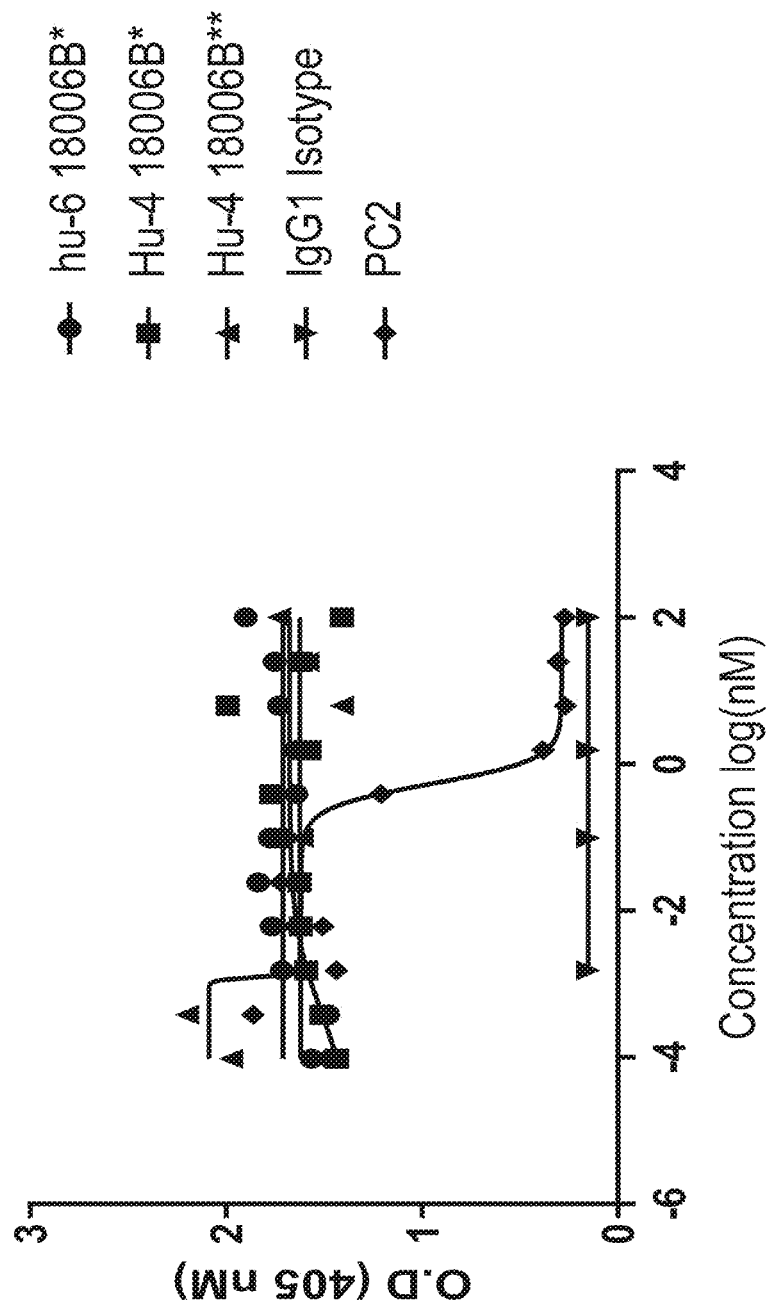
FIG. 5 shows two representative IL-23p19 antibodies that do not block IL-23/IL-12 receptor β1 interaction.

Results: The data in FIG. 5 showed that of the 3 selected p19 specific antibodies (Hu-6 18006 B*, Hu-4 18006B* and Hu-4 18006 B**) did not block the IL-23/IL-12 receptor β1 binding interaction. Similarly, the PC1 antibody also did not block the IL-23/IL-12 receptor β1 interaction (data not shown). However, the p40 control antibody (PC2) blocked the interaction of IL-23/IL-12β1 as expected.

Example 4: Inhibition of IL-17 Production in Mouse Splenocyte Assay

It is widely known that human IL-23 binds murine IL-23R and induces murine IL-17 production in mouse splenocytes. Human IL-23 in the presence of IL-2 stimulates the production of IL-17 in murine splenocytes at very low (picomolar) concentrations, which can be inhibited by coincubation with inhibitors against either p40 or p19 (Aggarwal, S., et al., 2003, *J Biol Chem;* 278: 1910-4; Singh et al., 2015, *MAbs*, July-August; 7(4): 778-791).

The ability of the disclosed anti-IL-23p19-specific antibodies to inhibit human IL-23-induced IL-17 production was evaluated in a murine splenocyte assay (MSA). The potency for the inhibition of human-IL-23-induced IL-17 production was determined.

Briefly, mouse splenocytes were isolated from a C57/BL-6 mouse using a glass homogenizer and a Ficoll Pague cells isolation kit (Ge Healthcare, catalog no: 17-5442-02) following the manufacture's procedures. The splenocytes were activated with IL-2 (20 ng/ml for $5\times10^6$ cells/ml) for 5 minutes, then human IL-23 (1.5 ng/ml) was added to the splenocytes. The activated splenocytes were plated out to a 96-well plate, 100 ul/well. 100 ul/well of the 4 purified p19 antibodies, hu-6 18006B* (mIgG2a), Hu-4 18006B* (mIgG2a), Hu-4 18006** (hIgG4) and Hu-2 18006B (mIgG1), were added to the plates.

After 72 hour incubation, the supernatants were transferred out from the plate for IL-17 quantification assay using a quantikine ELISA kit (R&D, M1700 or SM1700). Controls included in the IL-17 MSA: PC1 (a reference antibody known to be a p19 specific antibody, Biointron Lot NO:20180926A04) as a positive control; a mouse IgG1 (Novus, catalog no: NBP 1-97005) and a human IgG4 (Dendritics, Cat: DDXCHO4P-100, Lot: DDXCH04-028) as negative controls.

Results: The data presented in FIGS. 6A and 6B support the conclusion that the disclosed antibodies selectively neutralize the binding of IL-23 to IL-23R and, therefore, inhibit IL-17 production in a dose-dependent manner.

Example 5: Inhibition of STAT3 Activation by a Reporter Cell Assay

It is known that the receptor for IL-23 comprises an IL-12Rβ1 subunit shared in common with IL-12 receptor, partnered with IL-23R. IL-23p19 selectively binds to IL-23R and signaling through IL-23R induces Janus kinase 2 (JAK2) which activates STAT3, leading to the upregulation of RORγgt and subsequent increases in the production of inflammatory cytokine IL-17 (Parham et al., J. Immunol. 168:5699-5708, 2002). In order to determine if the disclosed anti-p19 antibodies can inhibit STAT3 activation, the antibodies were assessed on IL-23 induced STAT3 activation by a reporter cell assay. Human IL-23 induces STAT3 phosphorylation upon IL-23R binding at the surface of the human lymphoma DB cells (US2013/0172272 Example 13, and Desmet, J. et al., *Nat. Commun.* 5:5237 (2014).

DB cells were derived from the human B cell lymphoma cell line, which expressed endogenous IL-23 receptors and STAT3 to provide a fully functional IL-23 signaling pathway. DB assay cells were generated by stable transfection of DB cells with pGL4.47[luc2p/SIE/Hybro], which allow the quantitative detection of bioactive human IL23 using a luciferase reporter system.

This DB assay is to measure the inhibitory activity of the disclosed anti-IL-23 antibodies on human IL-23-induced STAT3 activation. Briefly, DB cells (ATCC, CRL-2289) were cultured in growth medium (RPMI+10% FBS) for 2 days. On the day of the experiment, cells were harvested and resuspended in growth medium. A serial dilutions of the tested antibodies were prepared in the growth medium in the Low Binding 384-well plate (ThermoScientific 264574) followed by adding human IL-23 and incubated at room temperature for 30 minutes. The mixture of the tested antibodies and human IL-23 were then added to the plate. The signaling assay plate was incubated in a humidified 37° C./5% CO2 incubator for 16 hours. OneGlo reagent was added and the mixture was incubated at room temperature for 2 minutes. Luminescence was read on a BioTek Neo2 (BioTek. Winooski.Vt.) and IC50 values were determined using GraphPad® software (GraphPad Software Inc., San Diego, Calif., USA), in which ratio was plotted against log-transformed antibody concentration and IC50 values were determined using non-linear regression (curve fit) of sigmoidal dose-response. Control antibodies used in the STAT3 activation assay included PC1 (PC1 is a reference antibody known to be specific for p19, Biointron, LOT NO:20180926A04) as a positive control and mIgG2a as a negative control (generated in house).

Results: As shown in Table 5, the anti-IL-23p19-specific antibodies evaluated in the assay inhibited STAT3 activation with IC50 values ranging from 35.2 µM to 264.6 µM with maximal 99-100% inhibition. The positive control (PC1) had IC50 values ranging from 24.30 µM to 117.20 µM with 98-99% inhibition from multiple experiments.

TABLE 5

Inhibition of IL-23/IL-23 receptor-mediated STAT3 activation

| Anti-IL-23p19 mAb | IC50 pM | Top % of inhibition |
|---|---|---|
| Hu-2 18006B | 157.7 | 97% |
| Hu-4 18006B | 168.5 | 99% |
| Hu-5 18006B | 226.4 | 99% |
| Hu-6 18006B | 60.5 | 99% |
| Hu-6 18006B* | 35.2 | 99% |
| Hu-4 18006B* | 264.6 | 100% |
| Hu-4 18006B** | 157.4 | 100% |

Figure 7:
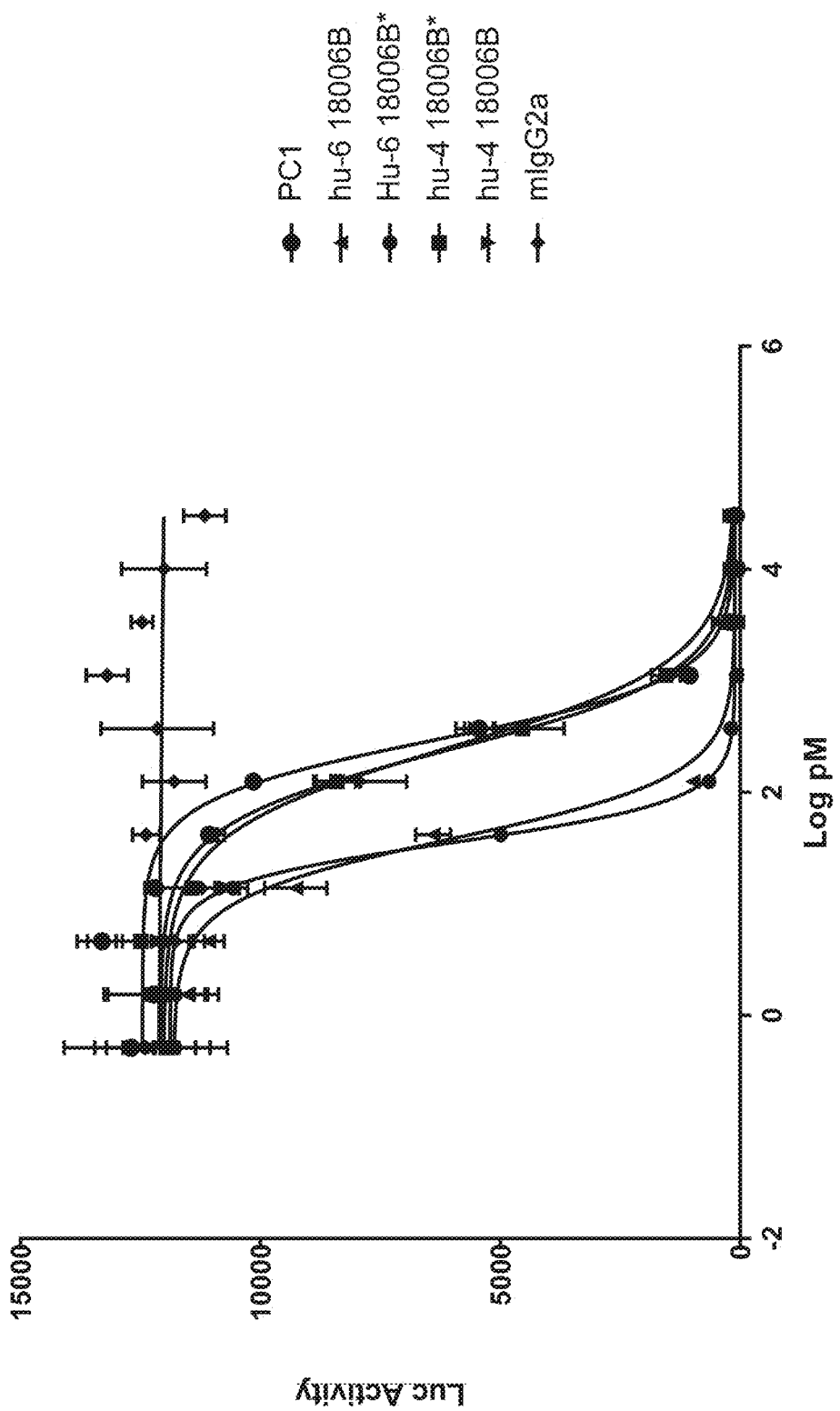
FIG. 7 shows inhibition of IL-23-induced STAT3 activation in a reporter cell assay by two representative anti-IL-23p19 antibodies.

Results from FIG. 7 indicated that the disclosed selected 4 anti-IL-23p19 antibodies (hu-4 18006B, hu-4-18006B*, hu-6 18006B and hu-6 18006B*) inhibited STAT3 activation in a dose dependent manner. The positive control (PC1) also showed inhibition of the STAT3 activation in a dose response manner as expected.

Example 6: Inhibition of IL-12-Depdentent IFN-γ Production by Human PBMC

IL-12 stimulation of PBMC is known to stimulate the production of IFN-γ by NK cells and T-cells. In order to determine if the disclosed anti-p19 antibodies can inhibit IFN-γ production, representative disclosed human anti-p19 antibodies were analyzed in a PMBC IL-12 stimulation assay.

Briefly, human PBMC were thawed from frozen stock and resuspended in RPMI+10% FBS containing 50 ng/ml of IL-18 (R&D, 9124-IL/CF) plate in a 384 well plate. A serial dilutions of the test antibodies were prepared in the growth medium in the Low Binding 384-well plate. human IL-12 (25 ng/ml) or cynomolgus monkey IL-12 (25 ng/ml) was transferred to each well followed by incubation at room temperature for 30 minutes. The mixture (tested antibodies+ IL-12) was plated to PBMC cell plate. The cells were incubated in a humidified 37° C./5% CO2 incubator for 48 hours. Production of IFN-γ was measured by AlphaLISA (PerkinElmer, AL217C) following the manufacturer's protocol.

Control antibodies used in the human PBMC assay: PC1 (a reference antibody known to be a p19 specific antibody, Biointron, LOT NO:20180926A04), PC2 (a reference antibody with known specificity for the p40 subunit of the IL-12 and IL-23, Biointron, LOT NO: 20180925A07), anti-IL-23 p40 subunit Mab (Hu-19 18006*, generated in-house); mIgG2a (generated by NovaRock Biotherapeutics) and human IgG4 (Dendritics, cat: DDXCHO4P-100, lot: DDXCH04-028) negative control antibodies.

Figure 8:
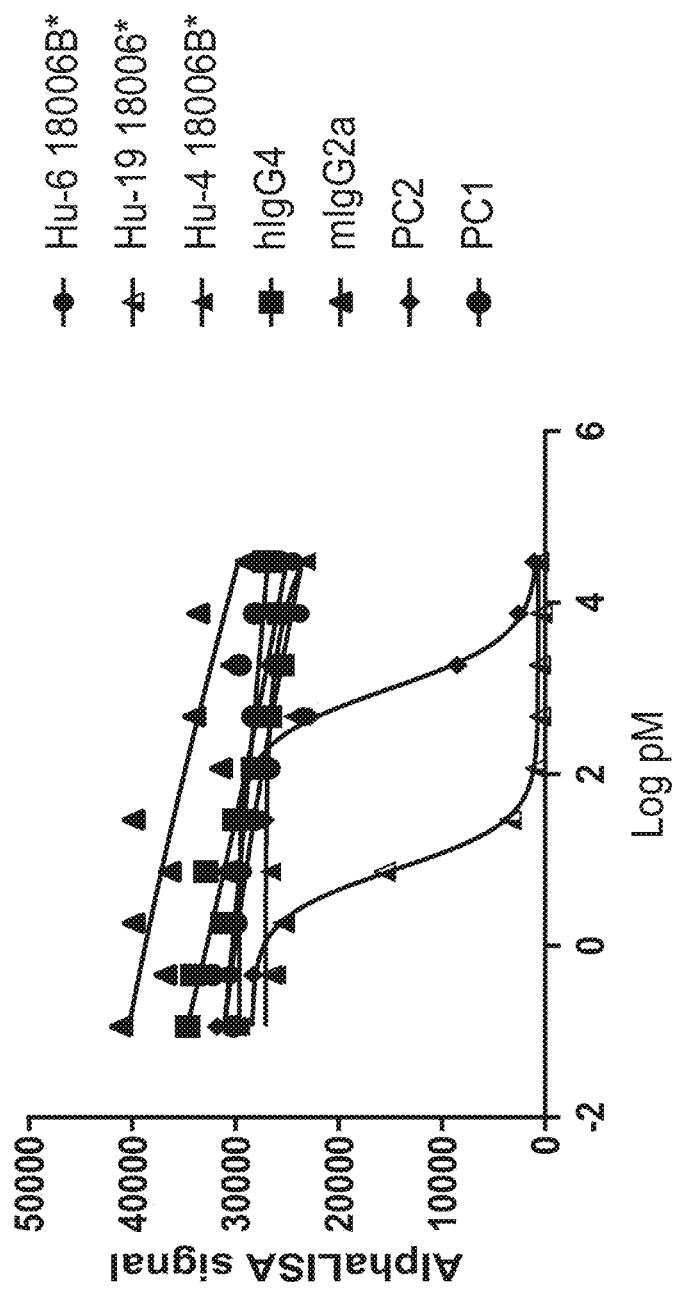
FIG. 8 shows no inhibition of human IL-12-induced IFN-γ production in human PBMCs by two representative anti-IL-23p19 specific antibodies.
Figure 9:
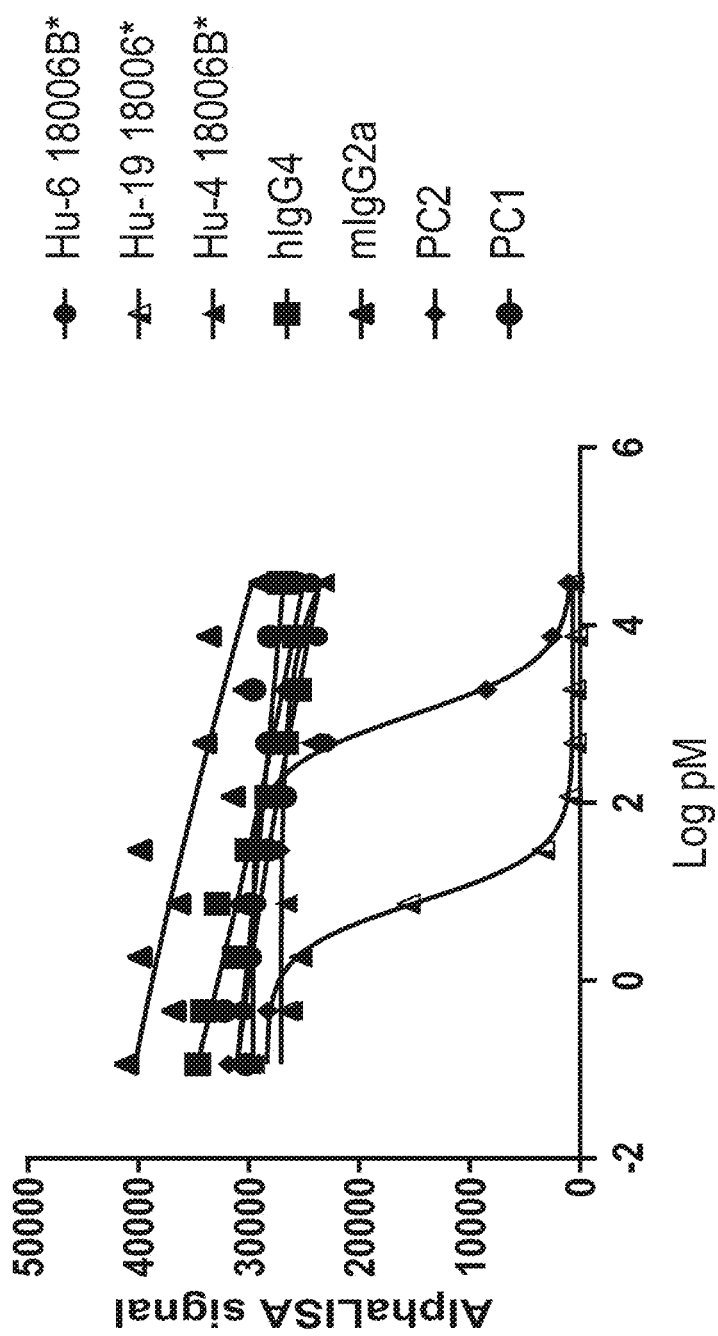
FIG. 9 shows no inhibition of cynomolgus monkey IL-12-induced IFN-γ production in human PBMCs by two representative anti-IL-23p19 antibodies.

Results: As showed in FIGS. 8 and 9, anti-IL-23p19 antibodies (Hu-6 18006B* and Hu-4 18006B* and PC1) did not inhibit human IL-12 (FIG. 8) and cynomolgus monkey IL-12 (FIG. 9) mediated IFN-γ production by human PBMC while the positive controls, PC2 and Hu-19 18006*, did in human (FIG. 8) and cynomolgus monkey (FIG. 9) PBMC in a dose-dependent manner as expected. This data supports the conclusion that the disclosed p19 antibodies are specific to p19.

Example 7: In Vivo Efficacy of Anti-p19-Specific Antibodies in an IL-23-Induced Murine Skin Inflammation Model The role of the IL-23/L-17 pathway as a key driver of human Psoriasis (PsO) is both well characterized and clinically validated. Animal models of Psoriasis (PsO) are important for our understanding of the pathophysiology of human diseases. Intradermal injection of IL-23 has been used to study the IL-23 pathway in rodents and can be used to assess the pharmacology of novel small molecules/biologics in the treatment of PsO (Stephen B. Gauld et al., *J. Dermatological Science*, 92 (2018) 45-53).

It is known that human IL-23 binds to murine IL-23 receptor and induces mIL-17 production and inflammation in mice. Intradermal injection of human IL-23 into mouse ears to induce mouse ear inflammation has been used for psoriasis model for characterizing biological drugs for human Psoriasis (PsO) (Aggarwal et al., *J Biol Chem* 2003; 278: 1910-4; Singh et al., *MAbs* 2015 July-August; 7(4): 77-791).

To assess the ability of the Hu-4 18006 B (mIgG2c), Hu-4 18006 B** (hIgG4), hu-5 18006B (mIgG2b) and Hu-618006 B* (mIgG2a) p19-specific antibodies to block IL-23 function in vivo, the antibodies were tested in a human IL-23-induced murine skin inflammation model. These representative antibodies were evaluated for their ability to decrease the inflammatory response.

In this model, recombinant human IL-23 (3 µg/10 µl/mouse/day) was injected into the skin (i.e., intradermally) of the mouse right ear for 8 consecutive days (D0-D7) to elicit a psoriasis-like inflammatory skin reaction characterized by erythema and induration with histological evidence of epidermal hyperplasia, parakeratosis and localized inflammatory infiltrate.

Figure 10:
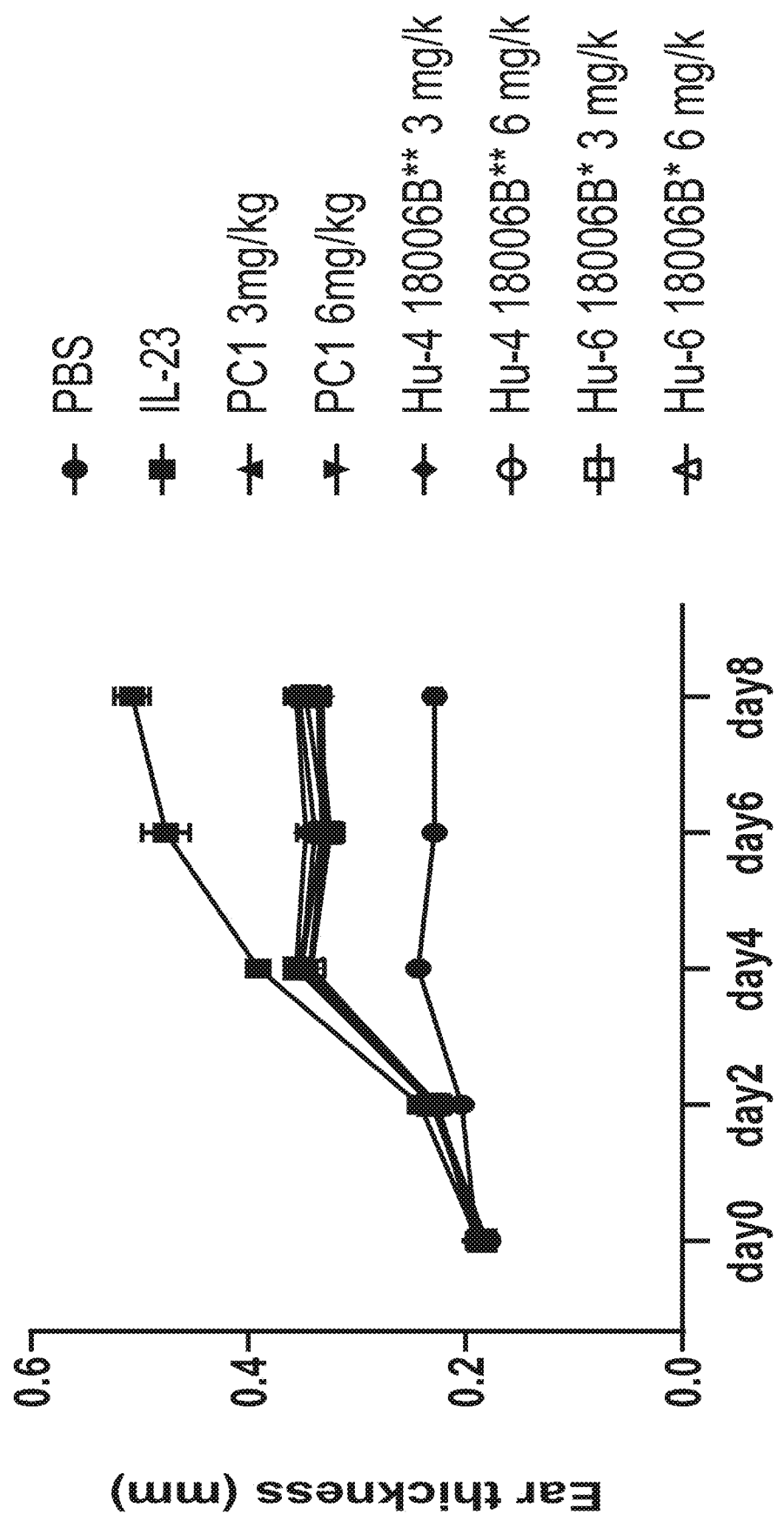
FIG. 10 shows in vivo inhibition of an IL-23 mediated inflammatory response (thickness of the ears) by two representative anti-IL-23p19 antibodies in a murine skin inflammation model explained in Example 7.

The mice were treated twice by intraperitoneal (i.p.) injection of IL-23p19 antibodies (hu-4 18006B, hu-4 18006B**, hu-5 18006B, or hu-6 18006B*) or PC1, a reference antibody known to be a p19 specific antibody (Biointron, LOT NO: 20180926A04) according to 2 protocols. In the first protocol, mice received PBS control (vehicle) or antibodies. The first injection was on the day before IL-23 injection and the second injection was on the third day after the IL-23 injection. In the second protocol, mice received PBS control or antibodies. The first injection was one hour before the IL-23 injection and the second injection was on the third day after the IL-23 injection (FIG. 10).

Mice were measured daily for body weight, ear thickness and inflammation score of the ears. The inflammation scores of the ears were calculated on day 0, day 2, day 4, day 6 and day 8, based on the following criteria: pinna shape (relatively normal-0; minimal change-; moderate to marked change-2; swelling and deformity severely-3). Skin color (relatively normal-0; minimal hyperplasia-1; minor hyperplasia-2; severe hyperplasia-3) and white scales (relatively normal-0; minimal-1; minor-2; obvious-3). The right ear thickness of each mouse was measured and photographed in day 0, day 2, day 4, day 6 and day 8.

On the last day of the experiment (day 8), the animals were disposed with carbon dioxide, the blood samples were collected, and the serums were separated (stored in −80° C. freezer). The modeling ears were collected and cut into two pieces: one piece was fixed in 10% neutral buffered formalin, and other piece was frozen in liquid nitrogen and stored in −80° C. freezer.

Data were given as Mean±SEM. Statistical significance were considered when the P value is less than 0.05.

The data provided in Tables 6 and 7 summarize the overall scores for the injected ears (by adding scores of pinna shape, skin color, microvessel change and white scales). The results indicated that the mice treated with the representative p19 specific antibodies experienced a diminished inflammatory response relative to the IL-23 injection model group. The effect started from day 4 and continued to day 8. The effect is statistically significant. This conclusion is apparent from both the summary score values and the ear thickness values.

TABLE 6

The overall scores of the injected ears (x ± s, n = 10)

| Group | Overall scores ## | | | | |
|---|---|---|---|---|---|
| | D0 | D2 | D4 | D6 | D8 |
| PBS | 0.0 ± 0.00 | 0.0 ± 0.00 | 0.0 ± 0.00 | 0.3 ± 0.95 | 0.2 ± 0.42 |
| IL-23 | 0.0 ± 0.00 | 0.0 ± 0.00 | 1.9 ± 1.37 | 9.6 ± 2.37 | 10.8 ± 1.93 |
| PC1 (10 mg/kg) | 0.0 ± 0.00 | 0.0 ± 0.00 | 0.6 ± 0.97* | 1.3 ± 1.34*** | 2.0 ± 2.05*** |
| Hu-4 18006B (10 mg/kg) | 0.0 ± 0.00 | 0.0 ± 0.00 | 0.6 ± 1.26* | 1.7 ± 1.83*** | 3.2 ± 3.05*** |
| Hu-5 18006B (10 mg/kg) | 0.0 ± 0.00 | 0.0 ± 0.00 | 0.8 ± 1.23 | 2.1 ± 1.60*** | 4.1 ± 2.33*** |

*p < 0.05, p < 0.01, *p < 0.001 vs. Model.

TABLE 7

The overall scores of the ears injected with IL-23 (x ± s, n = 8)

| Group | Overall scores ## | | | | |
|---|---|---|---|---|---|
| | D0 | D2 | D4 | D6 | D8 |
| PBS | 0 ± 0 | 0 ± 0 | 0 ± 0*** | 0 ± 0*** | 0 ± 0*** |
| IL-23 | 0 ± 0 | 0 ± 0 | 1.88 ± 0.3 | 5.63 ± 0.6 | 7.75 ± 0.53 |
| PC1 3 mg/kg | 0 ± 0 | 0 ± 0 | 0.5 ± 0.19** | 1.38 ± 0.26*** | 2.25 ± 0.25*** |
| PC-1 6 mg/kg | 0 ± 0 | 0 ± 0 | 0.38 ± 0.18** | 1 ± 0.33*** | 1.75 ± 0.25*** |
| Hu-4 18006B** 3 mg/kg | 0 ± 0 | 0 ± 0 | 0.5 ± 0.27** | 1.25 ± 0.37*** | 2.13 ± 0.3*** |
| Hu-4 18006B** 6 mg/kg | 0 ± 0 | 0 ± 0 | 0.25 ± 0.16** | 1.13 ± 0.3*** | 1.88 ± 0.23*** |
| Hu-6 18006B* 3 mg/kg | 0 ± 0 | 0 ± 0 | 0.38 ± 0.18** | 1.13 ± 0.35*** | 2.13 ± 0.23*** |
| Hu-6 18006B* 6 mg/kg | 0 ± 0 | 0 ± 0 | 0.25 ± 0.16 | 1 ± 0.27* | 1.75 ± 0.31*** | p < 0.01, *p < 0.001 vs. Model

As shown in Tables 8 and 9, the mouse ear thickness was reduced by the treatment of selected anti-IL-23p19 antibodies compared to the model (IL-23 treatment). The treatment effect (in vivo inhibition of inflammatory immune response in the skin) started from day 4 and continued to day 8 and the effect is statistically significant (p<0.001 vs. model, IL-23 treatment).

TABLE 8

The ear thickness of the injected ears in day 0 to day 8 (x ± s, n = 10)

| Group | Ear thickness (mm) | | | | |
|---|---|---|---|---|---|
| | D0 | D2 | D4 | D6 | D8 |
| PBS | 0.22 ± 0.02 | 0.19 ± 0.01 | 0.22 ± 0.01 | 0.23 ± 0.02 | 0.26 ± 0.02 |
| IL-23 | 0.23 ± 0.02 | 0.25 ± 0.01 | 0.37 ± 0.06 | 0.56 ± 0.09 | 0.65 ± 0.12 |
| PC1 (10 mg/kg) | 0.23 ± 0.02 | 0.23 ± 0.01 | 0.28 ± 0.08** | 0.35 ± 0.04*** | 0.33 ± 0.03*** |
| hu-4 18006B (10 mg/kg) | 0.23 ± 0.01 | 0.22 ± 0.02 | 0.31 ± 0.04* | 0.35 ± 0.03*** | 0.43 ± 0.07*** |
| hu-5 18006B (10 mg/kg) | 0.23 ± 0.01 | 0.23 ± 0.02 | 0.35 ± 0.02 | 0.42 ± 0.11** | 0.50 ± 0.15* |

*p < 0.05, p < 0.01, *p < 0.001 vs. Model.

TABLE 9

The ears thickness with the injection of IL-23 ($x \pm s$, n = 8)

| Group | Ears thickness (mm) | | | | |
|---|---|---|---|---|---|
| | D0 | D2 | D4 | D6 | D8 |
| PBS | 0.19 ± 0 | 0.2 ± 0*** | 0.24 ± 0*** | 0.23 ± 0*** | 0.23 ± 0.01*** |
| IL-23 | 0.19 ± 0 | 0.24 ± 0.01 | 0.39 ± 0.01 | 0.48 ± 0.02 | 0.51 ± 0.02 |
| PC1 3 mg/kg | 0.19 ± 0 | 0.23 ± 0 | 0.35 ± 0** | 0.33 ± 0.01*** | 0.34 ± 0.01*** |
| PC1 6 mg/kg | 0.19 ± 0 | 0.23 ± 0 | 0.34 ± 0*** | 0.33 ± 0.01*** | 0.33 ± 0.01*** |
| Hu-4 18006B** 3 mg/kg | 0.18 ± 0 | 0.23 ± 0 | 0.36 ± 0.01** | 0.35 ± 0.01*** | 0.36 ± 0.01*** |
| Hu-4 18006B** 6 mg/kg | 0.18 ± 0 | 0.23 ± 0 | 0.35 ± 0.01** | 0.34 ± 0.01*** | 0.35 ± 0.01*** |
| Hu-6 18006B* 3 mg/kg | 0.19 ± 0 | 0.23 ± 0 | 0.36 ± 0** | 0.33 ± 0.01*** | 0.35 ± 0*** |
| Hu-6 18006B* 6 mg/kg | 0.19 ± 0 | 0.23 ± 0 | 0.34 ± 0*** | 0.33 ± 0.01*** | 0.34 ± 0.01*** |

$p < 0.01$, *$p < 0.001$ vs. Model

The data provided in FIG. 10 shows that the disclosed anti-p19-specific antibodies hu-4 18006B** and hu-6 18006B* caused a statistically significant decrease in ear thickness compared to the untreated control (model receiving human IL-23 treatment only).

FIGS. 11A, 11B, 11C and 11D provide the data establishing the effect of the anti-p19-specific antibodies on the inflammatory skin reaction, as determined by H&E pathology staining scores, such as the thickness of the epidermis (FIG. 11A), thickness of the dermis (FIG. 11B), infiltration of inflammatory cells (FIG. 11C) and hyperkeratosis or insufficiency (FIG. 11D) obtained over the course of the experiment and represented by a score system as described below.

Briefly, on day 8, the mouse ears were collected and observed microscopically. The tissues were fixed in 10% neutral buffered formalin. After fixation, the tissues were trimmed, dehydrated, embedded, sectioned into slides and stained with hematoxylin/eosin (H&E) according to relevant SOPs. The study pathologist performed histopathology evaluation by a light microscope. A five-step grading system (relatively normal, minimal, mild, moderate to marked, severe) was used to categorize the microscopic findings.

Results: Treatment with the anti-p19 antibody hu4 18006B resulted in significant reductions of both the swelling response and the inflammation score induced by IL-23 injection compared to the model. Hu-4 18006B shows superior inhibition effect compared to PC1 on 3 of the scores, the thickness of the epidermis (FIG. 11A), the thickness of dermis (FIG. 11B) and infiltration of inflammatory cells (FIG. 11C). Hu-4 also showed inhibition of the hyperkeratosis (FIG. 11D).

FIG. 12 provides the representative photos of the H&E stained ear sections obtained on day 8 after the treatments. The H&E staining procedures are as described above.

Results: the selected disclosed anti-IL-23p19 antibody treatments (Hu-4 18006B) significantly inhibited mouse skin inflammation compared with the model.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

What is claimed is:

1. An anti-IL-23p19 antibody comprising: a heavy chain variable region comprising CDR1: SEQ ID NO: 15, CDR2: SEQ ID NO: 16, and CDR3: SEQ ID NO: 17; and a light chain variable region comprising CDR1: SEQ ID NO: 18, CDR2: SEQ ID NO: 19, and CDR3: SEQ ID NO: 20.

2. The anti-IL-23p19 antibody of claim 1, wherein the antibody comprises: a heavy chain variable region sequence comprising SEQ ID NO: 3 and a light chain variable region sequence comprising SEQ ID NO: 4.

3. The anti-IL-23p19 antibody of claim 1, wherein the antibody is a full-length antibody.

4. The anti-IL-23p19 antibody of claim 1, wherein the antibody is an antibody fragment.

5. The anti-IL-23p19 antibody of claim 4, wherein the antibody fragment is selected from the group consisting of: Fab, Fab', F(ab)2, Fv, scFv and scFv-Fc fragment, a single-chain antibody, a minibody, and a diabody.

6. The anti-IL-23p19 antibody of claim 1, wherein the antibody is a monoclonal antibody.

7. The anti-IL-23p19 antibody of claim 1, wherein the antibody is a human antibody.

8. The anti-IL-23p19 antibody of claim 1, wherein the antibody is a chimeric antibody.

9. The anti-IL-23p19 antibody of claim 1, wherein the antibody is an anti-human IL-23p19 antibody.

10. The anti-IL-23p19 antibody of claim 1, wherein the antibody does not bind the p40 subunit of IL-12.

11. A bispecific antibody comprising the anti-IL-23p19 antibody of claim 1.

12. A pharmaceutical composition comprising the antibody of claim 1 and a pharmaceutically acceptable carrier.

13. A method of treating an IL-23 mediated inflammatory disease, the method comprising administering the antibody of claim 1 to a patient in need thereof.

* * * * *